US009308145B2

(12) United States Patent
Jackson

(10) Patent No.: US 9,308,145 B2
(45) Date of Patent: Apr. 12, 2016

(54) PATIENT POSITIONING SUPPORT STRUCTURE

(76) Inventor: Roger P. Jackson, Prairie Village, KS (US)

( * ) Notice: Subject to any disclaimer, the term of this patent is extended or adjusted under 35 U.S.C. 154(b) by 726 days.

(21) Appl. No.: 13/374,034

(22) Filed: Dec. 8, 2011

(65) Prior Publication Data

US 2012/0198625 A1 Aug. 9, 2012

Related U.S. Application Data

(63) Continuation-in-part of application No. 12/460,702, filed on Jul. 23, 2009, now Pat. No. 8,060,960, which is a continuation of application No. 11/788,513, filed on Apr. 20, 2007, now Pat. No. 7,565,708, and a continuation-in-part of application No. 11/159,494, filed on Jun. 23, 2005, now Pat. No. 7,343,635, and a continuation-in-part of application No. 11/062,775, filed on Feb. 22, 2005, now Pat. No. 7,152,261.

(60) Provisional application No. 61/459,264, filed on Dec. 9, 2010, provisional application No. 60/798,288, filed on May 5, 2006.

(51) Int. Cl.
| A61G 13/04 | (2006.01) |
|---|---|
| A61G 13/08 | (2006.01) |
| A61G 7/00 | (2006.01) |
| A61G 7/008 | (2006.01) |
| A61G 13/00 | (2006.01) |

(52) U.S. Cl.
CPC ............... *A61G 7/001* (2013.01); *A61G 7/008* (2013.01); *A61G 13/0036* (2013.01); *A61G 13/04* (2013.01); *A61G 13/08* (2013.01); *A61G 2013/0054* (2013.01)

(58) Field of Classification Search
CPC ....... A61G 7/001; A61G 7/008; A61G 13/04; A61G 13/08; A61G 13/0036; A61G 2013/0054
USPC ...................... 5/601, 607, 608, 611–613, 617
See application file for complete search history.

(56) References Cited

U.S. PATENT DOCUMENTS

| 377,377 A | 2/1888 | Ferry |
|---|---|---|
| 1,098,477 A | 6/1914 | Cashman |

(Continued)

FOREIGN PATENT DOCUMENTS

| CN | 2467091 Y | 12/2001 |
|---|---|---|
| EP | 2226010 B1 | 6/2014 |

(Continued)

OTHER PUBLICATIONS

Brochure of Smith & Nephew on Spinal Positioning System, 2003, 2004.

(Continued)

*Primary Examiner* — Michael Trettel
(74) *Attorney, Agent, or Firm* — Polsinelli PC

(57) ABSTRACT

A patient support system includes independently adjustable end columns supporting a centrally hinged, jointed or breaking patient support structure. At least one column includes a powered rotation assembly. The patient support includes at least two sections. A coordinated drive system provides for both upwardly and downwardly breaking or jointed orientations of the two sections in various inclined and tilted positions. Cable, cantilevered and pull-rod systems are included. Primary and secondary elevators and a failsafe locking system are provided.

85 Claims, 43 Drawing Sheets

(56) References Cited

U.S. PATENT DOCUMENTS

| | | |
|---|---|---|
| 1,171,713 A | 2/1916 | Gilkerson |
| 1,528,835 A | 3/1925 | McCullough |
| 1,799,692 A | 8/1925 | Knott |
| 1,667,982 A | 5/1928 | Pearson |
| 1,780,399 A | 11/1930 | Munson |
| 1,938,006 A | 12/1933 | Blanchard |
| 1,990,357 A | 2/1935 | Ward |
| 2,188,592 A | 1/1940 | Hosken et al. |
| 2,261,297 A | 11/1941 | Frederick |
| 2,475,003 A | 7/1949 | Black |
| 2,636,793 A | 4/1953 | Meyer |
| 2,688,410 A | 9/1954 | Nelson |
| 2,792,945 A | 5/1957 | Brenny |
| 3,046,071 A | 7/1962 | Shampaine et al. |
| 3,049,726 A | 8/1962 | Getz |
| 3,281,141 A | 10/1966 | Smiley et al. |
| 3,584,321 A | 6/1971 | Buchanan |
| 3,599,964 A | 8/1971 | Magni |
| 3,766,384 A | 10/1973 | Anderson |
| 3,814,414 A | 6/1974 | Chapa |
| 3,832,742 A | 9/1974 | Stryker |
| 3,988,790 A | 11/1976 | Mracek et al. |
| 4,101,120 A | 7/1978 | Seshima |
| 4,131,802 A | 12/1978 | Braden et al. |
| 4,144,880 A | 3/1979 | Daniels |
| 4,148,472 A | 4/1979 | Rais et al. |
| 4,175,550 A | 11/1979 | Leininger et al. |
| 4,186,917 A | 2/1980 | Rais et al. |
| 4,227,269 A | 10/1980 | Johnston |
| 4,230,100 A | 10/1980 | Moon |
| 4,391,438 A | 7/1983 | Heffington, Jr. |
| 4,474,364 A | 10/1984 | Brendgord |
| 4,503,844 A | 3/1985 | Siczek |
| 4,552,346 A | 11/1985 | Schnelle et al. |
| 4,712,781 A | 12/1987 | Watanabe |
| 4,718,077 A | 1/1988 | Moore et al. |
| 4,763,643 A | 8/1988 | Vrzalik |
| 4,771,785 A | 9/1988 | Duer |
| 4,872,657 A | 10/1989 | Lussi |
| 4,887,325 A | 12/1989 | Tesch |
| 4,937,901 A | 7/1990 | Brennan |
| 4,944,500 A | 7/1990 | Mueller et al. |
| 4,953,245 A | 9/1990 | Jung |
| 4,970,737 A | 11/1990 | Sagel |
| 5,013,018 A | 5/1991 | Sicek et al. |
| 5,088,706 A | 2/1992 | Jackson |
| 5,131,105 A | 7/1992 | Harrawood et al. |
| 5,131,106 A | 7/1992 | Jackson |
| 5,161,267 A | 11/1992 | Smith |
| 5,163,890 A | 11/1992 | Perry, Jr. |
| 5,181,289 A | 1/1993 | Kassai |
| 5,208,928 A | 5/1993 | Kuck et al. |
| 5,210,887 A | 5/1993 | Kershaw |
| 5,210,888 A | 5/1993 | Canfield |
| 5,230,112 A | 7/1993 | Harrawood et al. |
| 5,231,741 A | 8/1993 | Maguire |
| 5,239,716 A | 8/1993 | Fisk |
| 5,274,862 A | 1/1994 | Palmer, Jr. |
| 5,333,334 A | 8/1994 | Kassai |
| 5,393,018 A | 2/1995 | Roth et al. |
| 5,444,882 A | 8/1995 | Andrews et al. |
| 5,461,740 A | 10/1995 | Pearson |
| 5,468,216 A | 11/1995 | Johnson et al. |
| 5,487,195 A | 1/1996 | Ray |
| 5,499,408 A | 3/1996 | Nix |
| 5,524,304 A | 6/1996 | Shutes |
| 5,544,371 A | 8/1996 | Fuller |
| 5,579,550 A | 12/1996 | Bathrick et al. |
| 5,588,705 A | 12/1996 | Chang |
| 5,613,254 A | 3/1997 | Clayman et al. |
| 5,640,730 A | 6/1997 | Godette |
| 5,645,079 A | 7/1997 | Zahiri et al. |
| 5,658,315 A | 8/1997 | Lamb et al. |
| 5,659,909 A | 8/1997 | Pfeuffer et al. |
| 5,673,443 A | 10/1997 | Marmor |
| 5,737,781 A | 4/1998 | Votel |
| 5,754,997 A | 5/1998 | Lussi et al. |
| 5,774,914 A | 7/1998 | Johnson et al. |
| 5,794,286 A | 8/1998 | Scott et al. |
| 5,862,549 A | 1/1999 | Morton et al. |
| 5,870,784 A | 2/1999 | Elliott |
| 5,890,238 A | 4/1999 | Votel |
| 5,901,388 A | 5/1999 | Cowan |
| 5,937,456 A | 8/1999 | Norris |
| 5,996,151 A | 12/1999 | Bartow et al. |
| 6,000,076 A | 12/1999 | Webster et al. |
| 6,035,465 A | 3/2000 | Rogozinski |
| 6,049,923 A | 4/2000 | Ochiai |
| 6,212,713 B1 | 4/2001 | Kuck et al. |
| 6,260,220 B1 | 7/2001 | Lamb et al. |
| 6,282,736 B1 | 9/2001 | Hand |
| 6,282,738 B1 | 9/2001 | Heimbrock et al. |
| 6,286,164 B1 | 9/2001 | Lamb et al. |
| 6,295,671 B1 | 10/2001 | Reesby et al. |
| 6,322,251 B1 | 11/2001 | Ballhaus et al. |
| 6,438,777 B1 | 8/2002 | Bender |
| 6,496,991 B1 | 12/2002 | Votel |
| 6,499,162 B1 | 12/2002 | Lu |
| 6,505,365 B1 | 1/2003 | Hanson et al. |
| 6,526,610 B1 | 3/2003 | Hand et al. |
| 6,634,043 B2 | 10/2003 | Lamb et al. |
| 6,638,299 B2 | 10/2003 | Cox |
| 6,662,388 B2 | 12/2003 | Friel |
| 6,668,396 B2 | 12/2003 | Wei |
| 6,681,423 B2 | 1/2004 | Zachrisson |
| 6,701,553 B1 | 3/2004 | Hand |
| 6,791,997 B2 | 9/2004 | Beyer et al. |
| 6,854,137 B2 | 2/2005 | Johnson |
| 6,857,144 B1 | 2/2005 | Huang |
| 6,862,759 B2 | 3/2005 | Hand et al. |
| 6,885,165 B2 | 4/2005 | Henley et al. |
| 6,971,131 B2 | 12/2005 | Bannister |
| 7,003,828 B2 | 2/2006 | Roussy |
| 7,055,195 B2 | 6/2006 | Roussy |
| 7,089,612 B2 | 8/2006 | Rocher et al. |
| 7,103,931 B2 | 9/2006 | Somasundaram et al. |
| 7,137,160 B2 | 11/2006 | Hand et al. |
| 7,152,261 B2 | 12/2006 | Jackson |
| 7,171,709 B2 | 2/2007 | Weismiller |
| 7,189,214 B1 | 3/2007 | Saunders |
| 7,197,778 B2 | 4/2007 | Sharps |
| 7,290,302 B2 | 11/2007 | Sharps |
| 7,331,557 B2 | 2/2008 | Dewert |
| 7,343,635 B2 | 3/2008 | Jackson |
| 7,428,760 B2 | 9/2008 | McCrimmon |
| 7,552,490 B2 | 6/2009 | Saracen et al. |
| 7,565,708 B2 | 7/2009 | Jackson |
| 7,596,820 B2 | 10/2009 | Nielsen et al. |
| 7,653,953 B2 | 2/2010 | Lopez-Sansalvador |
| 7,669,262 B2 | 3/2010 | Skripps et al. |
| 7,874,695 B2 | 1/2011 | Jensen |
| 8,060,960 B2 | 11/2011 | Jackson |
| 8,381,331 B2 | 2/2013 | Sharps et al. |
| 8,584,281 B2 | 11/2013 | Diel et al. |
| 8,677,529 B2 | 3/2014 | Jackson |
| 8,707,476 B2 | 4/2014 | Sharps |
| 8,719,979 B2 | 5/2014 | Jackson |
| 8,826,474 B2 | 9/2014 | Jackson |
| 8,826,475 B2 | 9/2014 | Jackson |
| 8,839,471 B2 | 9/2014 | Jackson |
| 8,844,077 B2 | 9/2014 | Jackson et al. |
| 8,856,986 B2 | 10/2014 | Jackson |
| 8,938,826 B2 | 1/2015 | Jackson |
| 8,978,180 B2 | 3/2015 | Jackson |
| 2001/0037524 A1 | 11/2001 | Truwit |
| 2002/0023298 A1 | 2/2002 | Lamb et al. |
| 2003/0055456 A1 | 3/2003 | Cox |
| 2003/0074735 A1 | 4/2003 | Zachrisson |
| 2003/0145383 A1 | 8/2003 | Schwaegerle |
| 2004/0098804 A1 | 5/2004 | Varadharajulu et al. |
| 2004/0133983 A1 | 7/2004 | Newkirk et al. |
| 2006/0123546 A1 | 6/2006 | Horton et al. |
| 2007/0107126 A1 | 5/2007 | Koch et al. |
| 2007/0192960 A1 | 8/2007 | Jackson |

(56) References Cited

U.S. PATENT DOCUMENTS

| | | |
|---|---|---|
| 2008/0000028 A1 | 1/2008 | Lemire et al. |
| 2008/0216241 A1 | 9/2008 | Mangiardi |
| 2009/0126116 A1 | 5/2009 | Lamb et al. |
| 2010/0037397 A1 | 2/2010 | Wood |
| 2010/0192300 A1 | 8/2010 | Tannoury et al. |
| 2011/0099716 A1 | 5/2011 | Jackson |
| 2011/0107516 A1 | 5/2011 | Jackson |
| 2011/0107517 A1 | 5/2011 | Lamb et al. |
| 2012/0144589 A1 | 6/2012 | Skripps et al. |
| 2012/0174319 A1 | 7/2012 | Menkedick |
| 2012/0246829 A1 | 10/2012 | Lamb et al. |
| 2012/0246830 A1 | 10/2012 | Hornbach |
| 2012/0255122 A1 | 10/2012 | Diel et al. |
| 2013/0111666 A1 | 5/2013 | Jackson |
| 2013/0133137 A1 | 5/2013 | Jackson |
| 2013/0198958 A1 | 8/2013 | Jackson et al. |
| 2013/0219623 A1 | 8/2013 | Jackson |
| 2013/0254994 A1 | 10/2013 | Jackson |
| 2013/0254995 A1 | 10/2013 | Jackson |
| 2013/0254996 A1 | 10/2013 | Jackson |
| 2013/0254997 A1 | 10/2013 | Jackson |
| 2013/0269710 A1 | 10/2013 | Hight et al. |
| 2013/0312187 A1 | 11/2013 | Jackson |
| 2013/0312188 A1 | 11/2013 | Jackson |
| 2013/0318718 A1 | 12/2013 | Jackson |
| 2013/0318719 A1 | 12/2013 | Jackson |
| 2013/0326812 A1 | 12/2013 | Jackson |
| 2013/0326813 A1 | 12/2013 | Jackson |
| 2014/0007349 A1 | 1/2014 | Jackson |
| 2014/0020181 A1 | 1/2014 | Jackson |
| 2014/0033436 A1 | 2/2014 | Jackson |
| 2014/0068861 A1 | 3/2014 | Jackson et al. |
| 2014/0082842 A1 | 3/2014 | Jackson |
| 2014/0109316 A1 | 4/2014 | Jackson et al. |
| 2014/0173826 A1 | 6/2014 | Jackson |
| 2014/0196212 A1 | 7/2014 | Jackson |
| 2014/0201913 A1 | 7/2014 | Jackson |
| 2014/0201914 A1 | 7/2014 | Jackson |
| 2014/0208512 A1 | 7/2014 | Jackson |
| 2014/0317847 A1 | 10/2014 | Jackson |
| 2015/0007391 A1 | 1/2015 | Xu |
| 2015/0059094 A1 | 3/2015 | Jackson |
| 2015/0150743 A1 | 6/2015 | Jackson |

FOREIGN PATENT DOCUMENTS

| | | |
|---|---|---|
| GB | 569758 | 6/1945 |
| GB | 810956 | 3/1959 |
| JP | S53763 | 1/1978 |
| JP | 2000060995 | 2/2000 |
| WO | 9907320 | 2/1999 |
| WO | 0062731 | 10/2000 |
| WO | WO 00/62731 | 10/2000 |
| WO | 0160308 | 8/2001 |
| WO | 03070145 | 8/2003 |
| WO | WO 2007/130679 A2 | 11/2007 |
| WO | 2009054969 | 4/2009 |
| WO | 2009100692 | 8/2009 |
| WO | WO2010/051303 A1 | 5/2010 |

OTHER PUBLICATIONS

Brochure of OSI on Modular Table System 90D, pp. 1-15, date of first publication: Unknow.
Pages from website http://www.schaerermayfieldusa.com, pgs. 1-5, date of first publication: Unknown.
Complaint for Patent Infringement, *Jackson v. Mizuho Orthopedic Sys., Inc.*, No. 4:12-CV-01031 (W.D. Mo. Aug. 7, 2012).
First Amended Complaint for Patent Infringement and Correction of Inventorship, *Jackson v. Mizuho Orthopedic Sys., Inc.*, No. 4:12-CV-01031 (W.D. Mo. Sep. 21, 2012).
Defendant Mizuho Orthopedic Systems, Inc.'s Answer to First Amended Complaint and Counterclaims, *Jackson v. Mizuho Orthopedic Sys., Inc.*, No. 4:12-CV-01031 (W.D. Mo. Nov. 1, 2012).
Plaintiff Roger P. Jackson, MD's, Reply to Counterclaims, *Jackson v. Mizuho Orthopedic Sys., Inc.*, No. 4:12-CV-01031 (W.D. Mo. Nov. 26, 2012).
Roger P. Jackson's Disclosure of Asserted Claims and Preliminary Infringement Contentions, *Jackson v. Mizuho Orthopedic Sys., Inc.*, No. 4:12-CV-01031 (W.D. Mo. Jan. 4, 2013).
Second Amended Complaint for Patent Infringement, for Correction of Inventorship, For Breach of a Non-Disclosure and Confidentiality Agreement, and for Misappropriation of Dr. Jackson's Right of Publicity, *Jackson v. Mizuho Orthopedic Sys., Inc.*, No. 4:12-CV-01031 (W.D. Mo. Jan. 28, 2013).
Defendant Mizuho Orthopedic Systems, Inc.'s Answer to Second Amended Complaint and Counterclaims, *Jackson v. Mizuho Orthopedic Sys., Inc.*, No. 4:12-CV-01031 (W.D. Mo. Feb. 19, 2013).
Defendant Mizuho Osi's Invalidity Contentions Pursuant to the Parties' Joint Scheduling Order, *Jackson v. Mizuho Orthopedic Sys., Inc.*, No. 4:12-CV-01031 (W.D. Mo. Feb. 22, 2013).
Plaintiff Roger P. Jackson, MD's, Reply to Second Counterclaims, *Jackson v. Mizuho Orthopedic Sys., Inc.*, No. 4:12-CV-01031 (W.D. Mo. Mar. 12, 2013).
Roger P. Jackson, MD's Disclosure of Proposed Terms to Be Construed, *Jackson v. Mizuho Orthopedic Sys., Inc.*, No. 4:12-CV-01031 (W.D. Mo. Apr. 5, 2013).
Defendant Mizuho Orthopedic Systems, Inc.'s Disclosure of Proposed Terms and Claim Elements for Construction, *Jackson v. Mizuho Orthopedic Sys., Inc.*, No. 4:12-CV-01031 (W.D. Mo. Apr. 5, 2013).
Mizuho Orthopedic Systems, Inc.'s Disclosure of Proposed Claim Constructions and Extrinsic Evidence, *Jackson v. Mizuho Orthopedic Sys., Inc.*, No. 4:12-CV-01031 (W.D. Mo. May 13, 2013).
Plaintiff Roger P. Jackson, MD's Disclosure of Preliminary Proposed Claim Constructions, *Jackson v. Mizuho Orthopedic Sys., Inc.*, No. 4:12-CV-01031 (W.D. Mo. May 13, 2013).
Defendant Mizuho Osi's Amended Invalidity Contentions Pursuant to the Parties' Joint Scheduling Order, *Jackson v. Mizuho Orthopedic Sys., Inc.*, No. 4:12-CV-01031 (W.D. Mo. May 15, 2013).
Joint Claim Construction Chart and Joint Prehearing Statement, *Jackson v. Mizuho Orthopedic Sys., Inc.*, No. 4:12-CV-01031 (W.D. Mo. Jun. 7, 2013).
Defendant Mizuho Orthopedic Systems, Inc.'s Objections and Responses to Plaintiffs First Set of Interrogatories, *Jackson v. Mizuho Orthopedic Sys., Inc.*, No. 4:12-CV-01031 (W.D. Mo. Jun. 24, 2013).
Defendant Mizuho Orthopedic Systems, Inc.'s Opening Claim Construction Brief, *Jackson v. Mizuho Orthopedic Sys., Inc.*, No. 4:12-CV-01031 (W.D. Mo. Jul. 31, 2013).
Plaintiff Roger P. Jackson, MD's Opening Claim Construction Brief, *Jackson v. Mizuho Orthopedic Sys., Inc.*, No. 4:12-CV-01031 (W.D. Mo. Jul. 31, 2013).
Appendix A Amended Infringement Contentions Claim Chart for Mizuho's Axis System Compared to U.S. Pat. No. 7,565,708, *Jackson v. Mizuho Orthopedic Sys., Inc.*, No. 4:12-CV-01031 (W.D. Mo. Aug. 12, 2013).
Appendix B Amended Infringement Contentions Claim Chart for Mizuho's Axis System Compared to U.S. Pat. No. 8,060,960, *Jackson v. Mizuho Orthopedic Sys., Inc.*, No. 4:12-CV-01031 (W.D. Mo. Aug. 12, 2013).
Appendix C Amended Infringement Contentions Claim Chart for Mizuho's Proaxis System Compared to U.S. Pat. No. 7,565,708, *Jackson v. Mizuho Orthopedic Sys., Inc.*, No. 4:12-CV-01031 (W.D. Mo. Aug. 12, 2013).
Appendix D Amended Infringement Contentions Claim Chart for Mizuho's Proaxis System Compared to U.S. Pat. No. 8,060,960, *Jackson v. Mizuho Orthopedic Sys., Inc.*, No. 4:12-CV-01031 (W.D. Mo. Aug. 12, 2013).
Plaintiff Roger P. Jackson, MD's Responsive Claim Construction Brief, *Jackson v. Mizuho Orthopedic Sys., Inc.*, No. 4:12-CV-01031 (W.D. Mo. Aug. 16, 2013).
Defendant Mizuho Orthopedic Systems, Inc's Brief in Response to Plaintiffs Opening Claim Construction Brief, *Jackson v. Mizuho Orthopedic Sys., Inc.*, No. 4:12-CV-01031 (W.D. Mo. Aug. 16, 2013).

(56) References Cited

OTHER PUBLICATIONS

Plaintiff Roger P. Jackson, MD's Suggestions in Support of His Motion to Strike Exhibit A of Mizuho's Opening Claim Construction Brief, *Jackson v. Mizuho Orthopedic Sys., Inc.*, No. 4:12-CV-01031 (W.D. Mo. Aug. 16, 2013).
Defendant Mizuho Orthopedic Systems, Inc.'s Opposition to Plaintiffs Motion to Strike, *Jackson v. Mizuho Orthopedic Sys., Inc.*, No. 4:12-CV-01031 (W.D. Mo. Sep. 3, 2013).
Transcript of Claim Construction Hearing, *Jackson v. Mizuho Orthopedic Sys., Inc.*, No. 4:12-CV-01031 (W.D. Mo. Oct. 11, 2013).
Plaintiff Roger P. Jackson, MD's Claim Construction Presentation for U.S. District Judge Nanette K. Laughrey, *Jackson v. Mizuho Orthopedic Sys., Inc.*, No. 4:12-CV-01031 (W.D. Mo. Oct. 11, 2013).
Mizuho's Claim Construction Argument, *Jackson v. Mizuho Orthopedic Sys., Inc.*, No. 4:12-CV-01031 (W.D. Mo. Oct. 11, 2013).
Order, *Jackson v. Mizuho Orthopedic Sys., Inc.*, No. 4:12-CV-01031 (W.D. Mo. Apr. 4, 2014).
Australian Patent Examination Report No. 2, AU2014200274, dated Oct. 9, 2015.
Canadian Office Action, CA2803110, dated Mar. 5, 2015.
Chinese Office Action, CN 201180039162.0, dated Jan. 19, 2015.
European Search Report, EP11798501.0, dated Mar. 30, 2015.
Japanese Office Action, JP 2014-132463, dated Jun. 18, 2015.
Japanese Office Action, JP 2014-142074, dated Jun. 18, 2015.
Quayle Action, U.S. Appl. No. 14/792,216, dated Sep. 9, 2015.
European Examination Report, EP11798501.0, dated Nov. 12, 2015.
Japanese Final Rejection (English version), JP 2014-142074, dated Dec. 6, 2015.
International Search Report and Written Opinion of the International Searching Authority, PCT/US2015/039400, dated Dec. 7, 2015, 13 pages.

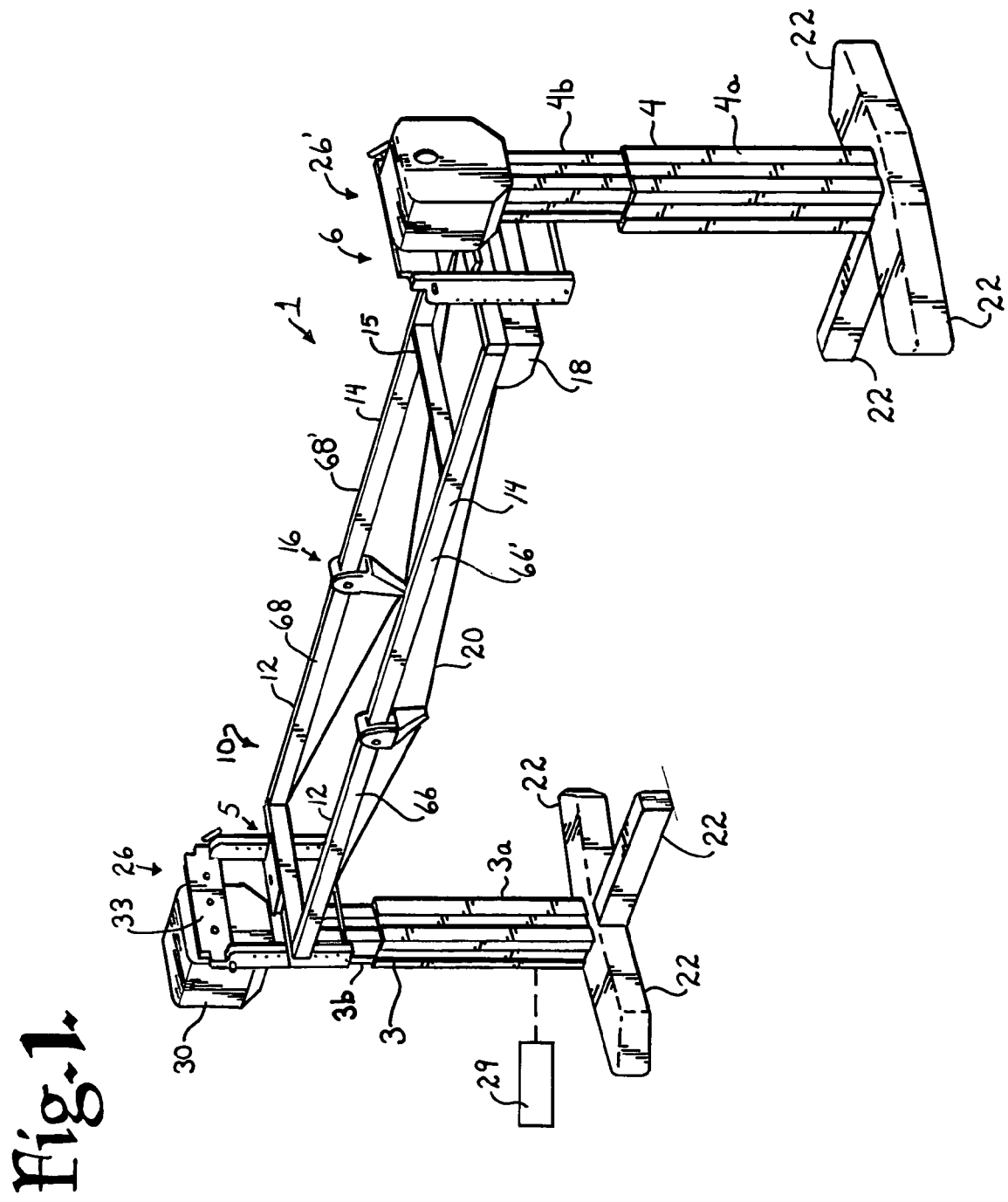

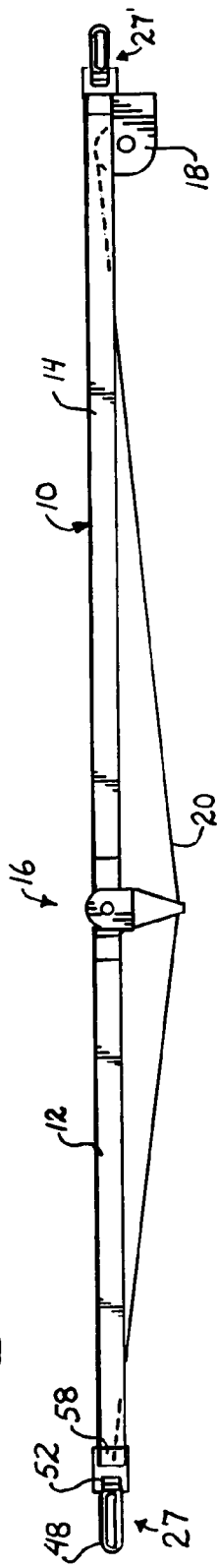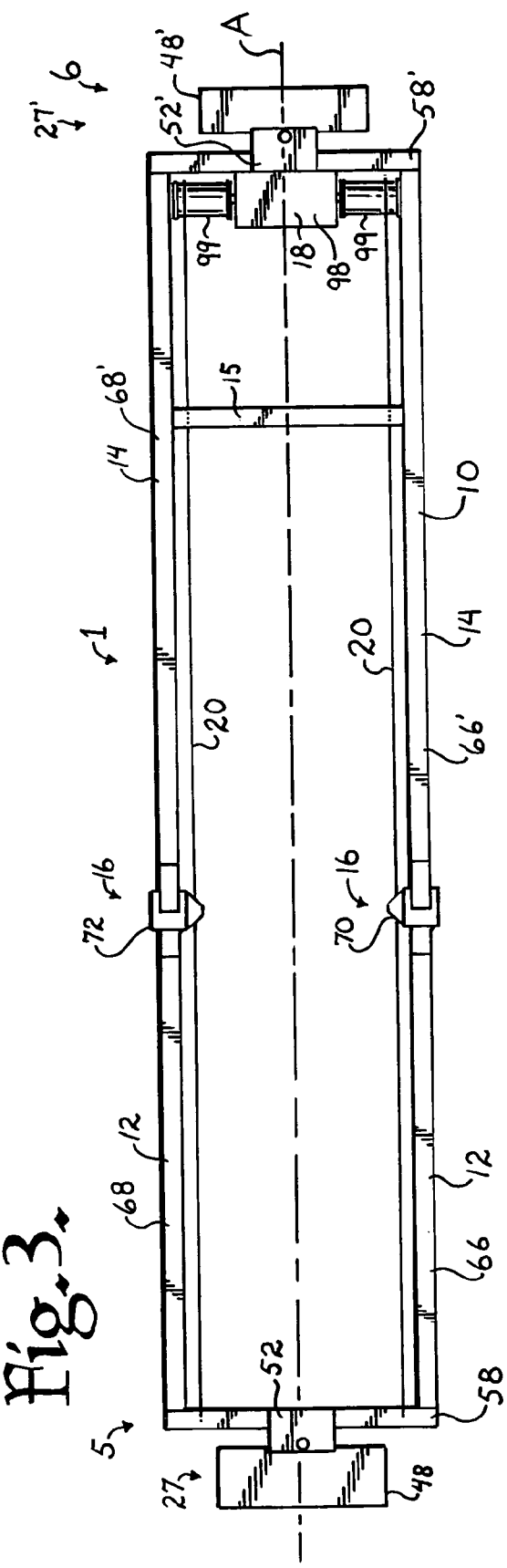

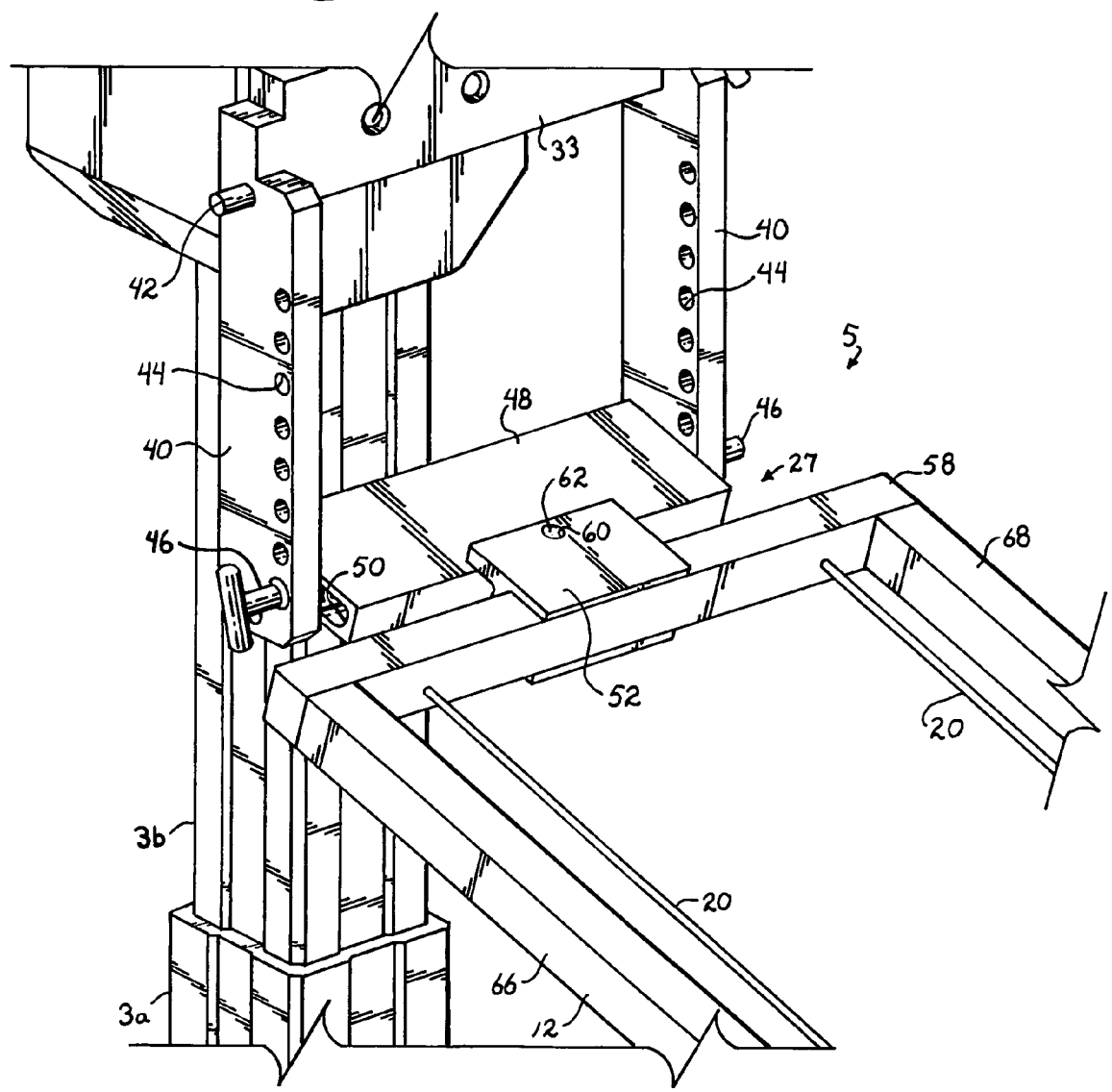

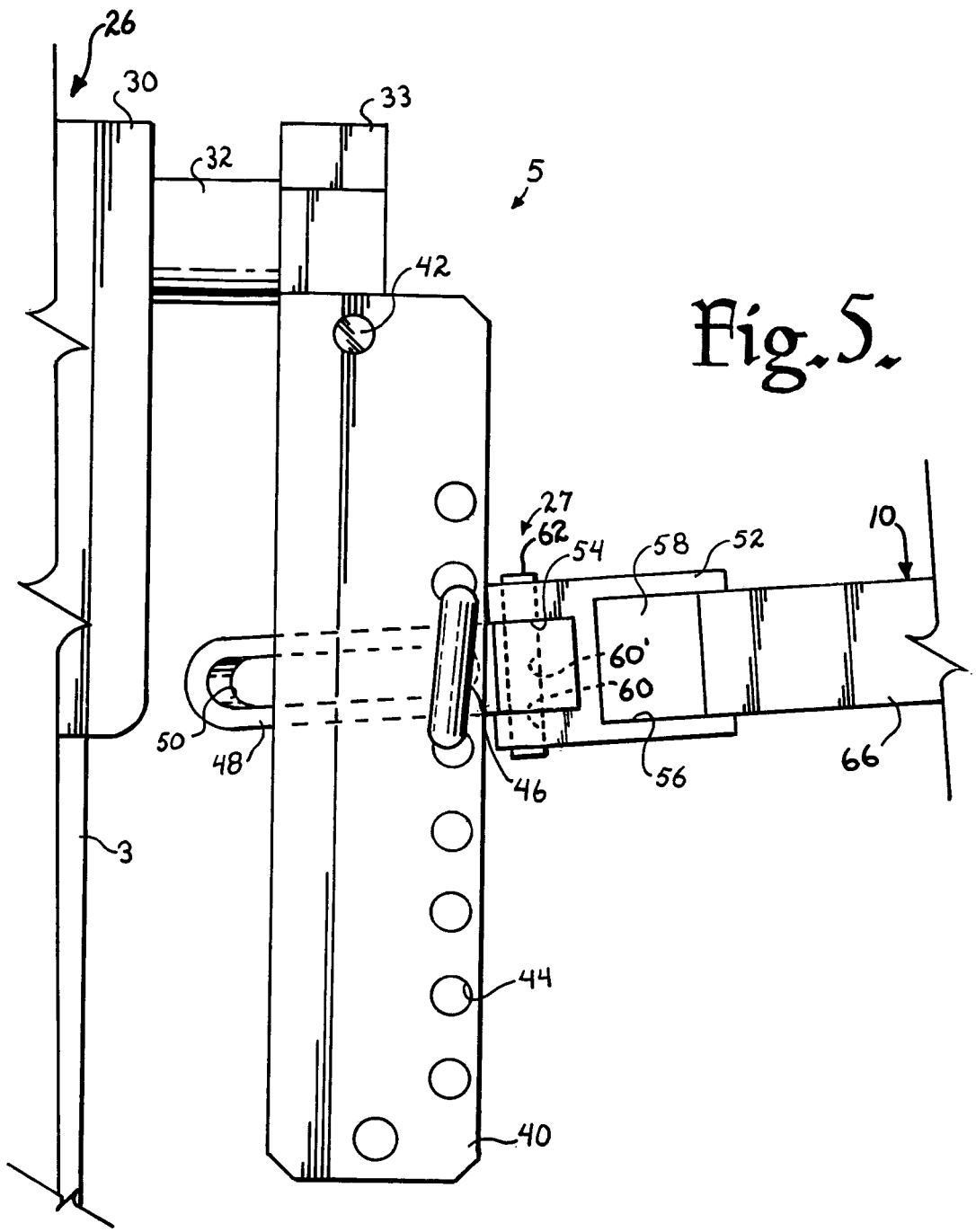

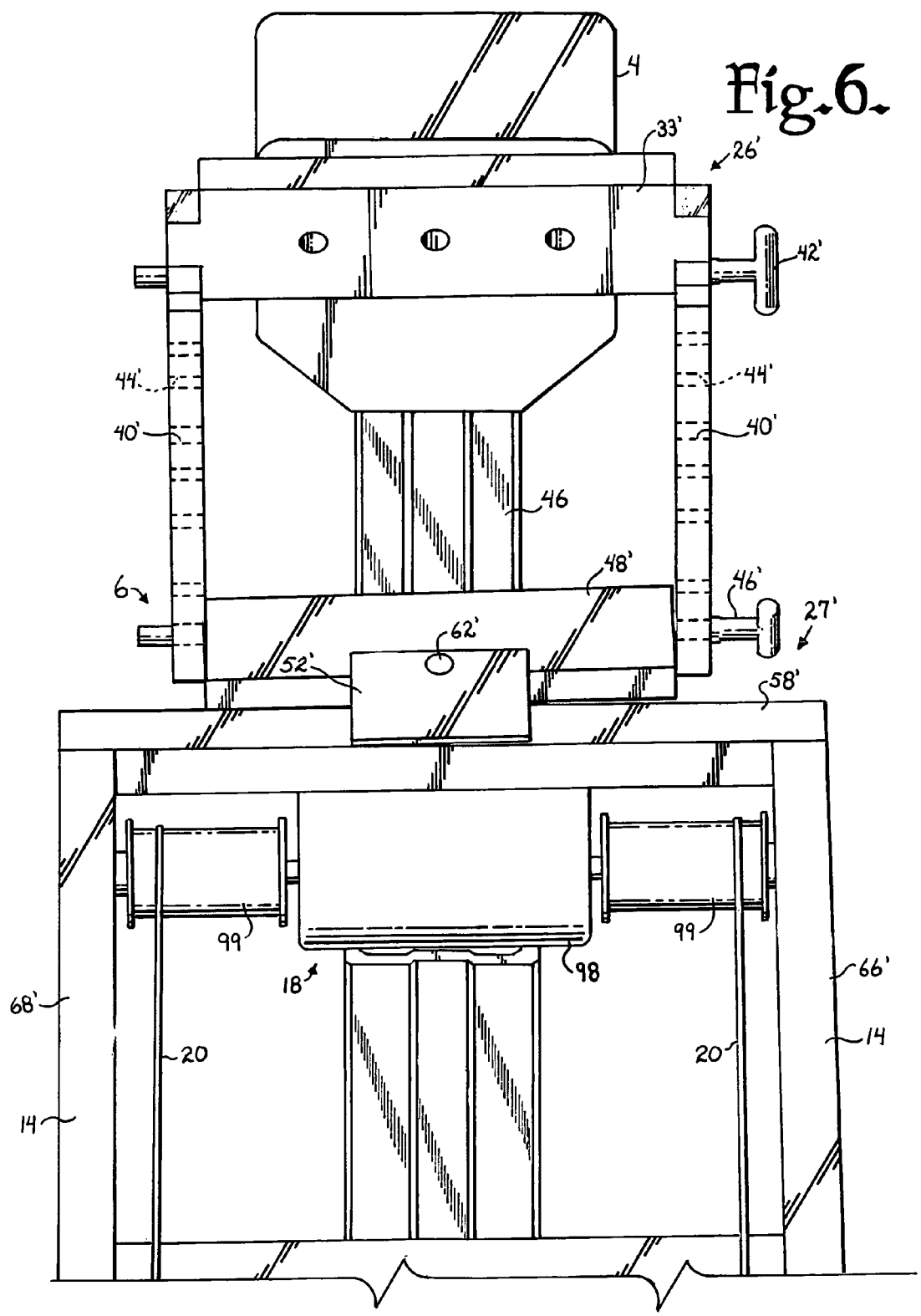

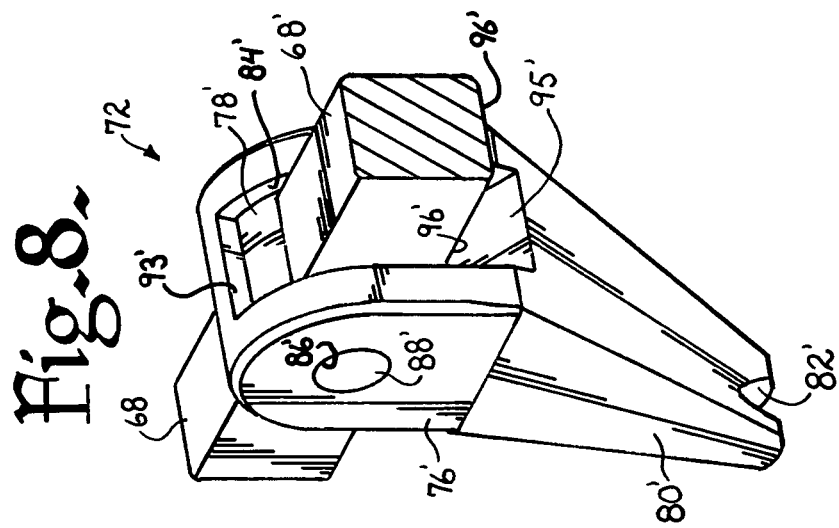
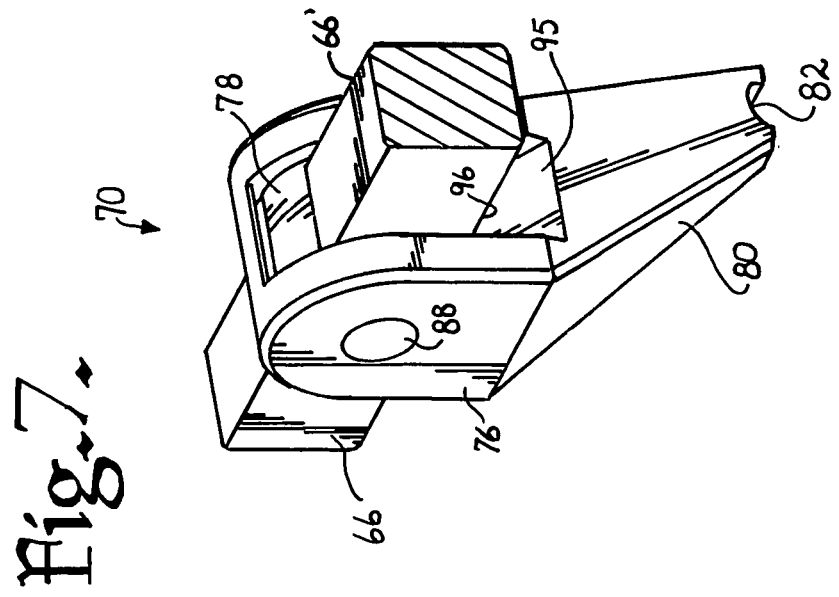

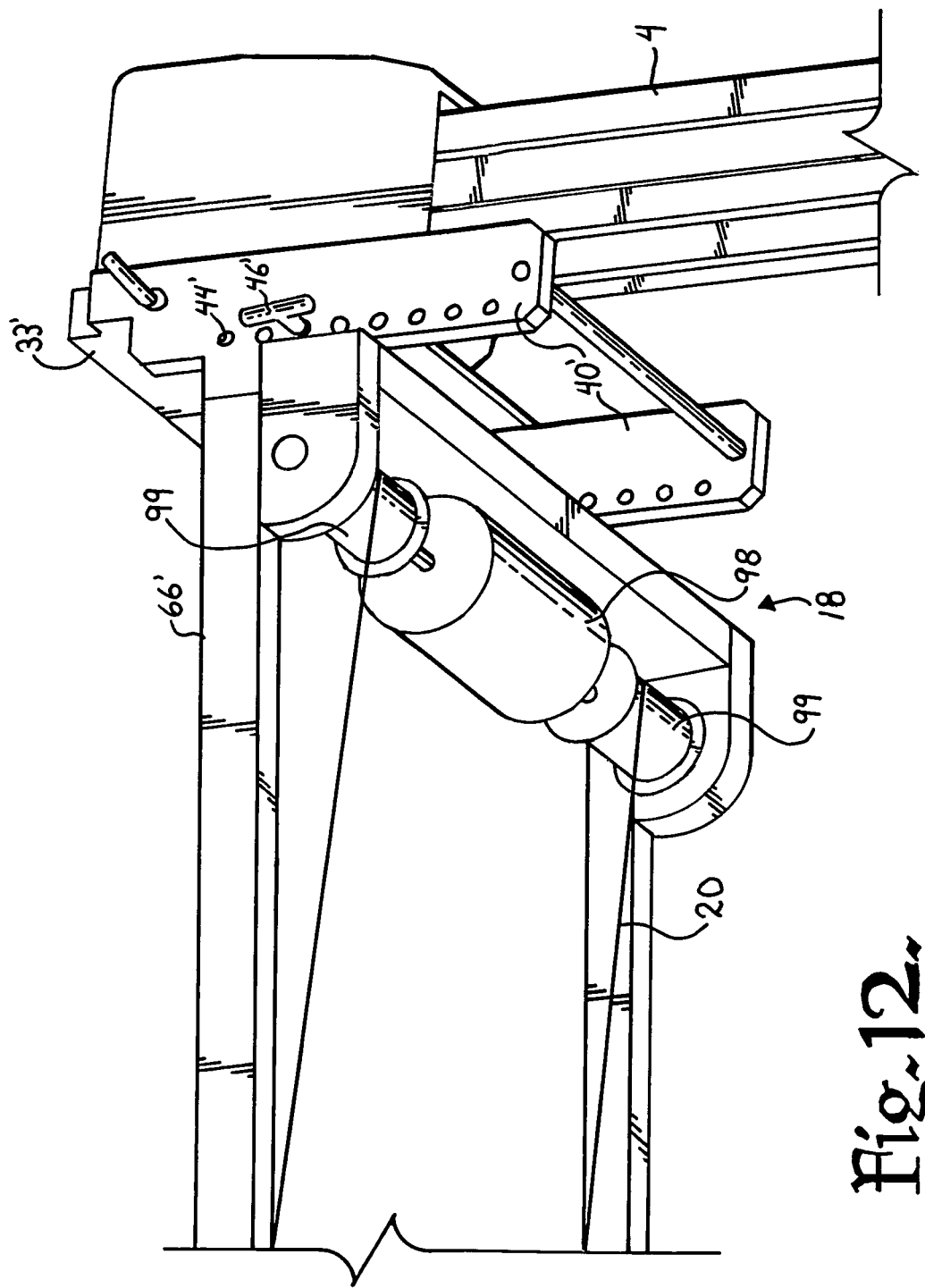

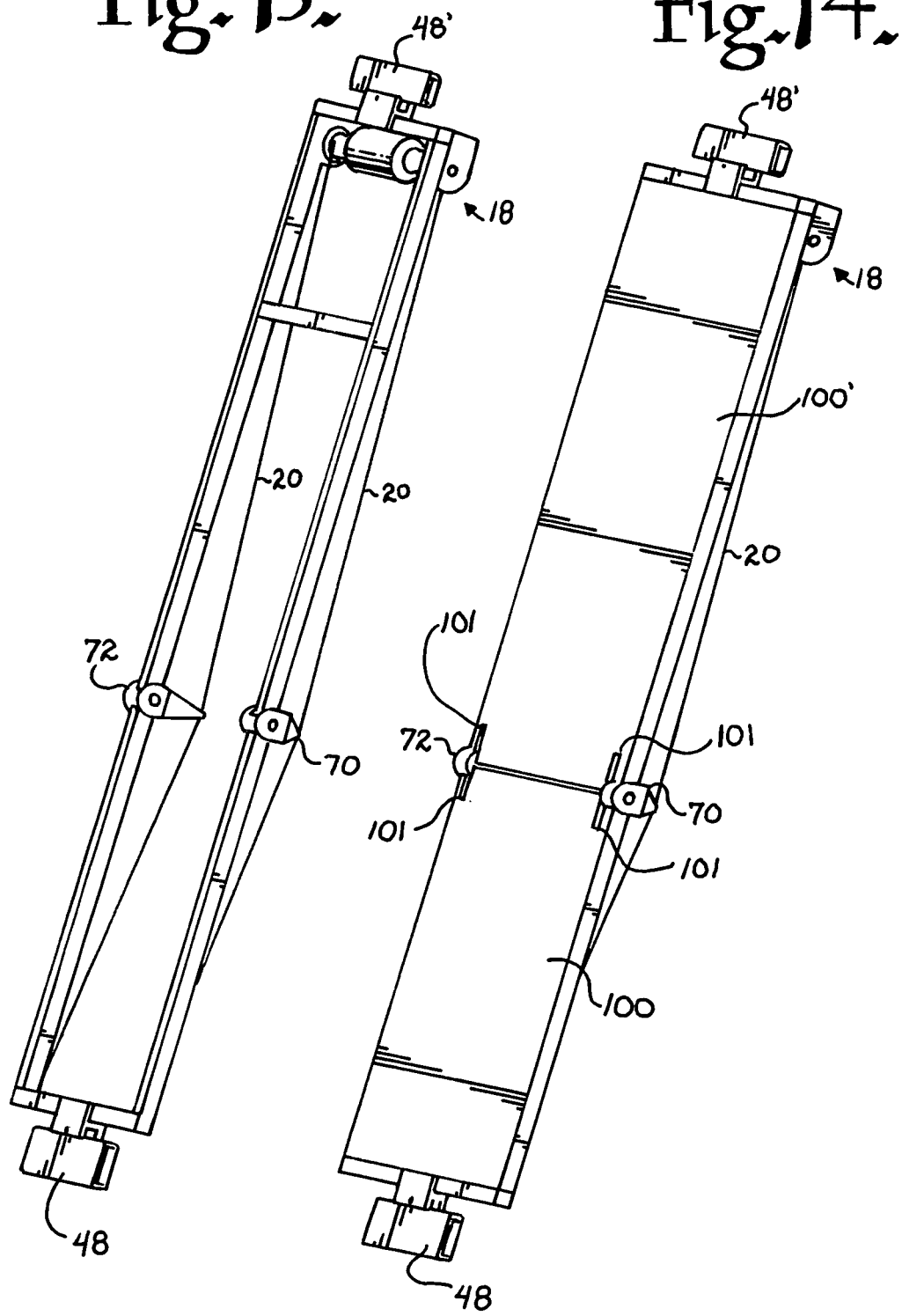

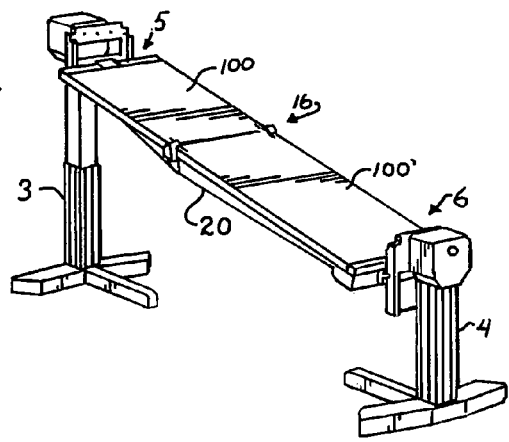
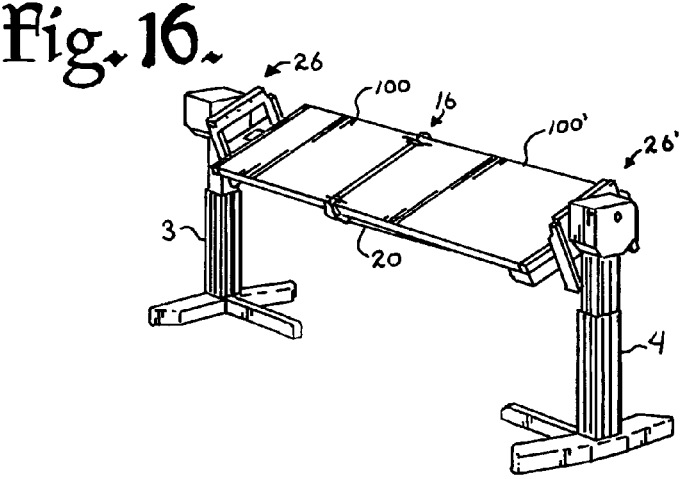
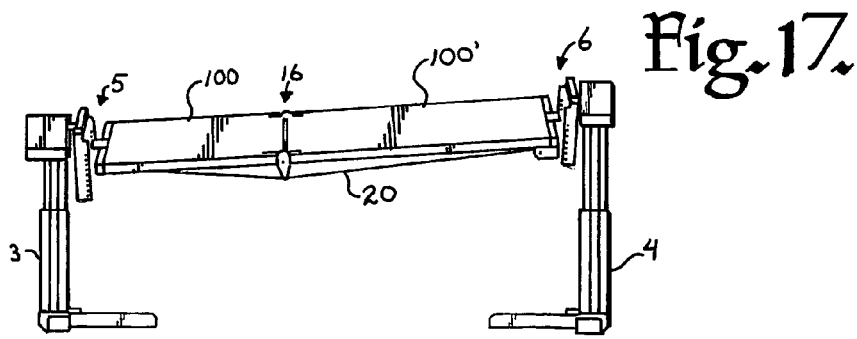

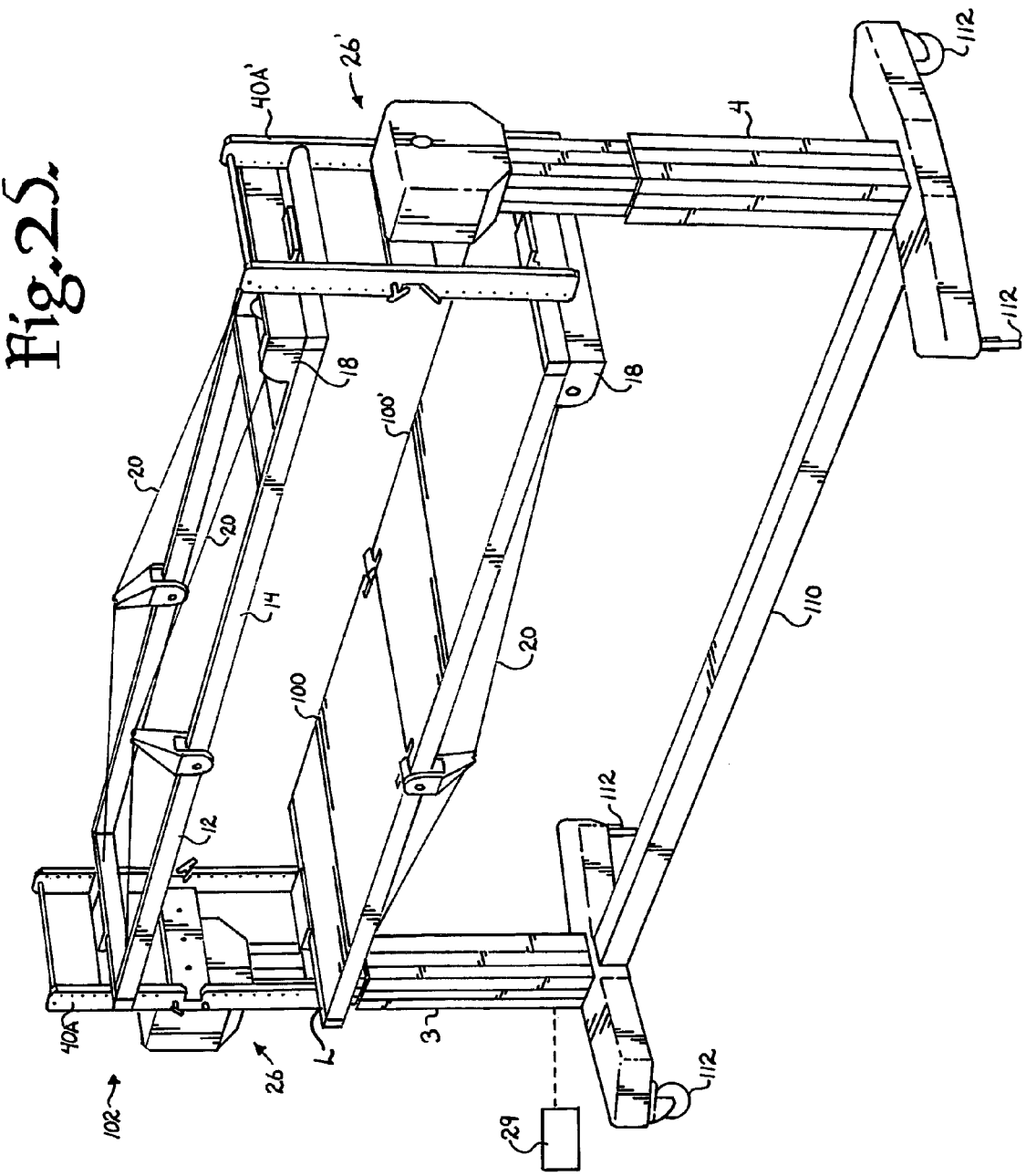

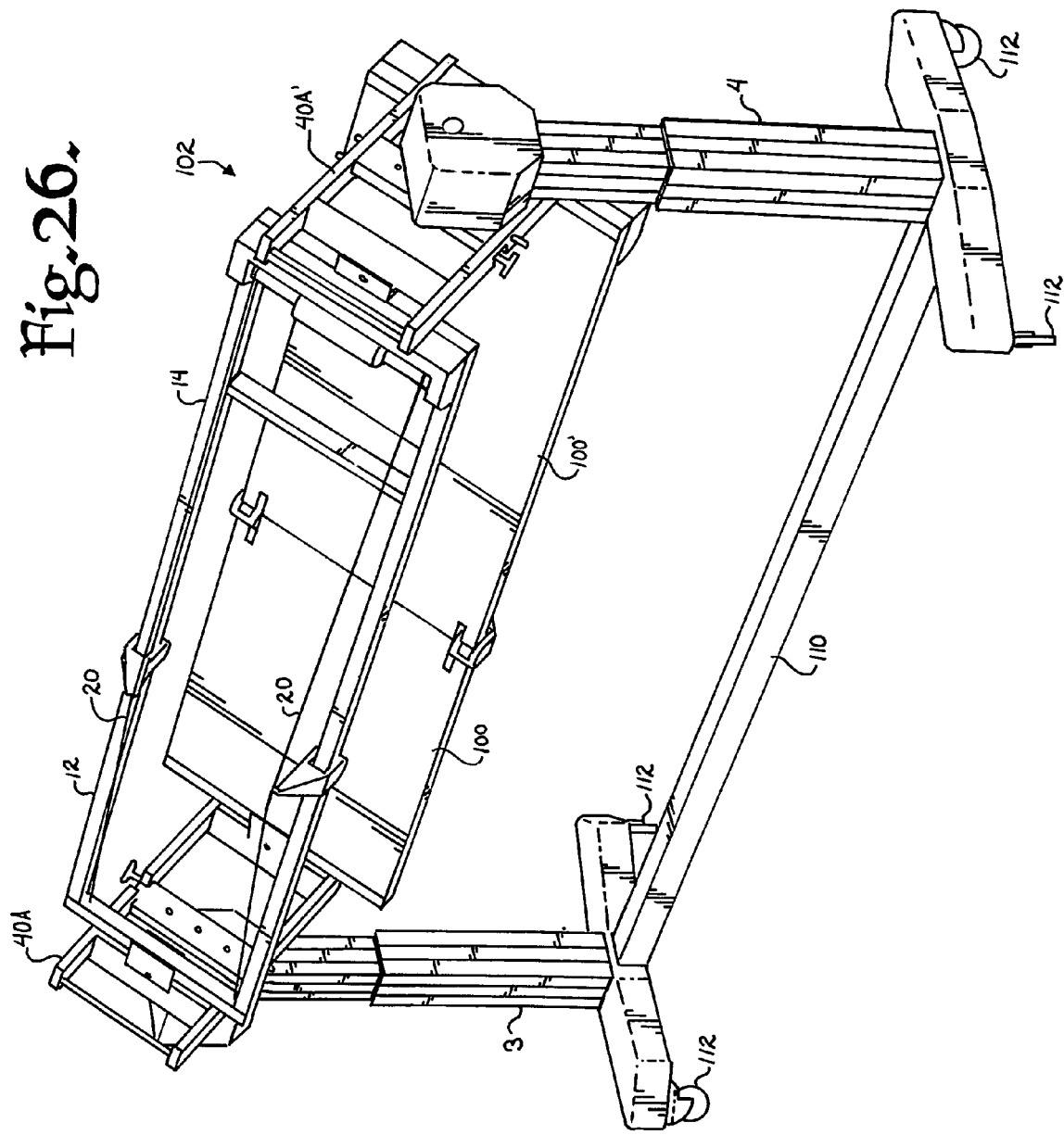

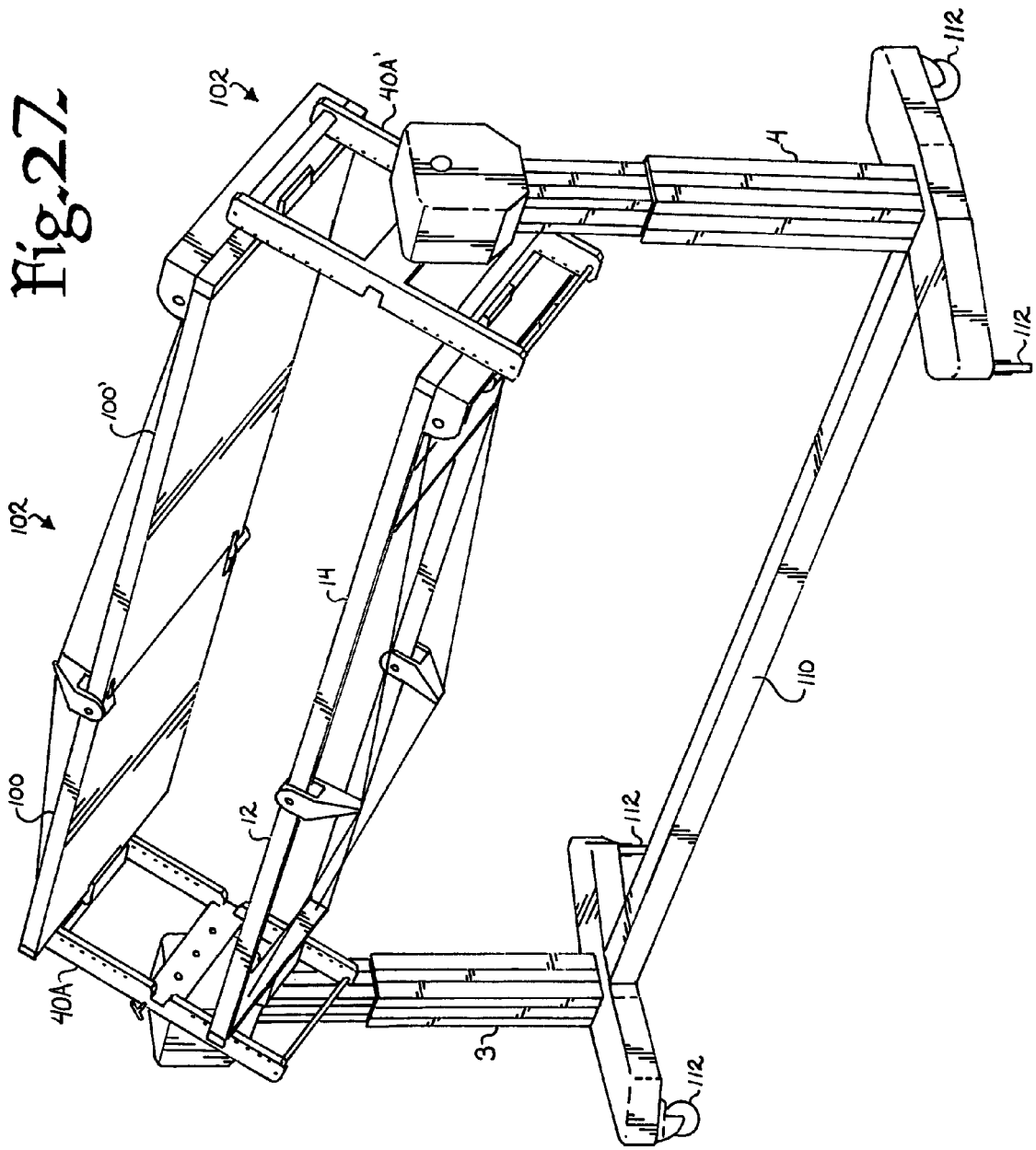

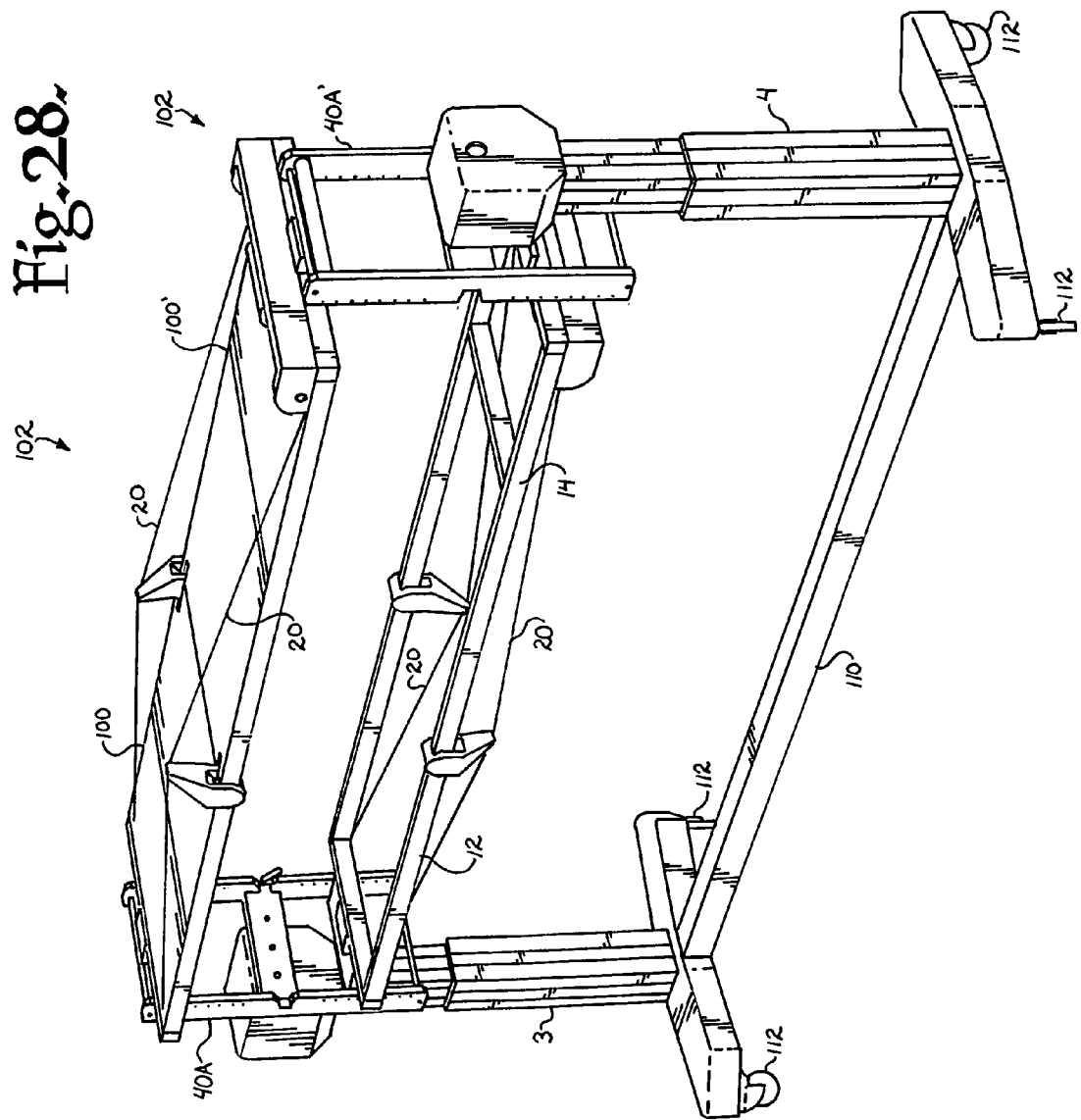

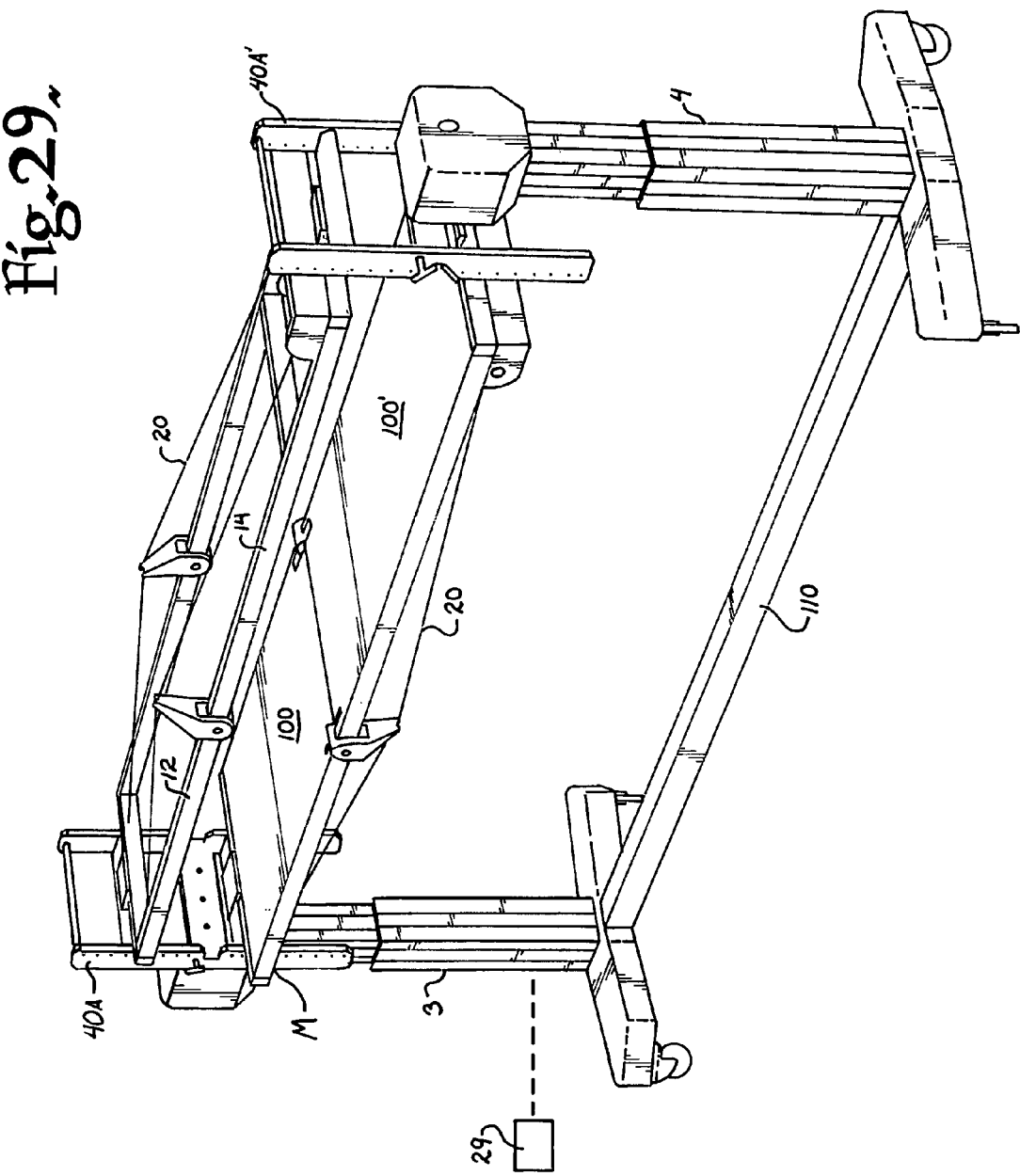

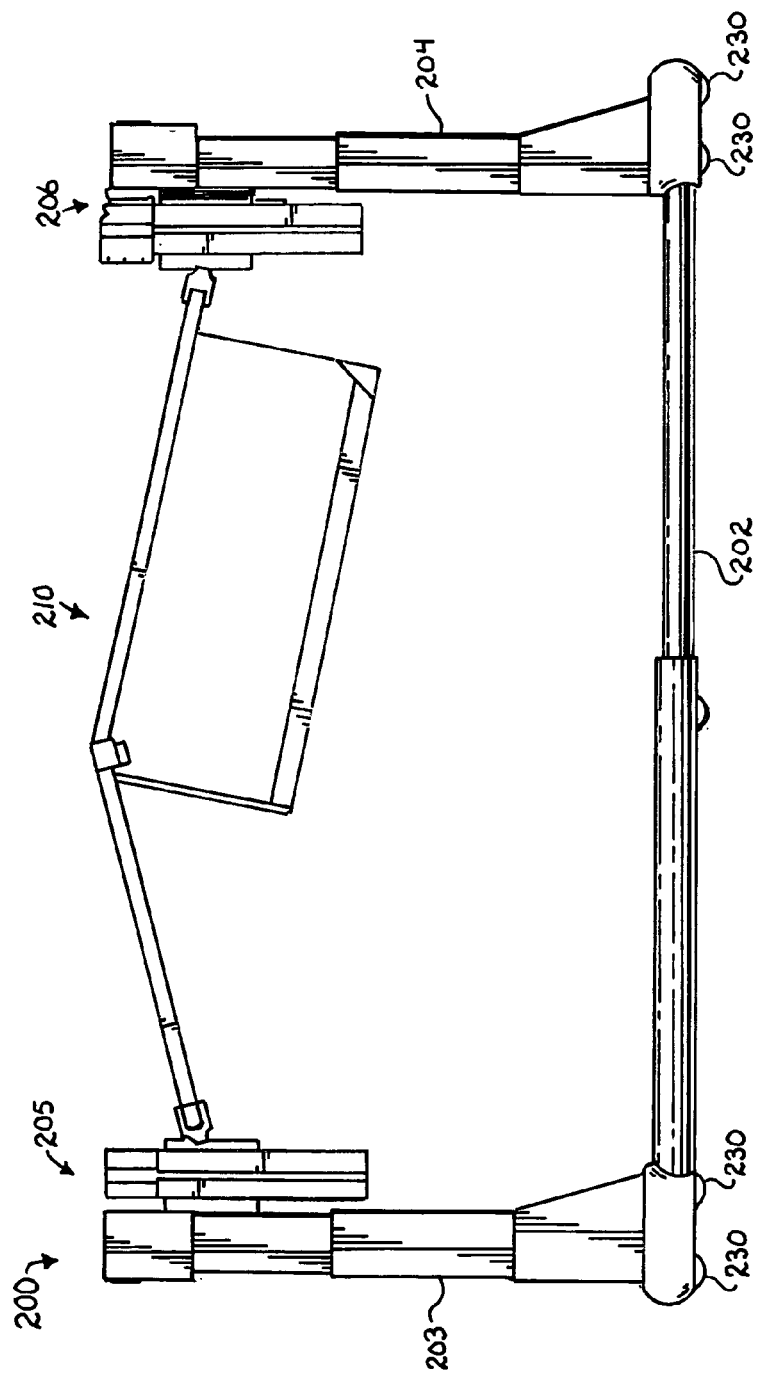

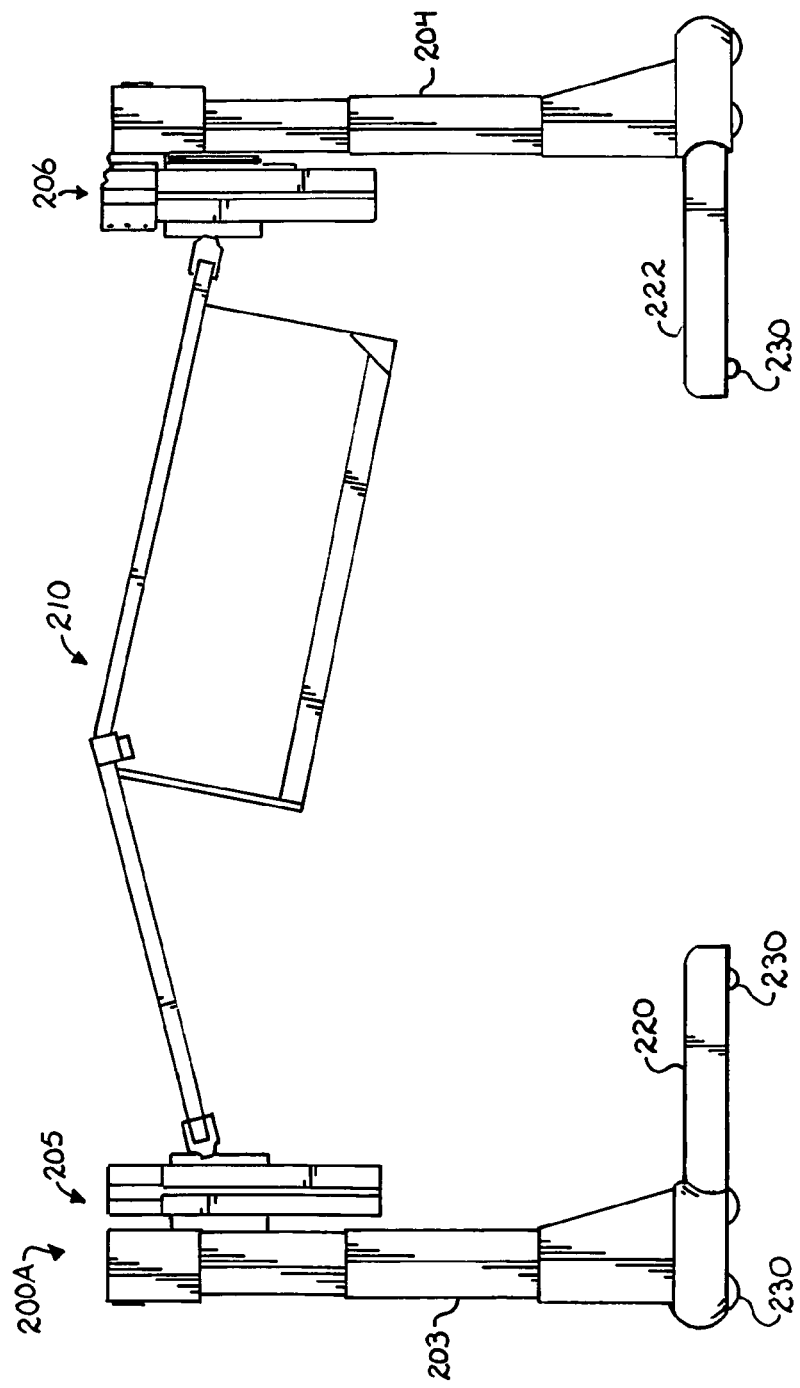

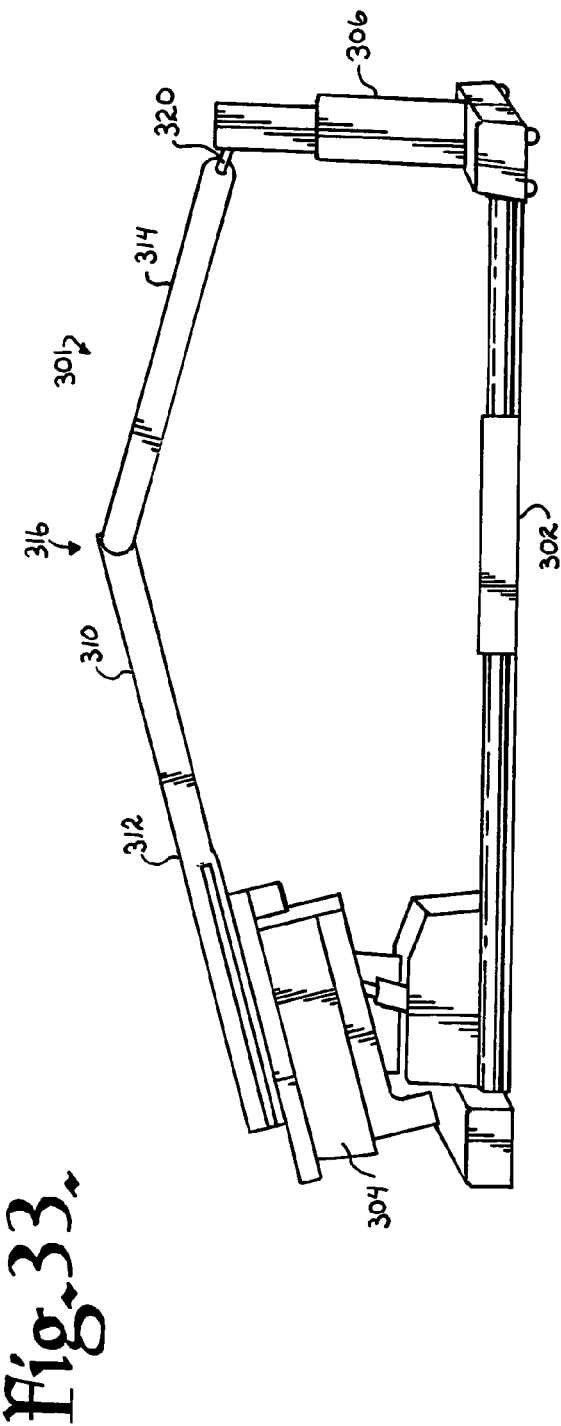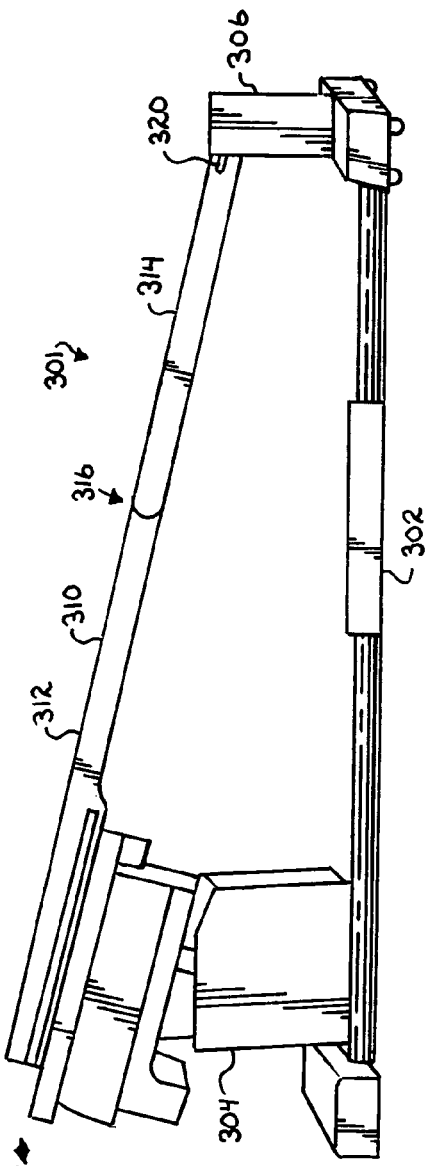

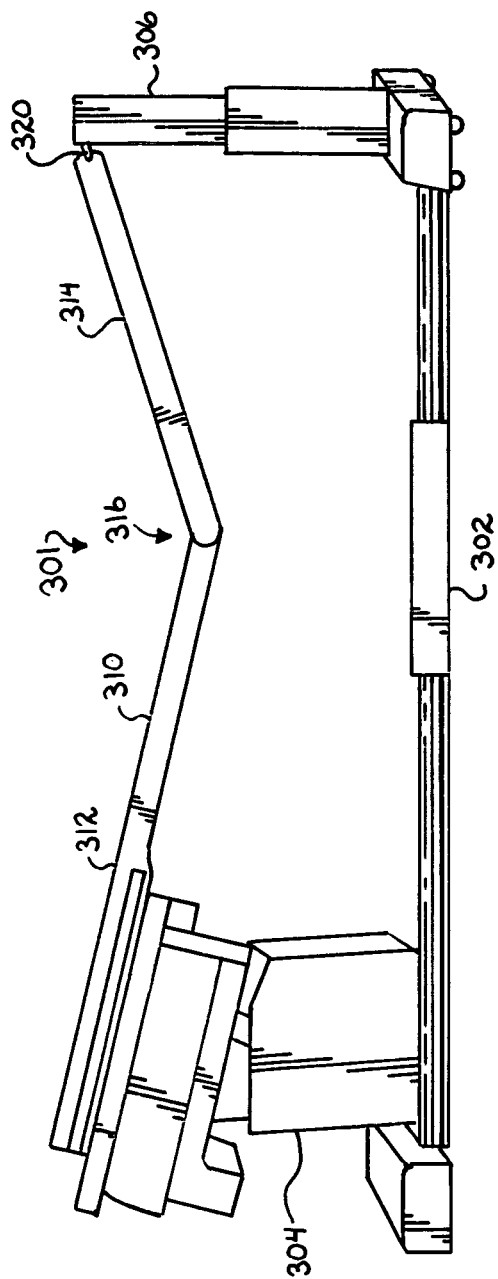

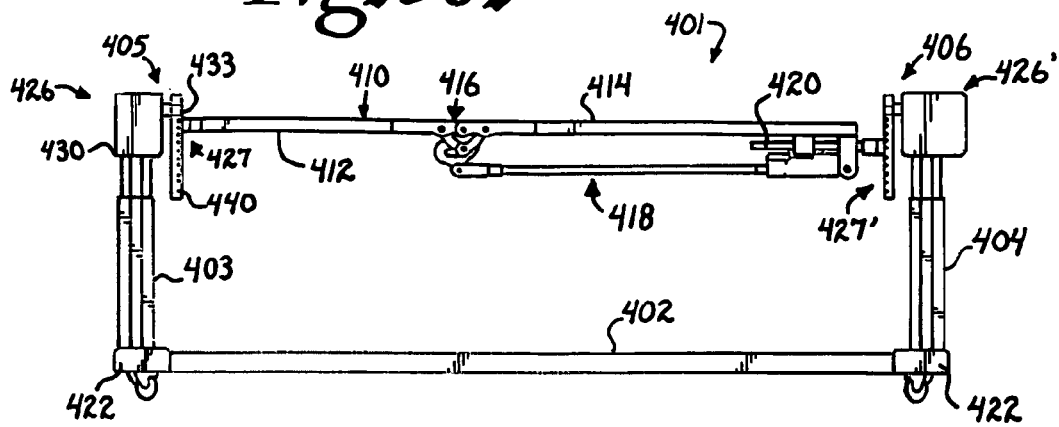
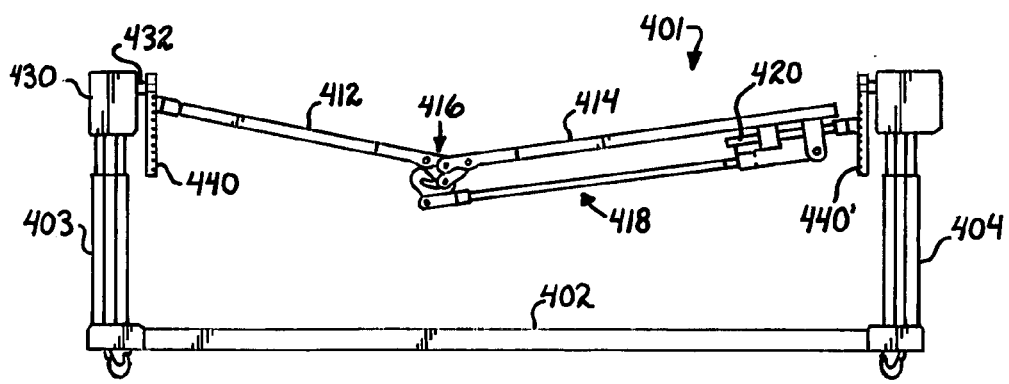
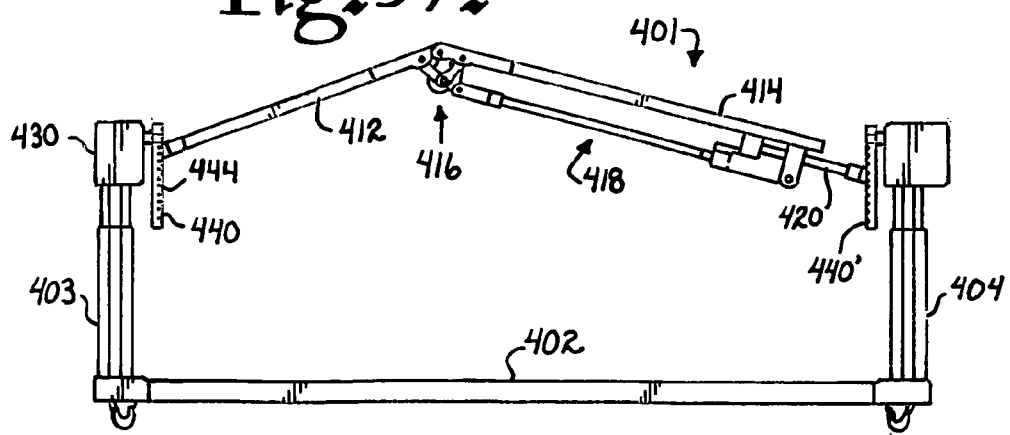

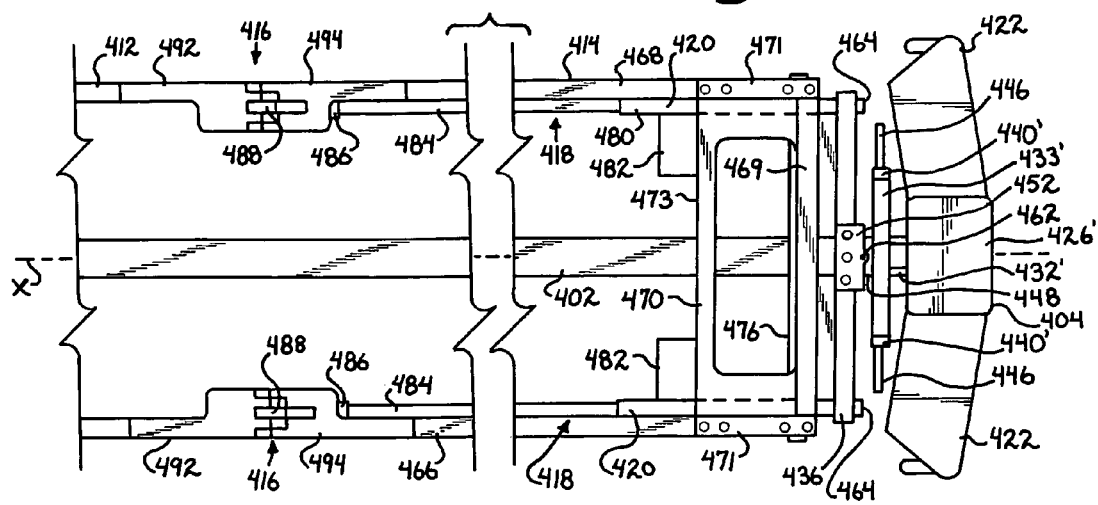
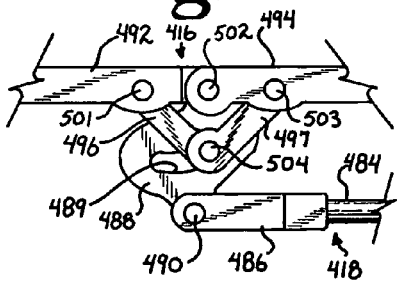
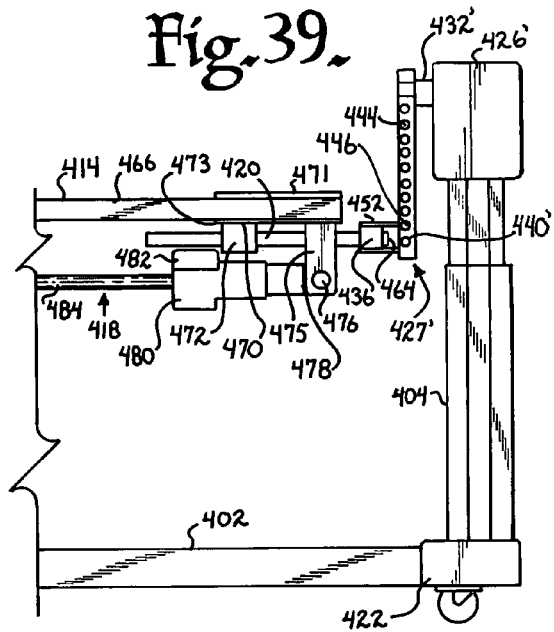

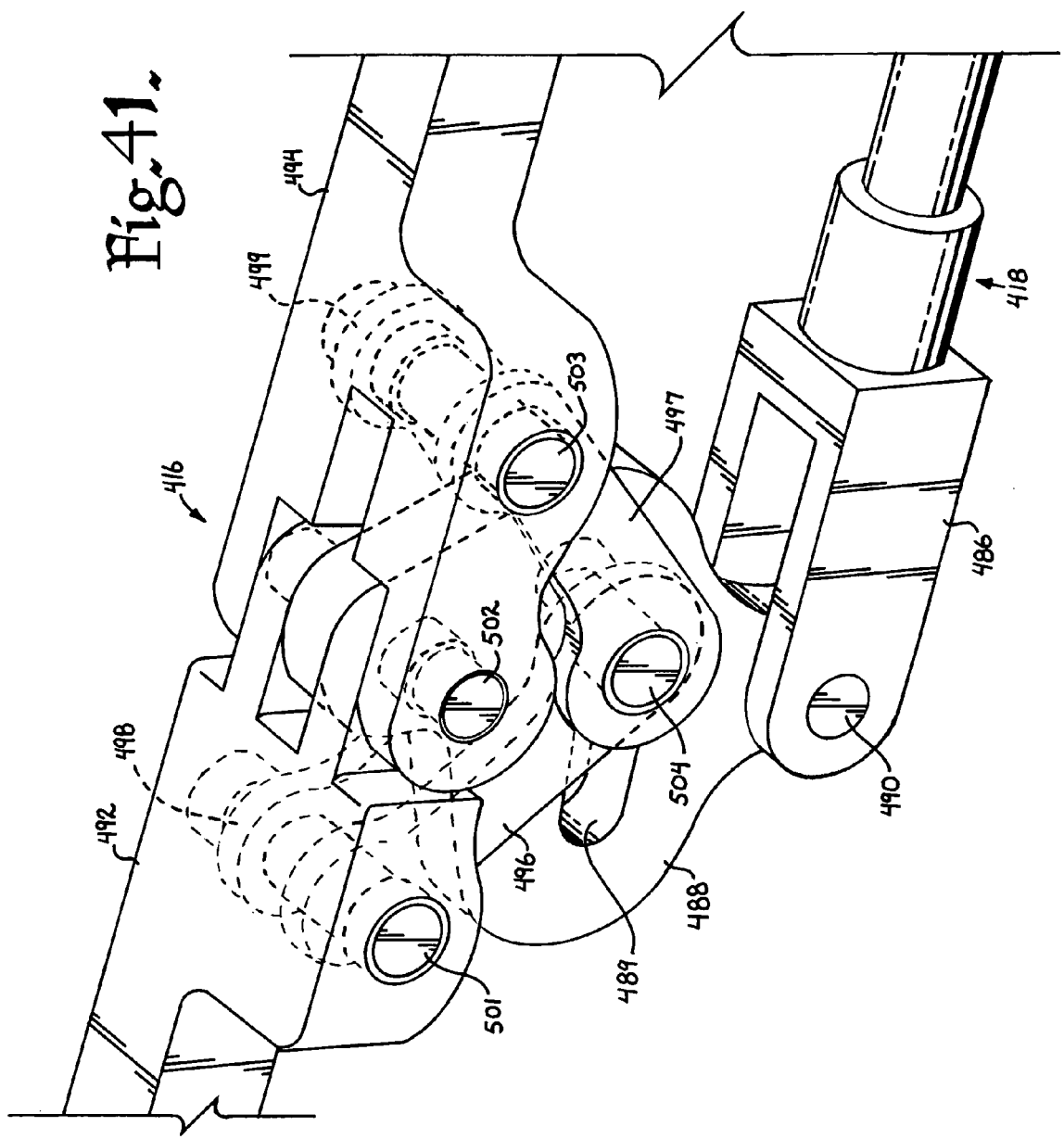

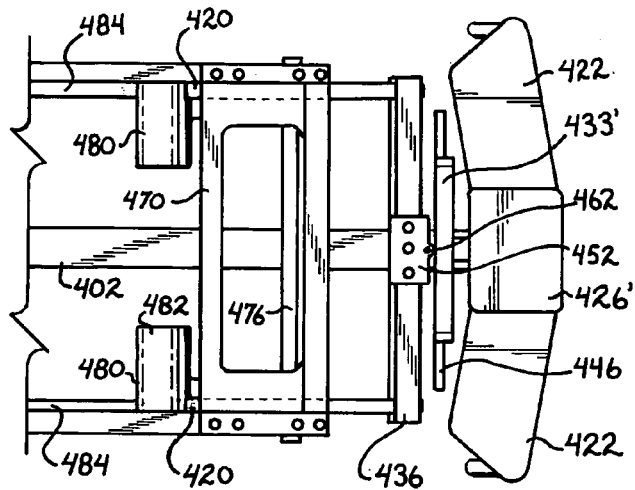
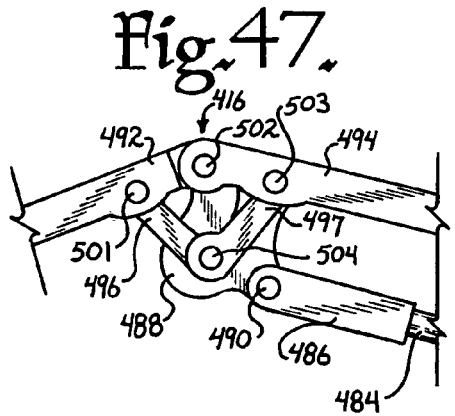
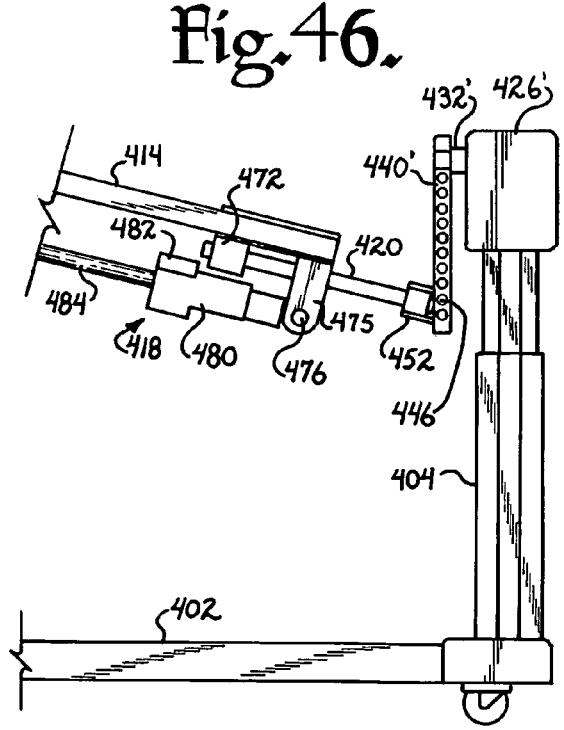

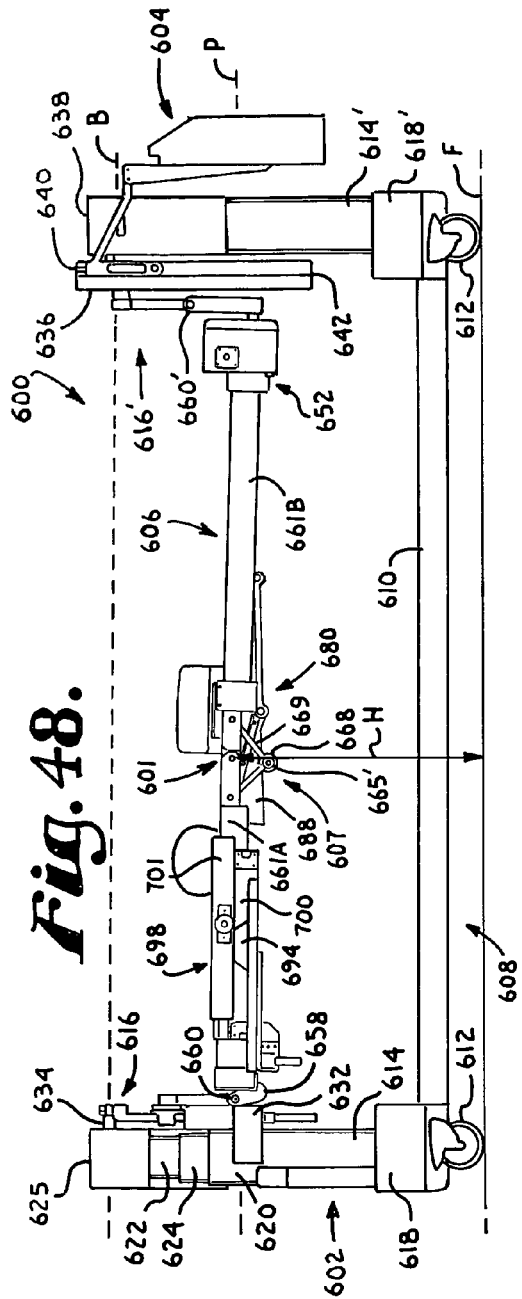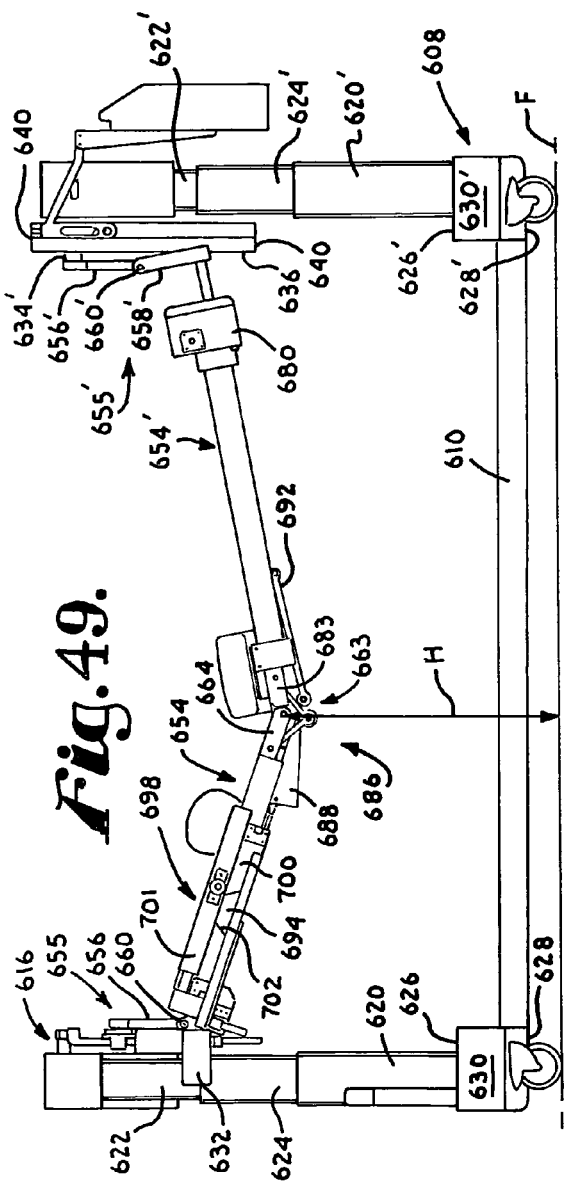

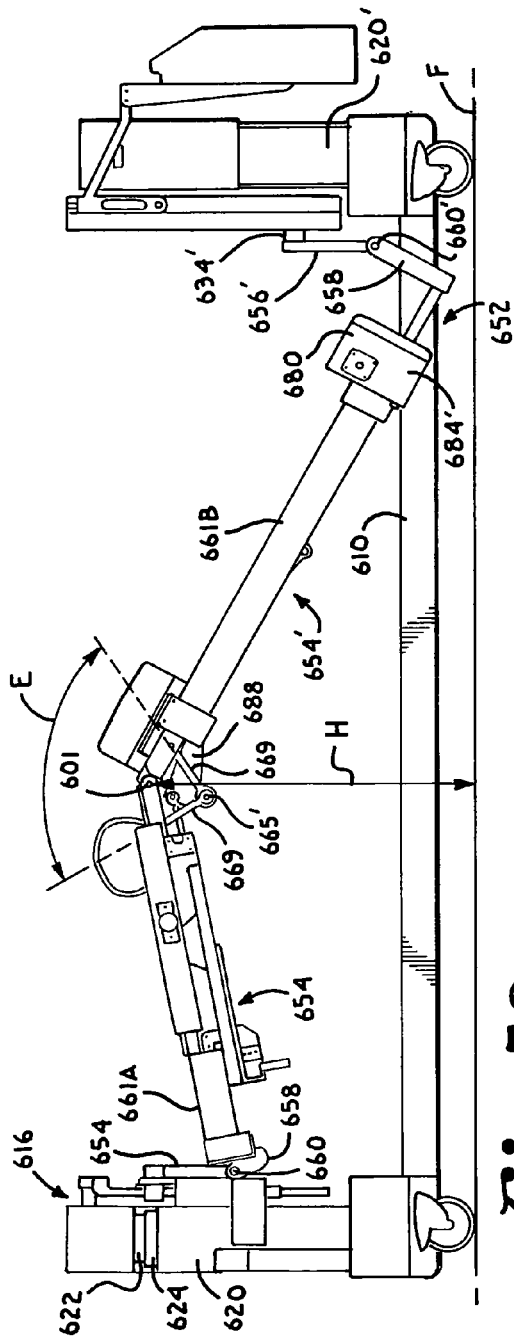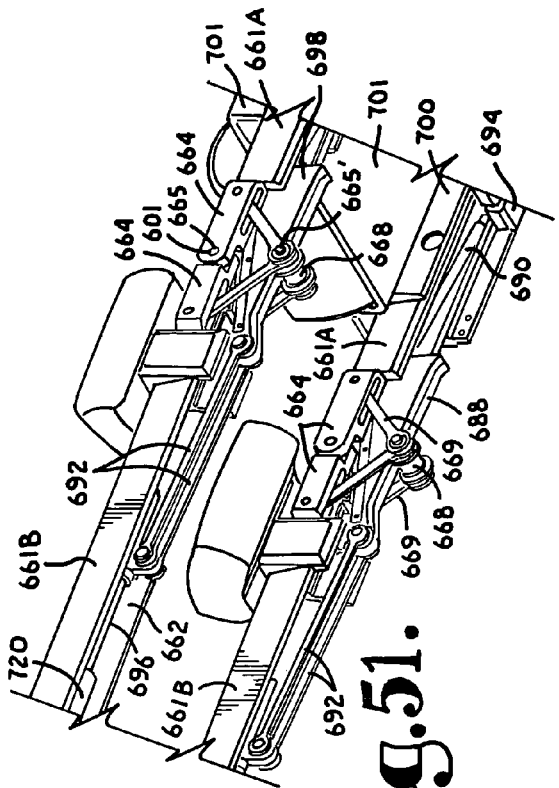

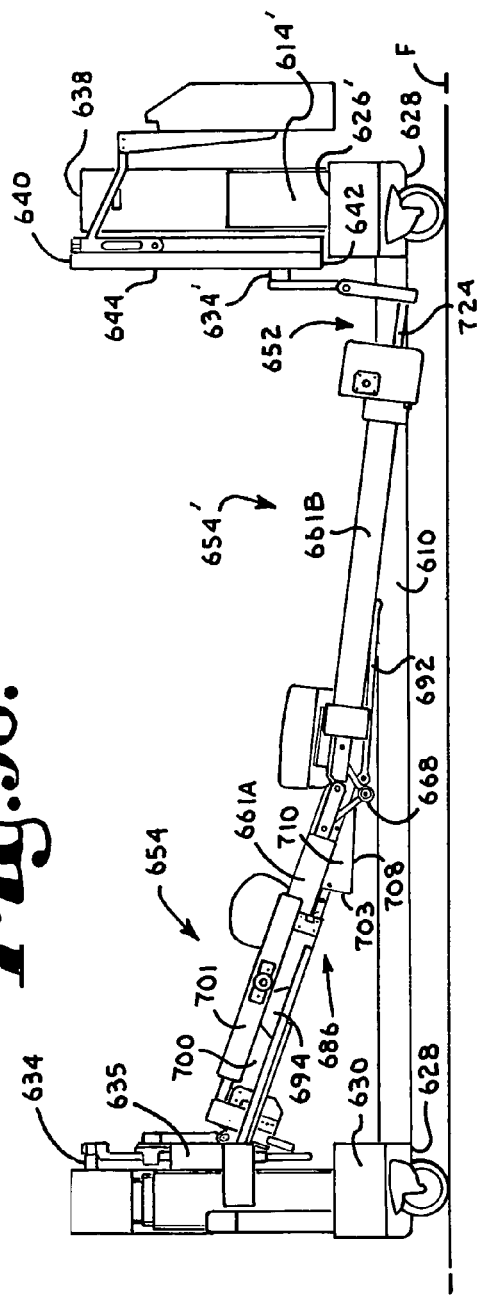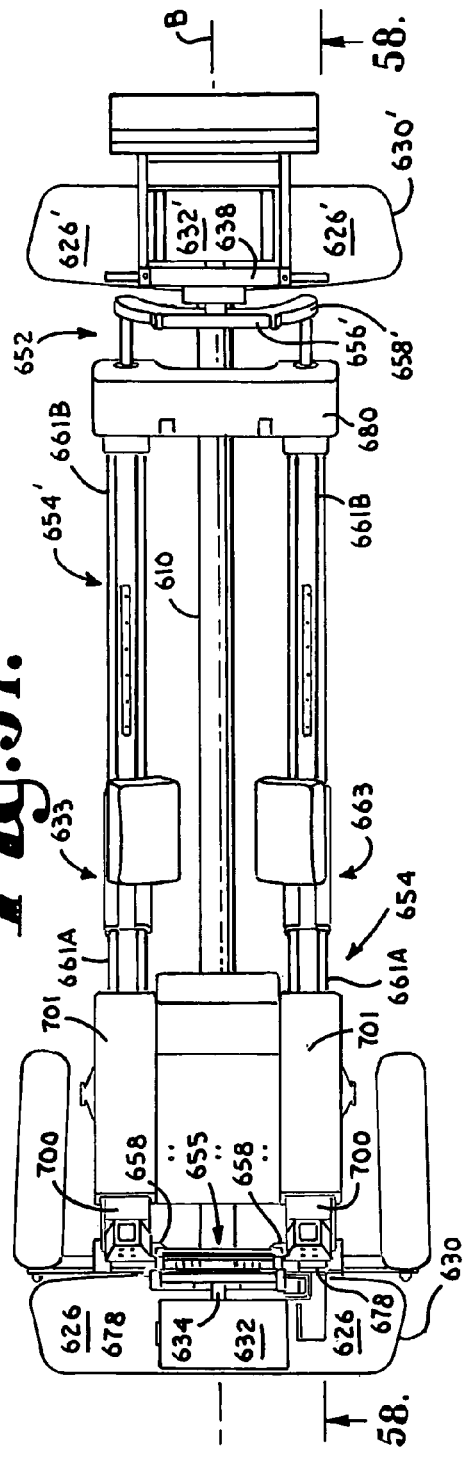

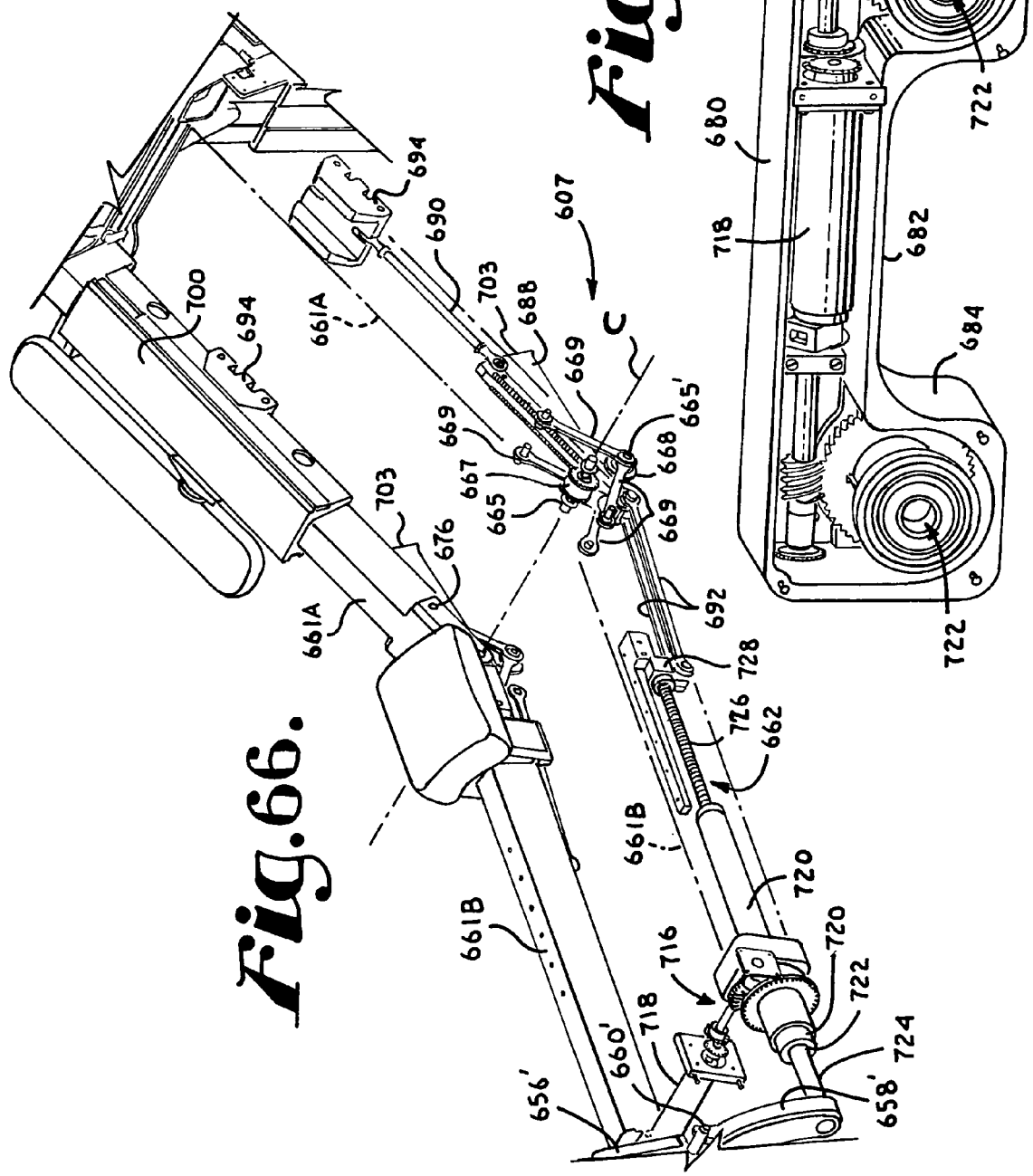

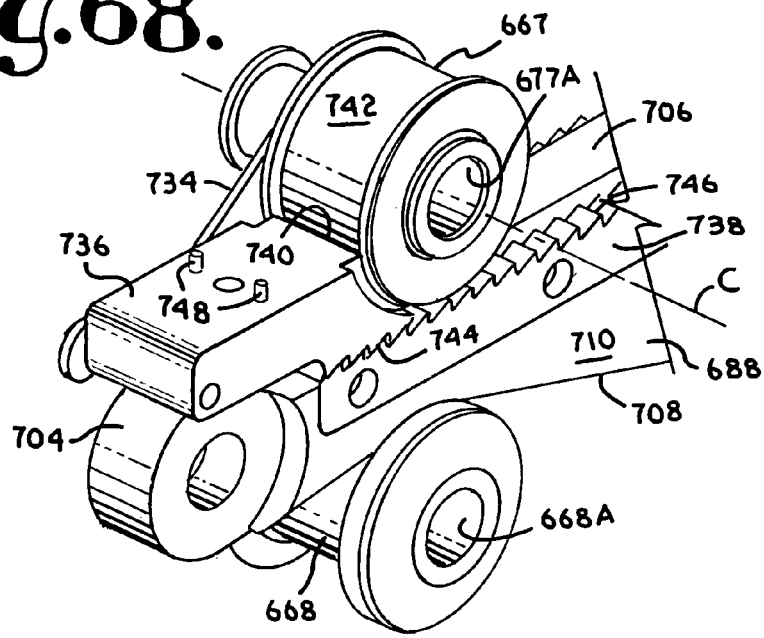
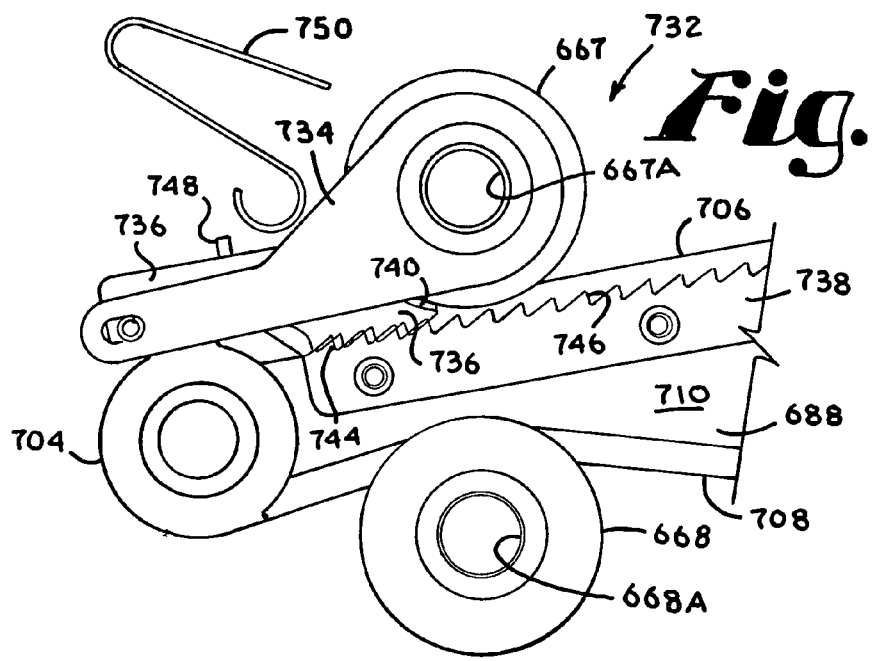

PATIENT POSITIONING SUPPORT STRUCTURE

CROSS REFERENCE TO RELATED APPLICATIONS

This claims the benefit of U.S. Provisional Application No. 61/459,264 filed Dec. 9, 2010, incorporated by reference herein. This application is also a continuation-in-part of U.S. Ser. No. 12/460,702, filed Jul. 23, 2009, now U.S. Pat. No. 8,060,960 and which is a continuation of U.S. Ser. No. 11/788,513, filed Apr. 20, 2007, now U.S. Pat. No. 7,565,708, which further claimed the benefit of U.S. Provisional Application No. 60/798,288 filed May 5, 2006 and was also a continuation-in-part of U.S. patent application Ser. No. 11/159,494 filed Jun. 23, 2005, now U.S. Pat. No. 7,343,635, that is a continuation-in-part of U.S. patent application Ser. No. 11/062,775 filed Feb. 22, 2005, now U.S. Pat. No. 7,152,261, all of which are incorporated by reference herein.

BACKGROUND OF THE INVENTION

The present invention is directed to structure for use in maintaining a patient in a desired position during examination and treatment, including medical procedures such as imaging and surgery and in particular to such a structure that allows a surgeon to selectively position the patient for convenient access to the surgery site and providing for manipulation of the patient during surgery including the tilting, pivoting, angulating or Current surgical practice incorporates imaging techniques and technologies throughout the course of patient examination, diagnosis and treatment. For example, minimally invasive surgical techniques, such as percutaneous insertion of spinal implants, involve small incisions that are guided by continuous or repeated intra-operative imaging. These images can be processed using computer software programs that produce three dimensional images for reference by the surgeon during the course of the procedure. If the patient support surface is not radiolucent or compatible with the imaging technologies, it may be necessary to interrupt the surgery periodically in order to remove the patient to a separate surface for imaging followed by transfer back to the operating support surface for resumption of the surgical procedure. Such patient transfers for imaging purposes may be avoided by employing radiolucent and other imaging compatible systems. The patient support system should also be constructed to permit unobstructed movement of the imaging equipment and other surgical equipment around, over and under the patient throughout the course of the surgical procedure without contamination of the sterile field.

It is also necessary that the patient support system be constructed to provide optimum access to the surgical field by the surgery team. Some procedures require positioning of portions of the patient's body in different ways at different times during the procedure. Some procedures, for example, spinal surgery, involve access through more than one surgical site or field. Since all of these fields may not be in the same plane or anatomical location, the patient support surfaces should be adjustable and capable of providing support in different planes for different parts of the patient's body as well as different positions or alignments for a given part of the body. Preferably, the support surface should be adjustable to provide support in separate planes and in different alignments for the head and upper trunk portion of the patient's body, the lower trunk and pelvic portion of the body as well as each of the limbs independently.

Certain types of surgery, such as orthopedic surgery, may require that the patient or a part of the patient be repositioned during the procedure while in some cases maintaining the sterile field. Where surgery is directed toward motion preservation procedures, such as by installation of artificial joints, spinal ligaments and total disc prostheses, for example, the surgeon must be able to manipulate certain joints while supporting selected portions of the patient's body during surgery in order to facilitate the procedure. It is also desirable to be able to test the range of motion of the surgically repaired or stabilized joint and to observe the gliding movement of the reconstructed articulating prosthetic surfaces or the tension and flexibility of artificial ligaments, spacers and other types of dynamic stabilizers before the wound is closed. Such manipulation can be used, for example, to verify the correct positioning and function of an implanted prosthetic disc, spinal dynamic longitudinal connecting member, interspinous spacer or joint replacement during a surgical procedure. Where manipulation discloses binding, sub-optimal position or even crushing of the adjacent vertebrae, for example, as may occur with osteoporosis, the prosthesis can be removed and the adjacent vertebrae fused while the patient remains anesthetized. Injury which might otherwise have resulted from a "trial" use of the implant post-operatively will be avoided, along with the need for a second round of anesthesia and surgery to remove the implant or prosthesis and perform the revision, fusion or corrective surgery.

There is also a need for a patient support surface that can be rotated, articulated and angulated so that the patient can be moved from a prone to a supine position or from a prone to a 90° position and whereby intra-operative extension and flexion of at least a portion of the spinal column can be achieved. The patient support surface must also be capable of easy, selective adjustment without necessitating removal of the patient or causing substantial interruption of the procedure.

For certain types of surgical procedures, for example spinal surgeries, it may be desirable to position the patient for sequential anterior and posterior procedures. The patient support surface should also be capable of rotation about an axis in order to provide correct positioning of the patient and optimum accessibility for the surgeon as well as imaging equipment during such sequential procedures.

Orthopedic procedures may also require the use of traction equipment such as cables, tongs, pulleys and weights. The patient support system must include structure for anchoring such equipment and it must provide adequate support to withstand unequal forces generated by traction against such equipment.

Articulated robotic arms are increasingly employed to perform surgical techniques. These units are generally designed to move short distances and to perform very precise work. Reliance on the patient support structure to perform any necessary gross movement of the patient can be beneficial, especially if the movements are synchronized or coordinated. Such units require a surgical support surface capable of smoothly performing the multi-directional movements which would otherwise be performed by trained medical personnel. There is thus a need in this application as well for integration between the robotics technology and the patient positioning technology.

While conventional operating tables generally include structure that permits tilting or rotation of a patient support surface about a longitudinal axis, previous surgical support devices have attempted to address the need for access by providing a cantilevered patient support surface on one end. Such designs typically employ either a massive base to counterbalance the extended support member or a large overhead frame structure to provide support from above. The enlarged base members associated with such cantilever designs are problematic in that they can and do obstruct the movement of C-arm and O-arm mobile fluoroscopic imaging devices and other equipment. Surgical tables with overhead frame structures are bulky and may require the use of dedicated operating rooms, since in some cases they cannot be moved easily out of the way. Neither of these designs is easily portable or storable.

Thus, there remains a need for a patient support system that provides easy access for personnel and equipment, that can be easily and quickly positioned and repositioned in multiple planes without the use of massive counterbalancing support structure, and that does not require use of a dedicated operating room.

SUMMARY OF THE INVENTION

The present invention is directed to a patient support system that permits adjustable positioning, repositioning and selectively lockable support of a patient's head and upper body, lower body and limbs in up to a plurality of individual planes while permitting tilting, rotation, angulation or bending and other manipulations as well as full and free access to the patient by medical personnel and equipment. The system of the invention may be cantilevered or non-cantilevered and includes at least one support end or column that is height adjustable. The illustrated embodiments include a pair of opposed independently height-adjustable end support columns. The columns may be independent or connected to a horizontally length-adjustable base. One support column according to the invention may be coupled with a wall mount or other stationary support. A patient support structure is connected to and bridges substantially between the pair of end supports. For example, in an embodiment according to the invention, the patient support structure is hingedly suspended between the end supports.

The patient support structure may be a frame or other patient support that is semi-constrained, having at least first and second hingeable or otherwise joined or connected portions, the first and second portions being selectively lockable in a first substantially planar orientation along a longitudinal axis of the support structure that resembles conventional constrained or fixed patient support structures. However, the hinged or semi-constrained support structure of the invention provides for the first and second portions that are also positionable and lockable in a plurality of angles with respect to one another, with each portion being movable to a position on either side of the first planar orientation. In other words, the patient support structure is capable of hinging or otherwise bending to form an angulation, break or joint, either upwardly or downwardly from a horizontal starting position and also when the support structure is in an inclined or declined position due to one of the support columns raising one end of the structure higher than another end. Furthermore, in addition to an "up" or "down" break, such a break or joint created by the two portions may be oriented from side-to-side, as when the support structure is rotated about a longitudinal axis thereof.

In a particular illustrated embodiment, articulation, jointing or breaking of the patient support structure at a central location between the pair of stationary end supports is supported by a cable drive system (tension band suspension). In another embodiment, a pull-rod assembly supports articulation to control the break or articulation angle and render the patient support structure rigid. Such an embodiment further includes a substantially fixed slider bar disposed at an end of the patient support, the patient support structure being supported by and slidingly movable along such slider bar with the bar following the angle of inclination of the patient support at such end. Other embodiments include cantilevered systems with connected or unconnected movable or telescoping base supports. The first and second patient support structure portions may be in the form of frames, such as rectangular frames or other support structure that may be equipped with support pads for holding the patient, or other structure, such as imaging tops which provide a flat surface.

The patient support structure and the support column or columns are coupled with respective rotation, articulation or angulation adjustment structure for positioning the first support portion with respect to a first column or end support and with respect to the second support portion and the second support portion with respect to the second column or end support. Rotation adjustment structure in cooperation with pivoting and height adjustment structure provide for the lockable positioning of the first and second patient support portions at a variety of selected positions and articulations with respect to the support columns including angulation coupled with Trendelenburg and reverse Trendelenburg configurations as well as providing for patient roll over in horizontal or tilted orientation. Lateral movement (toward and away from a surgeon) may also be provided by a bearing block feature. A pair of patient support structures (such as a support frame and an imaging table) may be mounted between end supports of the invention and then rotated in unison about a longitudinal axis to achieve 180° repositioning of a patient, from a prone to a supine position.

In some embodiments of the invention, primary and secondary elevators are provided, for increasing the amount of angulation of the patient support while simultaneously maintaining the patient's torso in a substantially horizontal position. A failsafe lock may be mounted in the angulation subassembly to lock the position of the patient support in the event of catastrophic failure of the patient support structure. Movement of the patient's torso in concert with changes in angulation are provided by linkage of the angulation subassembly with a cephalad and caudal slidable torso support structure.

OBJECTS AND ADVANTAGES OF THE INVENTION

Therefore, it is an object of the present invention to overcome one or more of the problems with patient support systems described above. Further objects of the present invention include providing breaking or hinged patient support structures; providing such structures wherein such break or joint may be in any desired direction; providing such structures that include at least one base support structure that allows for vertical height adjustment; providing such a structure wherein such base support is located at an end of the patient support, allowing for patient positioning and clearance for access to the patient in a wide variety of orientations; providing such a structure that may be rotated about an axis as well as moved upwardly or downwardly at either end thereof; providing such structure for cooperatively continuously and non-segmentedly changing the height and angulation of the patient support while moving the patient's torso so as to prevent excessive extension and compression of the patient's spinal column; providing such structure for maintaining the height of the point of angulation of the patient while simultaneously changing the amount of angulation thereof; and providing apparatus and methods that are easy to use and especially adapted for the intended use thereof and wherein the apparatus are comparatively inexpensive to make and suitable for use.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is a perspective view of a patient support structure according to the invention.

FIG. 2 is an enlarged and partial side elevational view of a portion of the support structure of FIG. 1.

FIG. 3 is an enlarged and partial top plan view of the support structure of FIG. 1.

FIG. 4 is an enlarged and partial perspective view of a portion of the structure of FIG. 1.

FIG. 5 is an enlarged and partial side elevational view of a portion of the structure of FIG. 1.

FIG. 6 is an enlarged and partial perspective view of a portion of the structure of FIG. 1.

FIG. 7 is an enlarged and partial perspective view of a first hinge of the structure of FIG. 1.

FIG. 8 is an enlarged and partial perspective view of a cooperating second hinge of the structure of FIG. 1.

FIG. 12 is an enlarged and partial perspective view of a portion of the structure of FIG. 1 showing a cable drive motor and winch cylinders.

FIG. 13 is a partial perspective view of a patient support frame of the structure of FIG. 1.

FIG. 14 is a partial perspective view of a patient imaging top for replacement with the patient support frame of FIG. 13.

FIG. 15 is a reduced perspective view of the structure of FIG. 1 shown with an imaging top of FIG. 14 replacing the support frame of FIG. 13 and shown in a planar inclined position.

FIG. 16 is a perspective view of the structure of FIG. 15 shown in a planar tilted position.

FIG. 17 is a perspective view of the structure of FIG. 15 shown in a planar inclined and tilted position.

FIG. 25 is a is a perspective view of a second embodiment of a patient support structure according to the invention including a patient support frame and an imaging table shown in a first spaced orientation.

FIG. 26 is a perspective view of the patient support structure of FIG. 25 shown tilted in an intermediate position during a rotation as would be used for a patient rollover.

FIG. 27 is a perspective view of the structure of FIG. 25 shown further tilted in a second intermediate position during rotation.

FIG. 28 is a perspective view of the structure of FIG. 25 shown after rotation to a final flipped position.

FIG. 29 is a perspective view similar to FIG. 25 showing the patient support frame and the imaging table in a second spaced orientation.

FIG. 30 is a front elevational view of a third embodiment of a patient support structure according to the invention.

FIG. 31 is a front elevational view of a fourth embodiment of a patient support structure according to the invention.

FIG. 32 is a perspective view of a fifth embodiment of a patient support structure according to the invention shown in a planar inclined position.

FIG. 33 is a perspective view of the structure of FIG. 32 shown in an inclined and upward breaking position.

FIG. 34 is a perspective view of the structure of FIG. 32 shown in a substantially symmetrical downward breaking position.

FIG. 35 is a reduced side elevational view of a sixth embodiment of a patient support structure according to the invention shown in a substantially horizontal and planar position.

FIG. 36 is a reduced side elevational view of the structure of FIG. 35 shown in a symmetrical downward breaking position.

FIG. 37 is a reduced side elevational view of the structure of FIG. 35 shown in a symmetrical downward breaking position.

FIG. 38 is an enlarged and partial top plan view of a portion of the structure of FIG. 35 and shown in the same position as shown in FIG. 35.

FIG. 39 is an enlarged and partial side elevational view of the structure of FIG. 35 and shown in the same position as shown in FIG. 35.

FIG. 40 is an enlarged and partial side elevational view of the structure of FIG. 35 and shown in the same position as shown in FIG. 35.

FIG. 41 is an enlarged and partial perspective view of the structure shown in FIG. 40.

FIG. 45 is an enlarged and partial top plan view of a portion of the structure of FIG. 35 and shown in the same position as shown in FIG. 37.

FIG. 46 is an enlarged and partial side elevational view of the structure of FIG. 35 and shown in the same position as shown in FIG. 37.

FIG. 47 is an enlarged and partial side elevational view of the structure of FIG. 35 and shown in the same position as shown in FIG. 37.

FIG. 48 is a side elevational view of another embodiment of the patient support structure according to the invention, shown in a substantially horizontal and planar position:

FIG. 49 is a side elevation view of the patient support structure of FIG. 48, shown in a downward breaking position and in a fully elevated position.

FIG. 50 is a side elevation view of the patient support structure of FIG. 48, shown in an upward breaking position and in a fully lowered position.

FIG. 51 is an enlarged bottom perspective view of a portion of the patient support structure of FIG. 48, and shown in the same position as shown in FIG. 48.

FIG. 56 is a side perspective view of the patient support structure of FIG. 52, shown in a downward breaking position and a fully lowered position.

FIG. 57 is an enlarged top elevational view of the patient support structure of FIG. 48, shown in the same position as shown in FIG. 49.

FIG. 66 is an enlarge perspective view of the patient support subassembly of the patient support structure of FIG. 48 with portions broken away and portions shown in phantom to show detail thereof.

FIG. 67 is an enlarged perspective view of the gearbox of the patient support structure of FIG. 48 with portions removed to show detail thereof.

FIG. 68 is an enlarged partial perspective view of portions of the tensioned angulation subassembly of the patient support structure of FIG. 48, including the upper and lower rollers and failsafe structure.

FIG. 69 is an enlarged partial side view of portions of the tensioned angulation subassembly of the patient support structure of FIG. 48, including the upper and lower rollers and failsafe structure.

DETAILED DESCRIPTION OF THE ILLUSTRATED EMBODIMENTS

Figure 9:
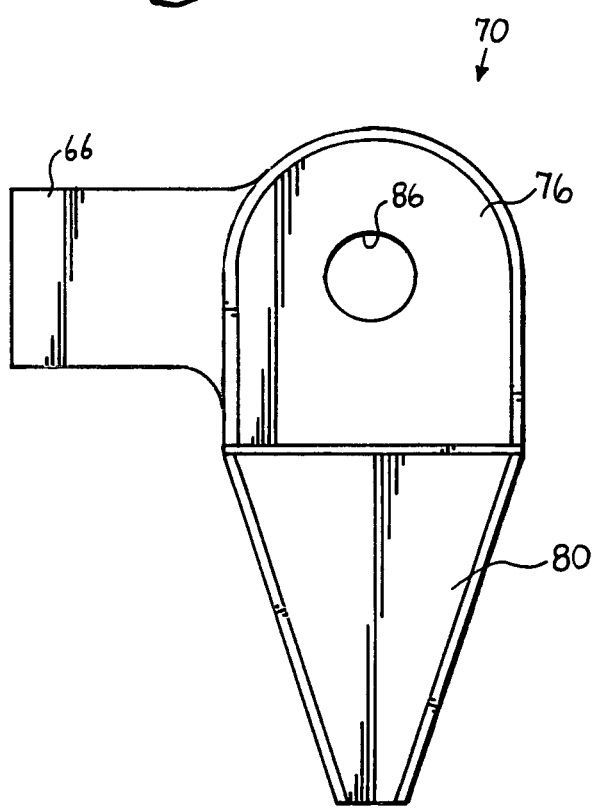
FIG. 9 is an enlarged and partial elevational view of the hinge of FIG. 7.
Figure 10:
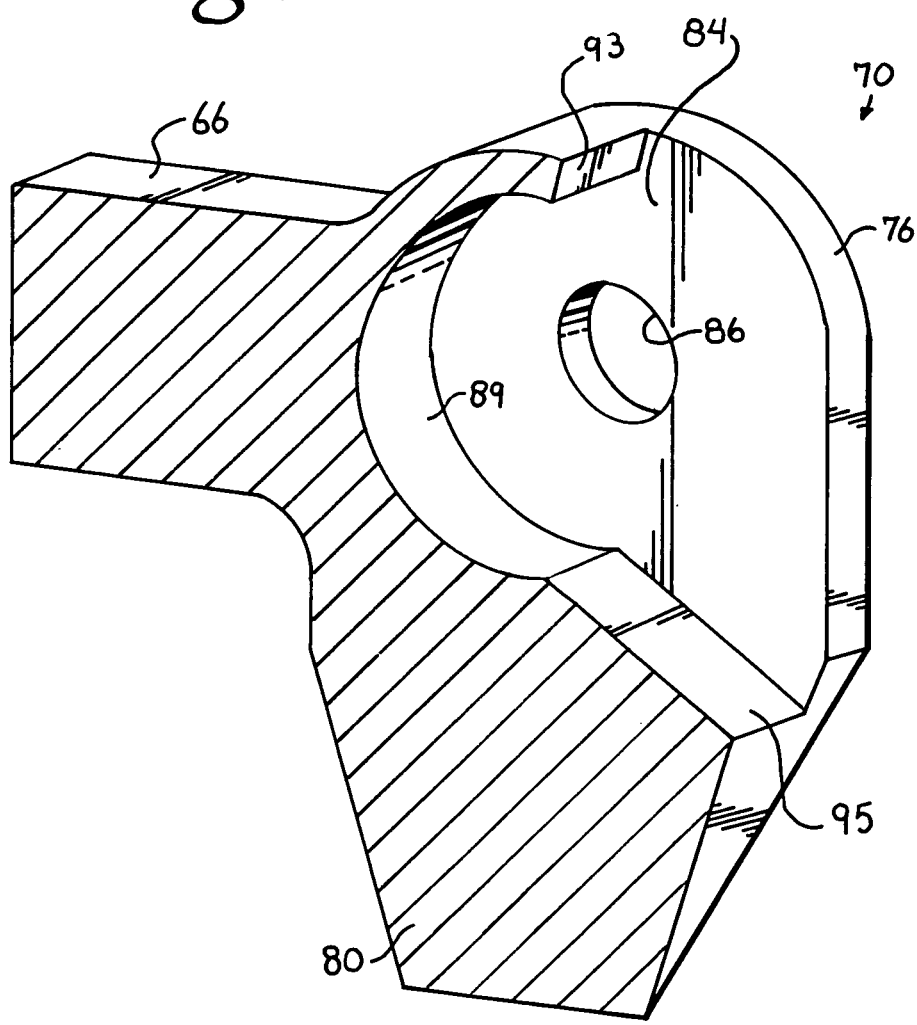
FIG. 10 is an enlarged and partial perspective view of an outer portion of the hinge of FIG. 7 with portions broken away to show the detail thereof.
Figure 11:
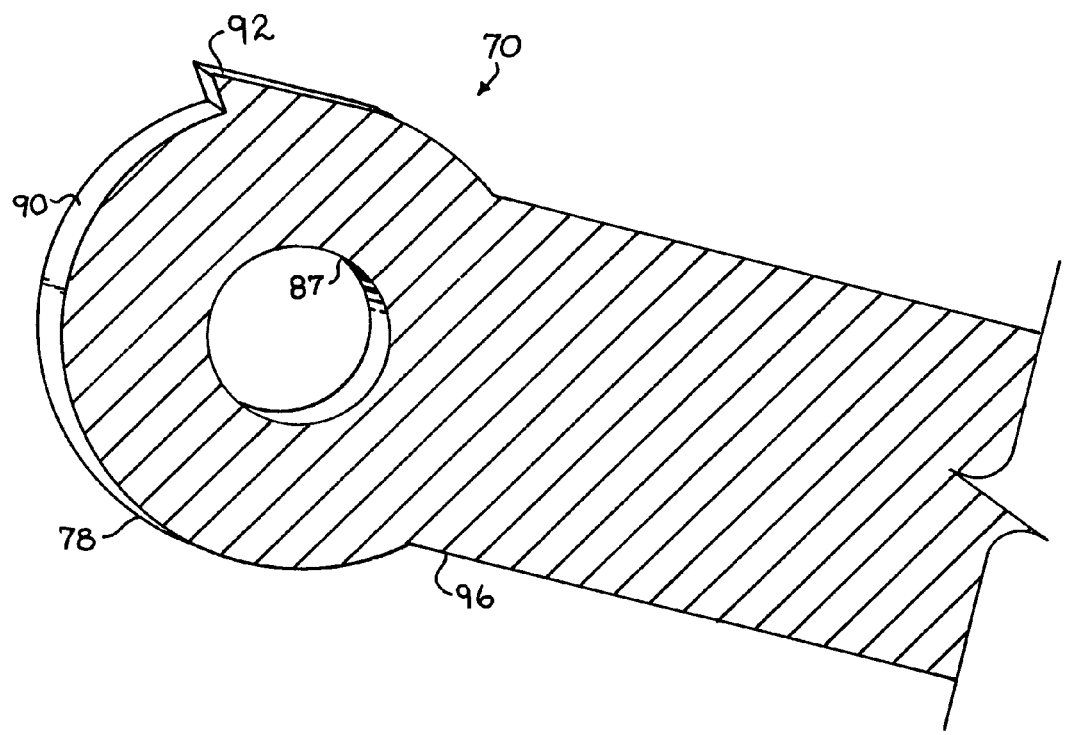
FIG. 11 is an enlarged and partial perspective view of an inner portion of the hinge of FIG. 7 with portions broken away to show the detail thereof.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring now to the drawings, a patient positioning support structure according to the invention is generally designated by the reference numeral 1 and is depicted in FIGS. 1-12. The structure 1 includes first and second upright support piers or columns 3 and 4 which are illustrated as independent, stationary floor base support structures as shown in FIG. 1 or may be connected to one another by a non-telescoping base support as illustrated in the embodiment shown in FIGS. 25-28. In some embodiments according to the invention as shown, for example, in FIGS. 32-34, the base connection places the columns in a selectively telescoping relationship. It is also foreseen that in certain embodiments according to the invention, one of the support columns may be replaced by a conventional operating room table, or may even be a wall mount. In the first illustrated embodiment, the upright support column 3 is connected to a first support assembly, generally 5, and the upright support column 4 is connected to a second support assembly, generally 6. Between them, the support assemblies 5 and 6 uphold a removable elongate, articulate jointed or breaking patient holding or support structure, generally 10 and optionally, a second removable patient support structure that will be described with respect to another embodiment of the invention. The illustrated support structure 10 includes a first frame section 12, a second frame section 14 with a transverse support cross bar 15, and a pivot or hinge assembly, generally 16. In the illustrated embodiment, the pivot assembly further includes a cable drive system including a dual winch 18 and cooperating cables 20.

The columns 3 and 4 are supported by outwardly extending feet 22 that may or may not include spaced apart casters or wheels (not shown) each equipped with a floor-lock foot lever for lowering the feet 12 into a floor-engaging position as shown in FIG. 1. The columns 3 and 4 each include two or more telescoping lift arm segments 3a, 3b and 4a, 4b, respectively that permit the height of each of the columns 3 and 4 to be selectively increased and decreased in order to raise and lower all or a selected portion of the connected patient support structure 10. It is foreseen that the vertical supports 3 and 4 may be constructed so that the column 3 has a greater mass than the support column 4 or vice versa in order to accommodate an uneven weight distribution of the human body. Such reduction in size at the foot end of the system 1 may be employed in some embodiments to facilitate the approach of personnel and equipment.

Each of the support assemblies 5 and 6 generally includes a rotation subassembly 26 and 26' and an angulation subassembly 27 and 27', respectively, that are interconnected as will be described in greater detail below and include associated power source and circuitry linked to a controller 29 (FIG. 1) for cooperative and integrated actuation and operation. The rotational subassemblies 26 and 26' enable coordinated rotation of the patient support structure 10 about a longitudinal axis of the structure 1. The angulation subassemblies 27 and 27' shown in FIGS. 2 and 3 enable the selective hinging, articulation or breaking of the support 10 at the hinge assembly 16 at desired levels and increments as well as selective tilting of the frame portions 12,14 with respect to a longitudinal axis of such frame portion.

The rotation subassembly or mechanism 26, shown in FIGS. 1 and 5, includes at least one motor housing 30 surmounting the support column 3. In the illustrated embodiment, only one rotational motor is provided, but it is foreseen that a cooperating motor may also be mounted on the support column 4. A main rotational shaft 32 extends from the motor housing 30 that turns a rotation structure 33. The rotation structure 33 in turn rotates the connected patient support 10 about a longitudinal axis as will be described in greater detail below. The motor housing 30 contains a rotary electric motor or other actuator drivingly engaged with the shaft 32. The rotation mechanism 26 is operated by actuating the motor using a switch or other similar means. The rotation structure 33 is fixed to the shaft 32 at a location spaced from the motor housing 30 and the support column 3 to provide clearance for rotation of the connected patient support structure 10.

As shown in FIGS. 4 and 5, the rotation structure 33 is attached to a pair of translation posts or H-bar posts 40 disposed at either end of the rotation structure 33. The posts 40 are each attached to the structure 33 by a pin 42, bolt, or other fixing structure. A plurality of cooperating apertures 44 formed in the posts 40 provide passageway for a pivot pin 46 to extend therethrough. The pivot pin 46 is receivable in each cooperating pair of apertures 44 allowing for selective placement of a translation connector 48 that is sized and shaped to be received between the pair of posts 40 and also receive the pivot pin 46 therethrough. The pin 46 and connector 48 are thus positionable in an orientation transverse to the longitudinal extension of the support 10 at a variety of heights to be selected by the surgeon and readily changeable, even during surgery if necessary, to vary the height of the frame section 12. The multiple location or height feature is also advantageous when more than one frame or patient structure is mounted in tandem as shown, for example in FIGS. 25-29. The position of the frame or other structure may be desirably changed to provide close proximity to an imaging top with a distance between a patient support and an imaging top being expandable or reduceable depending upon the size or other attributes of a patient and surgical or other requirements. As illustrated in FIG. 5, the connector 48 has a slot 50 for receiving the pivot pin 46.

Also with reference to FIGS. 4 and 5, the translation connector 48 is in turn attached to a pivot connector 52. The pivot connector 52 includes first and second outwardly opening and opposed slots 54 and 56. The first slot 54 is sized and shaped for receiving the translation connector 48 and the second slot is sized and shaped for receiving an end connection 58 of the frame section 12. The pivot connector 52 further includes a through aperture or bore 60 running substantially perpendicular to the slot 54 and communicating therewith. The aperture 60 is sized and shaped to receive a pivot pin 62 therethrough. The connector 48 also includes a through bore 60' that receives the pivot pin 62. The swivelable connection provided by the pin 62 allows for some forward and rearward lateral movement of the attached frame end connection 58 and thus the frame section 12, providing a degree of freedom and clearance needed for rotation the patient support about a longitudinal axis of a patient. The slot 56 is sized and shaped to frictionally engage the frame end connection 58, thus securely fixing the end connection 58 to the pivot connector 52. The frame end connection 58 is in turn fixed to each of elongate frame members 66 and 68 of the frame section 12. The frame members 66 and 68 are each hingedly connected to the hinge assembly 16 to be described in greater detail below. Pivoting of the translation connector 48 with respect to the pin 46 provides for selected articulation of the frame section 12 (that includes the end connection 58 and the frame members 66 and 68) and/or the entire support 10 with respect to the support pier or column 3.

With reference to FIG. 6, at the support pier or column 4, the support assembly 6 is substantially similar to the support assembly 5 with the exception that the rotation subassembly 26' can be passive and, therefore, not include a motor. However, the support pier or column 4 preferably includes a powered mechanism to provide selective height adjustment of the subassembly 26'. A rotation structure 33' is spaced from and freely rotatable with respect to the column 4. The structure 33' includes a shaft (not shown) extending outwardly therefrom similar to the rotation shaft 32, the shaft being rotatingly received in an aperture in the support column 4.

The rotation subassembly 26' and the angulation subassembly 27' otherwise include elements identical to or substantially similar to the elements of the subassemblies 26 and 27. Specifically, H-bar posts 40', pin 42', apertures 44', pivot pin 46', translation connector 48', slot 50', pivot connector 52', end connector 58' and pivot pin 62', are identical or substantially similar in form and cooperate with other elements identically or substantially similarly to what has been described previously herein with respective H-bar posts 40, pin 42, apertures 44, pivot pin 46, translation connector 48, slot 50, pivot connector 52, end connector 58 and pivot pin 62.

The frame 14 further includes frame members 66' and 68' that are each fixed to the end connector 58'. The frame members 66' and 68' are pivotally or hingedly connected to respective frame members 66 and 68 by the hinge assembly 16. Specifically, the frame member 66 is attached to the frame member 66' by the hinge mechanism 70 and the frame member 68 is attached to the frame member 68' by the hinge mechanism 72.

Figure 21:
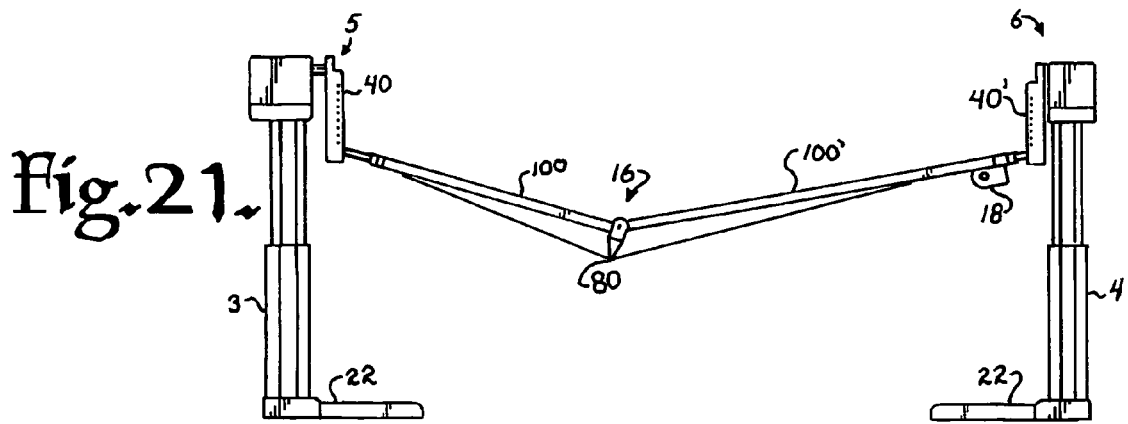
FIG. 21 is a side elevational view of the structure of FIG. 15 shown in a symmetrical downward breaking position.

With particular reference to FIGS. 3, 7 and 9-11, the hinge mechanism 70 includes an outer member 76 and an inner member 78. The outer member 76 is fixed or may be integral with the elongate frame member 66, while the inner member 78 is integral or otherwise fixed to the frame member 66'. The outer member 76 further includes an extension 80 with a groove 82 for receiving and guiding the cable 20. The extension 80 tapers in a direction from the outer member interior 84 to the groove 82. The extension 80 is configured to cause a slight upward break or bend of the support 10 when the extension 80 comes into contact with the cable 20 at the groove 82. In that way, when the cables 20 are reeled in to shorten the hypotenuse of the triangle formed by the cable, the section 12 and the section 14, the sections 12 and 14 move toward one another, resulting in the upward break as illustrated, for example, in FIG. 18. The downward break or joint illustrated, for example, in FIG. 21 is a result of lengthening the cable 20 distance and allowing gravity to drop the hinge 70. The extension 80 is shaped to extend slightly inwardly toward a longitudinal axis A of the support 10, thereby guiding the cable 20 along a path within a periphery of the frame sections 12 and 14 when the extension 80 is in contact with the cable 20 when in a downward breaking configuration directed toward the cable with the cable 20 being received at the groove 82.

It is foreseen that if an exclusively upward breaking or jointing embodiment is desired according to the invention, the sections 12 and 14 may be positioned with respect to two end columns to always include a slight upward break, joint or bend at the hinge or pivot between the sections 12 and 14. When the telescoping base is actuated to move the columns toward one another, the sections 12 and 14 would automatically further break or articulate upwardly and toward one another. Downward breaking or jointing would not be possible in such an embodiment as the maximum distance between the two end columns would still ensure a slight upward break or hinge between the sections 12 and 14. Such an embodiment would be acceptable for use because patient holding pads could be positioned on the frames 12 and 14 such that the patient would be in a substantially horizontal position even when there is a slight upward bend or break at the hinge between the sections 12 and 14.

Returning to the hinge 70 of illustrated embodiment, the inner member 78 is slidingly and rotatably receivable in an interior 84 of the outer member 76. The outer member has a pair of pivot apertures 86 and the inner member has a pivot aperture 87, the apertures cooperating to create a through bore for receiving a pivot pin 88 through both the inner and outer hinge members. The interior 84 includes a curved partially cylindrical surface 89 for slidingly receiving a cooperating outer rounded and partially cylindrical surface 90 of the inner member 78. The inner member 78 further includes a downward breaking stop or projection 92 that limits a downward pivot (in a direction toward the cables 20) of the hinge 70 in the event the cables 20 should fail. The stop 92 abuts against a surface 93 of the interior 84. In the illustrated embodiment, the stop 92 limits the extent of rotation or hinging of the section 66 with respect to the section 66' to about twenty-five degrees. Upward pivot (in a direction away from the cables 20) is limited by abutment of an inner planar surface 95 with a planar surface 96 of the hinge inner member 78.

With particular reference to FIG. 8, the hinge mechanism 72 is substantially a mirror image of the hinge mechanism 70 and therefore includes the following elements: a hinge outer member 76', an inner member 78', an extension 80' with a groove 82', an interior 84', pivot apertures 86', a pivot pin 88', a curved surface 89'(not shown), an outer surface 90' (not shown), a stop 92' (not shown), an abutment surface 93', an inner planar surface 95' and a planar surface 96' that are identical or substantially similar in shape and function to the respective hinge outer member 76, inner member 78, extension 80, groove 82, interior 84, pivot apertures 86, pivot pin 88, curved surface 89, outer surface 90, stop 92, abutment surface 93, inner planar surface 95 and planar surface 96 described herein with respect to the hinge 70.

It is noted that other hinge or pivot mechanisms may be utilized in lieu of the hinge assembly 16. For example, the polyaxial joint 95 illustrated and described in Applicant's U.S. Pat. No. 7,152,261 and pending U.S. patent application Ser. No. 11/159,494 filed Jun. 23, 2005, may be incorporated into the patient support structure 10 at the break or joint between the sections 12 and 14. The disclosures of U.S. Pat. No. 7,152,261 and U.S. patent application Ser. No. 11/159, 494 are incorporated by reference herein. It is foreseen that a rotating universal joint operated type of hinge mechanism could be used with the invention, etc.

With particular reference to FIGS. 6 and 12, the cable drive system 18 includes a rotary motor 98 cooperating with and driving by rotation a pair of winch cylinders 99 disposed on either side of the motor 98. The motor 98 and cylinders 99 are mounted to the end connector 58' located near the support column 4. Each cable 20 is attached to one of the winch cylinders 99 at one end thereof and to the end connector 58' at the other end thereof. In a first longitudinal position wherein the section 12 is substantially planar with the section 14, the cables 20 are wound about the winch cylinders 99 an amount to provide enough tension in the cables 20 to maintain such a substantially planar orientation and configuration, with the hinge extensions 82 and 82' being in contact with each of the cables 20. The motor 98 is preferably low speed and high torque for safely winding both of the cables 20 simultaneously about the cylinders 99 to draw the section 12 toward the section 14 to result in an upward breaking or jointing configuration with the hinges 70 and 72 disposed in spaced relation with the cables 20 and the hinges 70 and 72. The motor 98 may be reversed, reversing the direction of rotation of the winch cylinders 99 for slowly unwinding the cables 20 to a downward breaking or jointing configuration. As the cables 20 unwind, gravity draws the support sections 12 and 14 downward with the cables 20 being received in the grooves 82 and 82' of the hinge extensions 80 and 80'. As the cables 20 slacken, the hinges 70 and 72 continue to lower pressing down upon the cables 20.

It is noted that the frame sections 12 and 14 are typically equipped with pads (not shown) or other patient holding structure, as illustrated, for example, in Applicant's U.S. Pat. No. 5,131,106, the disclosure of which is incorporated by reference herein. It is foreseen that such patient holding structure could translate or glide along the frame sections 12 and 14. Furthermore, with respect to FIGS. 13 and 14, the frame member sections 66 and 68 of section 12 and the frame member sections 66' and 68' of the section 14 may be replaced with substantially rectangular imaging tops or sections 100 and 101' respectively. Each of the sections 100 and 101' having elongate slots 101 formed therein to allow for attachment of the hinge mechanisms 70 and 72 in a manner identical or substantially similar to what has been described herein with respect to the frame sections 12 and 14.

With reference to FIGS. 15-17, the imaging sections 100 and 100' are illustrated, replacing the frame sections 12 and 14 of the embodiment disclosed in FIGS. 1-12. Each of FIGS. 15-17 represent configurations in which the cable drive 18 is tensioned such that the sections 100 and 100' are kept in a substantially coplanar configuration. FIG. 15 illustrates a configuration in which the column 3 is telescoped upwardly with the frame sections hinging at the support assemblies 5 and 6, resulting in an inclined position or configuration of the entire patient support. In the illustrated embodiment, the section 100 would preferably receive a patient's head. Therefore, FIG. 15 illustrates a reverse Trendelenburg position or orientation. FIG. 16 illustrates the sections 100 and 100' again in a substantially common plane with both sections being rotated to a tilted position produced by a powered rotation of the sub assemblies 26 and passive rotation of the assembly 26' with both columns 3 and 4 otherwise holding the sections 100 and 100' at the same height.

FIG. 17 illustrates both tilting due to rotation of the assemblies 26 and 26' and also a sloping or inclined position with the column 4 being extended vertically. Thus, FIG. 17 illustrates a Trendelenburg position or orientation with both the sections 100 and 100' remaining in substantially the same plane. It is foreseen that a bearing block assembly at one or both ends of the table provides for some lateral translation to prevent binding of the hinge mechanisms.

Figure 18:
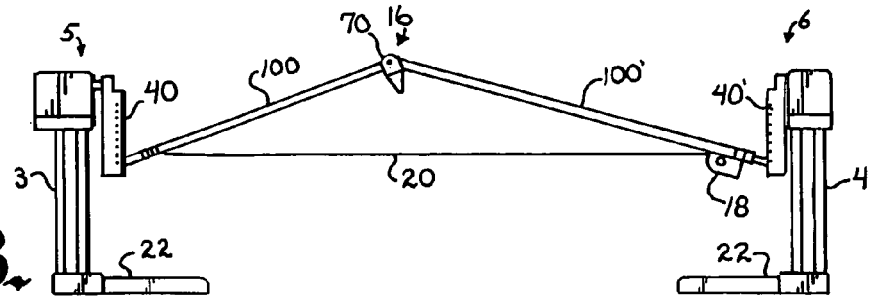
FIG. 18 is a side elevational view of the structure of FIG. 15 shown in a symmetrical upward breaking position.
Figure 19:
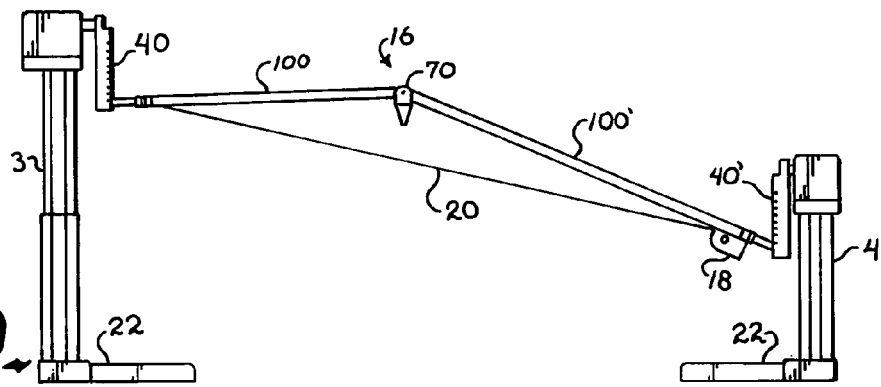
FIG. 19 is a side elevational view of the structure of FIG. 15 shown in a first inclined and upward breaking position.
Figure 20:
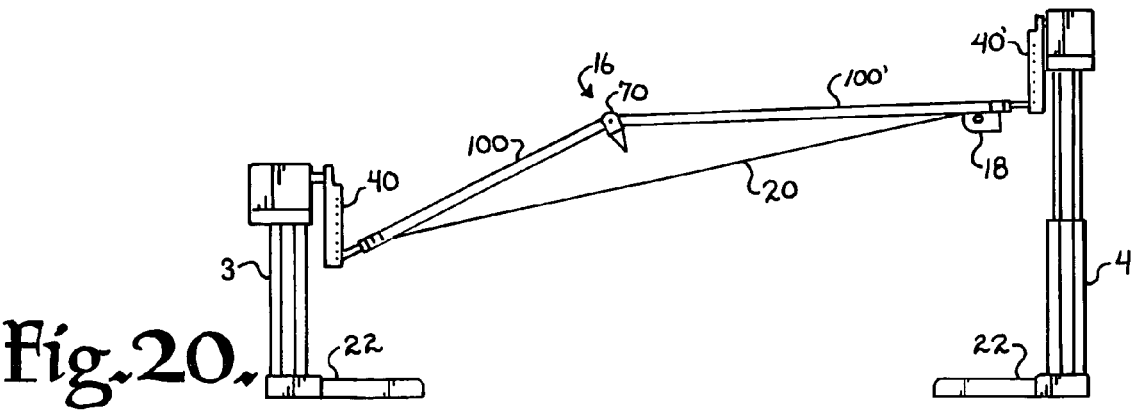
FIG. 20 is a side elevational view of the structure of FIG. 15 shown in a second inclined and upward breaking position.

With reference to FIGS. 18-20, there is illustrated three upward breaking or hinging configurations of the structure 1. FIG. 18 illustrates a symmetrical upward breaking configuration wherein the columns 3 and 4 are holding the respective support assemblies 5 and 6 at substantially the same height with the cables 20 being shortened by rotation of the winch motor to result in an upward break or joint in the hinge assembly 16. FIG. 19 illustrates the column 3 being extended to a maximum height and the cables reeled to shorten a distance between the sections 100 and 100'. An example of such an upward break or joint with reverse Trendelenburg would be a head or column 3 height of 43 inches, a foot or column 4 height of 24 inches and a 35 degree upward break with zero degree roll. FIG. 20 illustrates an upward breaking Trendelenburg with the column 4 being extended to a maximum height.

Figure 22:
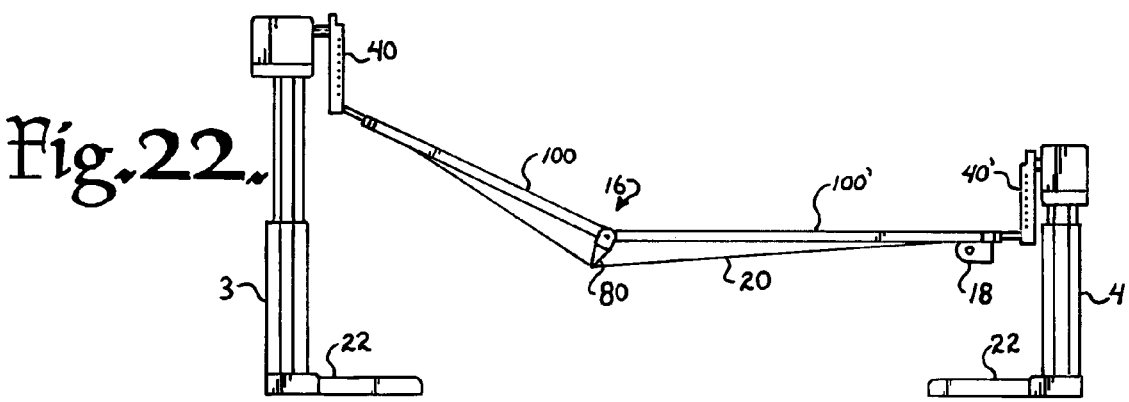
FIG. 22 is a side elevational view of the structure of FIG. 15 shown in a first inclined and downward breaking position.
Figure 23:
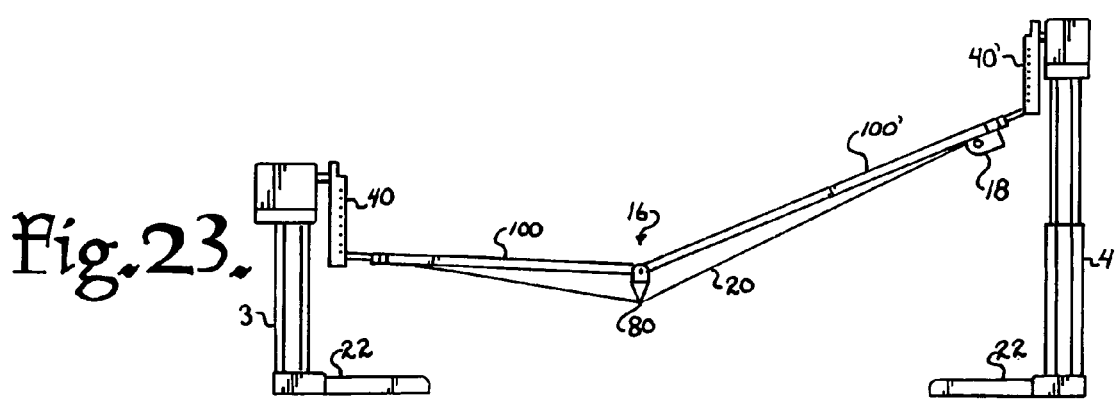
FIG. 23 is a side elevational view of the structure of FIG. 15 shown in a second inclined and downward breaking position.

With reference to FIGS. 21-23, there is illustrated three downward breaking configurations of the structure 1. FIG. 21 illustrates a symmetrical downward breaking configuration wherein the columns 3 and 4 are holding the support assemblies 5 and 6 respectively, at the same height with the cables 20 being unwound or slackened to result in a downward break or joint in the hinge assembly 16, the hinges 70 and 72 contacting the cables 20. FIG. 22 illustrates a downward breaking reverse Trendelenburg with the column 3 being extended to a maximum height resulting in a patient's head end being at a maximum height. FIG. 23 illustrates a downward breaking Trendelenburg with the column 4 being extended to a maximum height.

Figure 24:
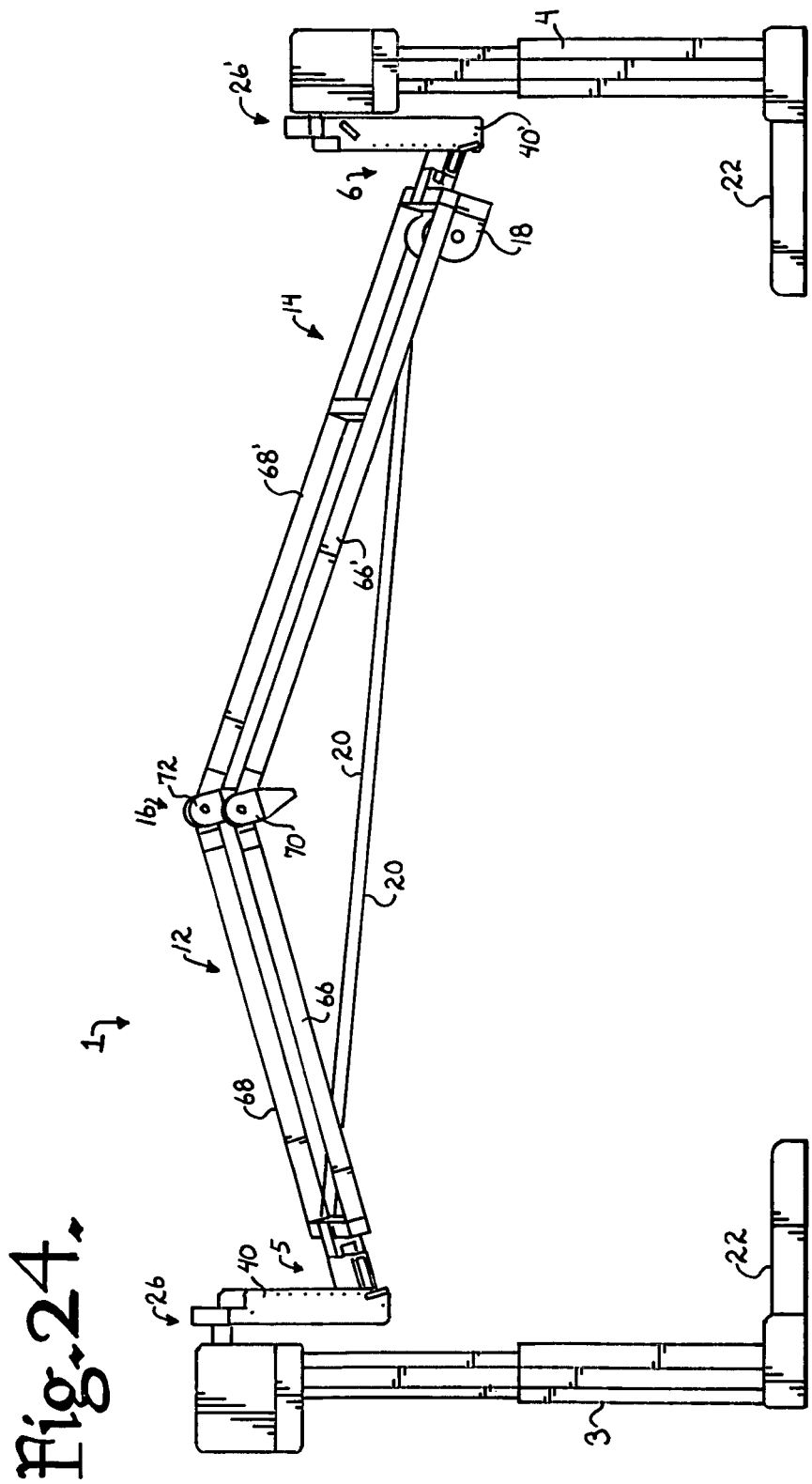
FIG. 24 is an enlarged side elevational view of the structure of FIG. 1 shown in an upward breaking, inclined and tilted position.

It is noted that in each of the configurations illustrated in FIGS. 18-23, the sub-assemblies 26 may be rotated in either direction, resulting in a tilted or rotated as well as upwardly or downwardly broken or hinged configuration. For example, FIG. 24 illustrates the structure 1 with support frame sections 12 and 14 positioned in a configuration similar to that illustrated in FIG. 19, but also including rotation, resulting in a tilting and upwardly breaking or jointed configuration of the structure 1. An example of the position illustrated in FIG. 24 would be: a head or column 3 height of 41 inches, a foot or column 4 height of 34 inches and a 35 degree upward break or joint with 10 degree roll.

With reference to FIGS. 25-29, another structure, generally 102 according to the invention is illustrated. The structure 102 utilizes all of the elements described herein with respect to the structure 1 and therefore the same references numerals are used for the same elements or features. The structure 102 differs from the structure 1 in that the H-bar posts 40 and 40' are replaced or modified to be extended H-bar posts 40A and 40A', allowing for the mounting of two elongate structure 10 and cooperating cable drives 18. In the embodiment shown in FIG. 25, one of the structures 10 includes the frame member 12 and 14 while the other structure is an imaging top having sections 100 and 100'. As previously described herein, the cooperating H-bar posts 40A and 40A' equipped with a plurality of apertures allows for the placement of the support structures 10 at a variety of locations. For example, FIGS. 25-28 illustrate a first spaced orientation of the elongate frame with respect to the elongate imaging top with the imaging top located at a "lower" position identified by the reference letter L. The identical components are shown in FIG. 29 with the imaging top located at a "mid-position" identified by the reference letter M, illustrating a more compact or closely spaced orientation of the elongate frame with respect to the elongate imaging top than what is shown in FIG. 25.

As illustrated in FIGS. 25-28, the structure 102 provides for the complete rotation and thus a roll-over of a patient by actuation of the motor of the rotation subassembly 26 using the controller 29. The structure 102 shown in FIGS. 25-29 is further illustrated with a non-telescoping base support 110 fixed to each of the columns 3 and 4 and rollers or castors 112 at the base of the structure 102.

With reference to FIGS. 30 and 31, another embodiment or system according to the invention, generally 200 is illustrated. The system 200 broadly includes an elongate length-adjustable base 202 surmounted at either end by respective first and second upright support piers or columns 203 and 204 which are connected to respective first and second support assemblies, generally 205 and 206. Between them, the support assemblies 205 and 206 uphold an elongated breaking, hingeable or pivotable patient support structure, generally 210. The hinge structure is described in detail in Applicants's U.S. Pat. No. 7,152,261 and also U.S. patent application Ser. No. 11/159,494, both disclosures of which are incorporated by reference herein. The embodiment 200A illustrated in FIG. 31 differs from the structure 200 only in that the length-adjustable base 202 is replaced by a first base 220 attached to the pier 203 and a second base 222 attached to the pier 204. All of the bases 202, 220 and 222 include castors or rollers 230 or some other movable structure to allow the piers 203 and 204 to move toward and away from one another during upward or downward breaking of the structure 210.

It is foreseen that cable drives as described herein, other types of motor drives including screw drives, universal joints, hydraulic systems, and the like, may be utilized to facilitate both upward and downward breaking of the support structure 210.

Another patient support structure according to the invention, generally 301, is illustrated in FIGS. 32-34. The structure 301 generally includes a horizontally telescoping floor mounted base 302, a conventional or standard telescoping and inclinable operating table support structure 304, a telescoping end support or pier 306 and a hinged or pivotally upwardly and downwardly breaking or jointing support structure 310 connected to both the structure 304 and the pier 306. The patient support structure 310 further includes a first cantilevered section 312 and a second section 314. The first section 312 is fixed to and extends from the operating table support 304. The second section is attached to the pier 306 by a hinge or pivoting assembly 320, such as the support assembly 5 described herein with respect to the structure 1. The hinge mechanism 316 disposed between the support sections 312 and 314 may be a conventional hinge, pivot, or pivot or hinge systems previously described herein.

In use, the operating table support 304 utilizes electric or other power means to move the support section 312 up and down and at an incline, as is known in the art. The operating table support 304 can also tilt or rotate from side to side. In response to the movement of the section 312, the section 314 also moves, resulting in upward and downward breaking illustrated in FIGS. 32 and 33. In response to the movement of the section 312, the electric powered telescoping base 302 moves the pier 306 toward or away from the support 304. The pier 306 includes a motor for raising and lowering the pier at the connection 320.

As stated above with respect to other embodiments of the invention described herein, it is foreseen that cable drives as described herein, other types of drives including screw drives, hydraulic systems, and the like, may be utilized to facilitate both upward and downward breaking of the support structure 310 at the joint 316.

With reference to FIGS. 35-47, another patient support structure according to the invention, generally 401 includes first and second upright support piers or columns 403 and 404 that are connected to one another by a non-telescoping base support 402. In some embodiments according to the invention, each column may be surmounted on an independent movable or stationary base. The column 403 is connected to a first support assembly, generally 405 and the column 404 is connected to a second support assembly, generally 406. Between them, the support assemblies 405 and 406 uphold at least one removable elongate and articulate, substantially centrally jointed or breaking patient holding or support structure, generally 410. The assembly includes a first frame section 412, a second frame section 414 and a pair of identical hinge assemblies, generally 416, disposed between and connecting the first and second frame sections 412 and 414. In the illustrated embodiment, the first frame section 412 for holding a head and upper body of a patient is of a slightly shorter longitudinal length (along an axis X) than the second frame section 414. Therefore, the spaced hinge assemblies 416 are approximately centrally located relative to a body of a patient being placed on the structure 410. In the illustrated embodiment, the hinge assembly further includes a drive system that includes a pull rod assembly, generally 418, and cooperating spaced slider bars 420. Again, other drive systems are foreseen.

The columns 403 and 404 are substantially similar in form and function to the columns 3 and 4 previously described herein with respect to the structure 1. The columns 403 and 404 are supported by outwardly extending feet 422 that include casters that may be equipped with a floor-lock foot lever for lowering the feet 422 into a floor-engaging position. The columns 403 and 404 each include two or more telescoping lift arm segments respectively that permit the height of each of the columns 403 and 404 to be selectively increased and decreased in order to raise and lower all or a selected portion of the connected patient support structure 410.

Each of the support assemblies 405 and 406 generally includes a rotation subassembly 426 and 426' and an angulation subassembly 427 and 427', respectively, that are the same or substantially similar to the subassemblies 26, 26', 27 and 27' previously described herein with respect to the structure 1. In the illustrated embodiment, the angulation subassembly 427 connected to the frame 412 for holding the head and upper body of a patient is shown as substantially identical to the subassembly 27 and therefore shall not be described further herein. The subassembly 427' is substantially similar to the subassembly 27', but with some modifications, including a frame 436 disposed transverse to the overall longitudinal axis X of the structure 401, the frame 436 providing for slidable support of the pair of identical slider bars 420 that are disposed at either side of the frame 414 and near the subassembly 427'.

Similar to the rotation subassembly 26 previously described herein, the rotation subassembly or mechanism 426, includes at least one motor housing 430 surmounting the support column 403. It is foreseen that a cooperating motor may also be mounted on the support column 404. A main rotational shaft 432 extends from the motor housing 430 that turns a rotation structure or bar that in turn is connected to and rotates the patient support 410 about a longitudinal axis. In particular, the motor housing 430 contains a rotary electric motor or other actuator drivingly engaged with the shaft 432. The rotation mechanism 426 is operated by actuating the motor using a switch or other similar means. The shaft 432 rotationally cooperates with a pair of substantially vertically disposed translation posts or H-bar posts 440, the posts 440 being attached to and disposed at either end of the transverse rotation structure or bar 433. Each H-bar post 440 includes a plurality of apertures 444, allowing for selective, hinged vertical placement of the frame section 412 identical or substantially similar to what has been described previously herein with respect to the H-bar posts 40, the angulation sub-assembly 27 and the frame end section 58 of the frame section 12 previously described herein with respect to the structure 1.

With particular reference to FIGS. 38-40, as stated above, the sub-assembly 426' is substantially similar to the sub-assembly 426 and therefore may include a motor and further includes either an active or passive rotational shaft 432' that engages a rotation structure or bar 433' that is attached to a pair of substantially vertically disposed H-bar posts 440'. A plurality of cooperating apertures 444' formed in the posts 440' provide passageway for a pivot pin 446 to extend therethrough. The pivot pin 446 is receivable in each cooperating pair of apertures 444', allowing for selective placement of a translation connector 448 that is sized and shaped to be received between the pair of posts 440' and also receive the pivot pin 446 therethrough. The pin 446 and connector 448 are thus positionable in an orientation transverse to the longitudinal axis X of the patient support frame 410 at a variety of heights to be selected by the surgeon and readily changeable, even during surgery if necessary, to vary the height of the frame section 414. The multiple location or height feature is also advantageous when more than one frame or patient structure is mounted in tandem, for example, when both a frame and imaging table are used together, such as is shown in the embodiment illustrated in FIGS. 25-29. The position of the frame or other structure may be desirably changed to provide close proximity to an imaging top with a distance between a patient support and an imaging top being expandable or reducible depending upon the size or other attributes of a patient and surgical or other requirements. The connector 448 has a slot for receiving the pivot pin 446. It is noted that the H-bar support 440', apertures 444', elongate transverse pin 446 and translation connector 448 are the same or substantially similar in form and function with the respective support 40, apertures 44, transverse pin 46 and translation connector 48 previously described herein with respect to the structure 1.

The translation connector 448 is in turn attached to a pivot connector 452 that is substantially similar to the pivot connector 52 previously described herein with the exception that rather than being attached directly to an end piece or section of the patient support frame 414, the pivot connector 452 is fixed to the frame 436 that is fixed to and supports the slider bars 420 near end surfaces 464 thereof. Thus, the slider bars 420 are in a hinged relationship with the H-bar supports 440'. The slider bars 420 are also in slidable attachment with the frame section 414 and disposed substantially parallel to a longitudinal axis of the section 414 as will be described in greater detail below. Such slidable attachment facilitates upward and downward breaking or hinging of the section 414 with respect to the section 412 at the hinge mechanism 416. Also as more fully described below, the pull rod assembly 418, that is connected to both the frame section 414 and the hinge mechanism 416, is extendable and retractable, controlling the hinge or break angle of the patient support 410 and rendering the support 410 rigid at a desired upward or downward break or joint of the hinge mechanism 416.

With particular reference to FIGS. 38 and 39, the support frame section 414 includes opposed elongate and parallel frame sections 466 and 468 attached to one another by a transverse end frame section 469. A support plate 470 is attached to and is disposed below each of the sections 466, 468 and 469 to provide additional support and stability to the frame section 414 at and near the end section 469. Further support is provided by a pair of frame support plates 471, both of which are fixed to the end support frame section 469 near one end thereof; one plate 471 being fixed to the section 466 and the other plate 471 being fixed to the section 468. At least one pair of slider bar holding structures 472 are fixed to the support plate 470 and extend downwardly therefrom at each of the frame sections 466 and 468. Each structure 472 includes a through bore that extends parallel to the frame sections 466 and 468, the structure 472 for slidably receiving one of the slider bars 420 directly below one of the frame sections 466 and 468 and also orienting the pair of slider bars 420 in a direction substantially parallel to the frame sections 466 and 468. The illustrated slider bar holding structures 472 are spaced from the end frame section 469 and located near a forward edge 473 of the plate 470. In the illustrated embodiment, the holding structures 472 are also bolted to the frame sections 466 or 468. A pair of pull-rod supports 475 are also fixed to the support plate 470 and the frame 414 and extend downwardly therefrom at each of the frame sections 466 and 468 and also downwardly from the end frame section 469. Each structure 475 includes a through bore for receiving a transverse pivot pin or bar 476 mounted below the slider bars 420. The pull-rod assembly 418 is attached to the support 475 at the pivot pin 476 and is thus in hinged relationship with the support 475, pivotally attached thereto at end portions 478.

The pull-rod assembly 418 further includes a pair of housings 480, each housing attached to an end portion 478 and having a powered actuator 482 cooperating with one of a pair of rotatable extendible and retractable rods 484 and a pair of hinge connectors 486, each pivotally attached to a respective cam plate 488 of the respective hinge mechanism 416 at a respective pivot pin 490. The cam plate 488 has a substantially centrally located curvilinear wall 489 forming a curvate aperture or slot, a lower circular aperture for receiving the pin 490 and an upper circular aperture for receiving a pin 502, described in greater detail below. Each pull rod 484 is rotatably mounted within one of the housings 480, such rotation being controlled by operation of the actuator 482 located in the housing 480 and engaged with the rod 484 to screw and thus selectively move or draw the rod 484 into or away from the hinge mechanism 416 in a direction along a longitudinal axis of the rod 484, that in turn results in breaking or jointing of the patient support 410 at the hinge mechanism 416. It is foreseen that other embodiments according to the invention may utilize other types of push/pull rods or mechanisms, including, for example hydraulic systems. An additional centrally located pull-rod or piston may be included to provide additional support. Furthermore, other hinge mechanisms according to the invention may be utilized in lieu of the mechanism 416, for example including, but not limited to, polyaxial joints, roller with spokes, sprockets, toothed gears, universal axis gears, or the like.

With particular reference to FIG. 41, the illustrated pair of hinge mechanisms 416, each having a cam plate 488, further include a pair of forked arms 492 extending from the frame section 412 and a pair of cooperating forked arms 494 attached to and extending from the section 414. Hinge arms 496, 497, 498 and 499 having apertures near opposite ends thereof for receiving pivot pins cooperate with the respective cam plate 488 and adjacent forked arms 492 and 494 at pivot pins 501, 502, 503 and 504. All of the pivot pins 490, 501, 502, 503 and 504 are disposed transverse to the longitudinal axis X of the patient support structure 401. In particular, the pivot pin 501 is received by circular apertures located near first ends of the hinge arms 496 and 498 and a circular aperture in the arm 492, thus pivotally attaching the arm 492 with both the hinge arms 496 and 498. The pivot pin 502 is received by an upper circular aperture in the cam plate 488 and circular apertures located near the ends of each of the forked arms 492 and 494, thus pivotally attaching the cam plate 488 with both of the forked arms 492 and 494. The pivot pin 503 is received by circular apertures located near first ends of the hinge arms 497 and 499 and a circular aperture in the arm 494, thus pivotally attaching the arm 494 with both the hinge arms 497 and 499. The pivot pin 504 is received by the slot 489 and also by circular apertures located near second ends of the hinge arms 496, 497, 498 and 499, thus pivotally attaching all four hinge arms 496, 497, 498 and 499 with the cam plate 488 at the slot 489.

Also, with particular reference to FIGS. 35 and 38-41, the structure 401 is shown in a neutral, planar orientation, with the pull-rod assembly 418 holding the hinge mechanism 416 in such neutral position, with the forked arms 492 and 494 in parallel. In such position, the pin 504 is located at or near a rear-ward end of the slot 489.

Figure 42:
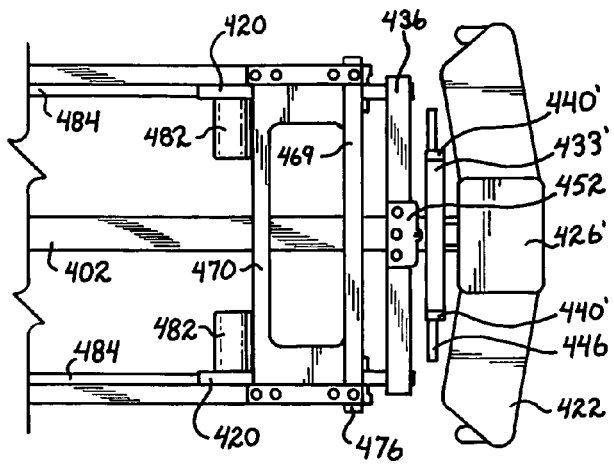
FIG. 42 is an enlarged and partial top plan view of a portion of the structure of FIG. 35 and shown in the same position as shown in FIG. 36.
Figure 44:
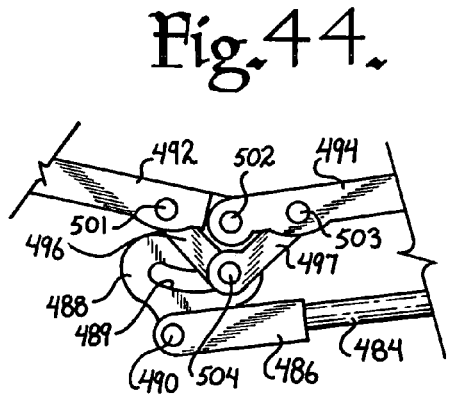
FIG. 44 is an enlarged and partial side elevational view of the structure of FIG. 35 and shown in the same position as shown in FIG. 36.
Figure 43:
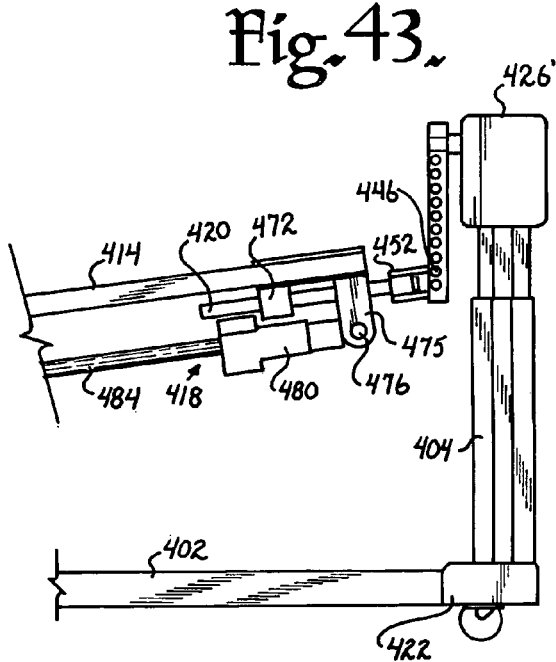
FIG. 43 is an enlarged and partial side elevational view of the structure of FIG. 35 and shown in the same position as shown in FIG. 36.

With reference to FIGS. 42-44, as the rod 484 is rotated to selectively lengthen the rod 484, the pin 504 remains near the rear-ward end of the slot 489 and the pushing of the rod toward the hinge mechanism 416 pivots the cam plate 488 at the pivot pin 490, causing the arms 492 and 494 to move toward the rod hinge connector 486 and thus pivot the patient support at the pin 502, causing a downward break or joint in the patient support 410. With reference to FIGS. 45-47, as the rod 484 is rotated to selectively shorten the length thereof, the support portion 414 slides along the slider bars 420 away from the end support 404. At the same time, the pin 504 slides along the slot 489 to an opposite or forward end thereof as the cam plate pivots in a forward direction about the pin 490. The movement of the rod 484 thus causes an upward break at the pivot pin 502. In the illustrated embodiment, the patient frame is pinned at the head end, but is free to move along the fixed slider bar 420 at the foot end, providing dynamic support to the patient frame. The slider bar mechanism can be attached to a bearing block mechanism to provide lateral translation movement, as described previously.

It is noted that since the patient frame is free to move over the slider bar, a horizontal force component is generated by the combined components of the patient support. When the support is broken or jointed upward, the angle of the foot end frame imparts a horizontal force on the slider that urges the end supports 403 and 404 toward one another. When the table is broken downward, a horizontal force develops that tends to push the end supports apart. It has been found that the magnitude of the horizontal force is a function of support loading and break angle, and thus, for example, if a working limit of five hundred pounds is selected for the patient support, a worst case of horizontal loading is only about fifty-eight pounds at an upward break or joint of thirty-five degrees. It is noted that the illustrated structure 401 advantageously supports a breaking or jointing range from about thirty-five degrees up to about twenty degrees down. Throughout such range, the horizontal forces imposed by the structure are minimized by the illustrated locked support frame that moves on a slider bar at the foot end of the support.

As with the structure 1 configurations illustrated in FIGS. 18-23, the upward and downward breaking of the patient support 410 may be modified by placing the portions 412 and 414 at different vertical locations along the H-bar supports 440 and 440', thus resulting in symmetrical or asymmetrical breaking configurations. Furthermore, the portions 412 and 414 may be rotated or tilted as described above with respect to the structure 1.

FIG. 48 through FIG. 69 illustrate a non-incrementally, continuously or infinitely adjustable patient support and articulation apparatus, generally 600, for supporting a patient during a medical procedure, and to modify or change the angle of articulation of the patient, such as at a point of articulation, generally 601, preferably without substantially changing a height H of the point of articulation 601 relative to a floor F supporting the apparatus 600 according to the invention during a particular surgery. However, the height of the articulation is also variable, for example to adjust for the height of different surgeons or for particular procedures. The apparatus 600 includes a longitudinal axis of rotation B (see FIGS. 48 and 57), a perpendicular axis of rotation C associated with the point of articulation 601 (see FIG. 57), spaced head-end and foot-end lift subassemblies, generally 602 and 604, also referred to as first and second piers or columns, a patient support subassembly, generally 606, an articulation subassembly, generally 607, and a powered actuator. The head-end and foot-end lift subassemblies 602 and 604 are joined by a non-telescoping base support structure 608, which may include a cross-bar 610 running parallel with the axis B and a plurality of casters 612. The base support structure 608 holds the lift subassemblies 602 and 604 in opposed spaced relation to one another, as well as preventing the lift subassemblies 602 and 604 from toppling over during operation of the apparatus 600 due to the large forces exerted on the apparatus 600 by a patient during surgery.

Referring to FIGS. 48-50, 56-60, 62-63, the first or head-end lift subassembly 602 provides for continuous adjustable raising and lowering of the head-end of the patient support subassembly 606 over an infinitely adjustable range and, for example, a distance from about 0.5-inches or less to about 6-inches, 1-foot, 1.5-feet, 2.0-feet, 2.5-feet, 3.0 feet or more, in cooperation with other components of the apparatus 600, as described herein. It is noted that the head-end lift subassembly 602 operates in concert with or cooperates with other apparatus components, such as the foot-end lift subassembly 604 and the articulation subassembly 607, such that an angle of articulation D (see FIGS. 59 and 60) of the articulation point 601 may be modified without a substantial change in height H of the articulation point 601 during a particular surgery, so as to maintain the surgical site of the patient at a preferred height for the surgeon conducting the surgery. The head-end lift subassembly 602 also provides for continuously adjustable rotation or tilting of the patient support subassembly 606 in an infinitely adjustable range from 0° to 90°, and for example, about ±5°, ±10°, ±15°, ±20°, ±25° or more relative to the axis of rotation B, also in cooperation with the other components of the apparatus 600, as described herein. The head-end lift subassembly 602 includes an individually operable and continuously adjustable primary elevator 614, or primary lift subassembly, a rotational subassembly, generally 616, and a footing 618, which are described in greater detail below.

The primary elevator 614, of the head-end lift subassembly 602, includes at least two risers, such as a lower riser 620 and an upper riser 622, and an internal motorized structure for telescopingly raising and lowering the upper riser 622 relative to the lower riser 620 in a continuously or infinitely adjustable, non-segmented manner. The primary elevator 614 includes one intermediate risers 624 and it is foreseen that additional intermediate rises may be utilized. When the primary elevator 614 includes an intermediate riser 624, the internal motorized structure telescopingly raises and lowers the lower, upper and intermediate risers 620, 622 and 624 relative to one another in a continuously adjustable, non-segmented manner. It is foreseen that the internal motorized structure for telescopingly raising and lowering the risers 620, 622 and 624 may include any suitable continuously adjustable, non-segmented drive known in the art, such as, but not limited to a cable drive, screw drives and hydraulic drives. The head-end lift sub assembly 602 includes a powered actuator, electronics and the like, to actuate the primary elevator 614 and the rotation subassembly 616.

The primary elevator 614 moves under control to continuously and adjustably between a maximum lift or fully extended position, shown on the left side of FIG. 49, and minimum lift or fully lowered position, shown on the left side of FIG. 50. Accordingly, extension of the primary elevator 614 may be adjusted over an infinitely adjustable wide range, for example a distance from about 0.5-inches or less to about 6-inches, 1-foot, 1.5-feet, 2.0-feet, 2.5-feet, 3.0 feet or more. In the fully extended position, the risers 620, 622 and 624 are maximumly outwardly telescoped, or opened, relative to one another, such that a top of the head-end lift subassembly 602 is maximally elevated above the floor F. In contrast, in the fully lowered position, the risers 620, 622 and 624 are maximumly inwardly telescoped, or closed, relative to one another, such that the top of the head-end lift subassembly 602 is as close to the floor F as mechanically possible.

FIG. 48 illustrates an intermediate position of the primary elevator 614, wherein the risers 620, 622 and 624 are intermediately outwardly telescoped relative to one another, such that the top of the head-end lift subassembly 602 is in between the minimum and maximum possible heights. As will be described in greater detail, below, continuously adjustable, non-segmented inward and outward telescoping of the risers 620, 622 and 624, in conjunction with coordinated continuously adjustable, non-segmented cooperative movement of other portions of the patient support and articulation apparatus 600 is associated with positioning the patient, so that the patient's spine will be in a suitable lordotic or kyphotic position for a given surgical procedure or on their side, such as changing the angle D while substantially maintaining the height H of the point of articulation 601 and optionally or preferably maintaining the patient's torso in a generally horizontal, non-head down position.

Figure 62:
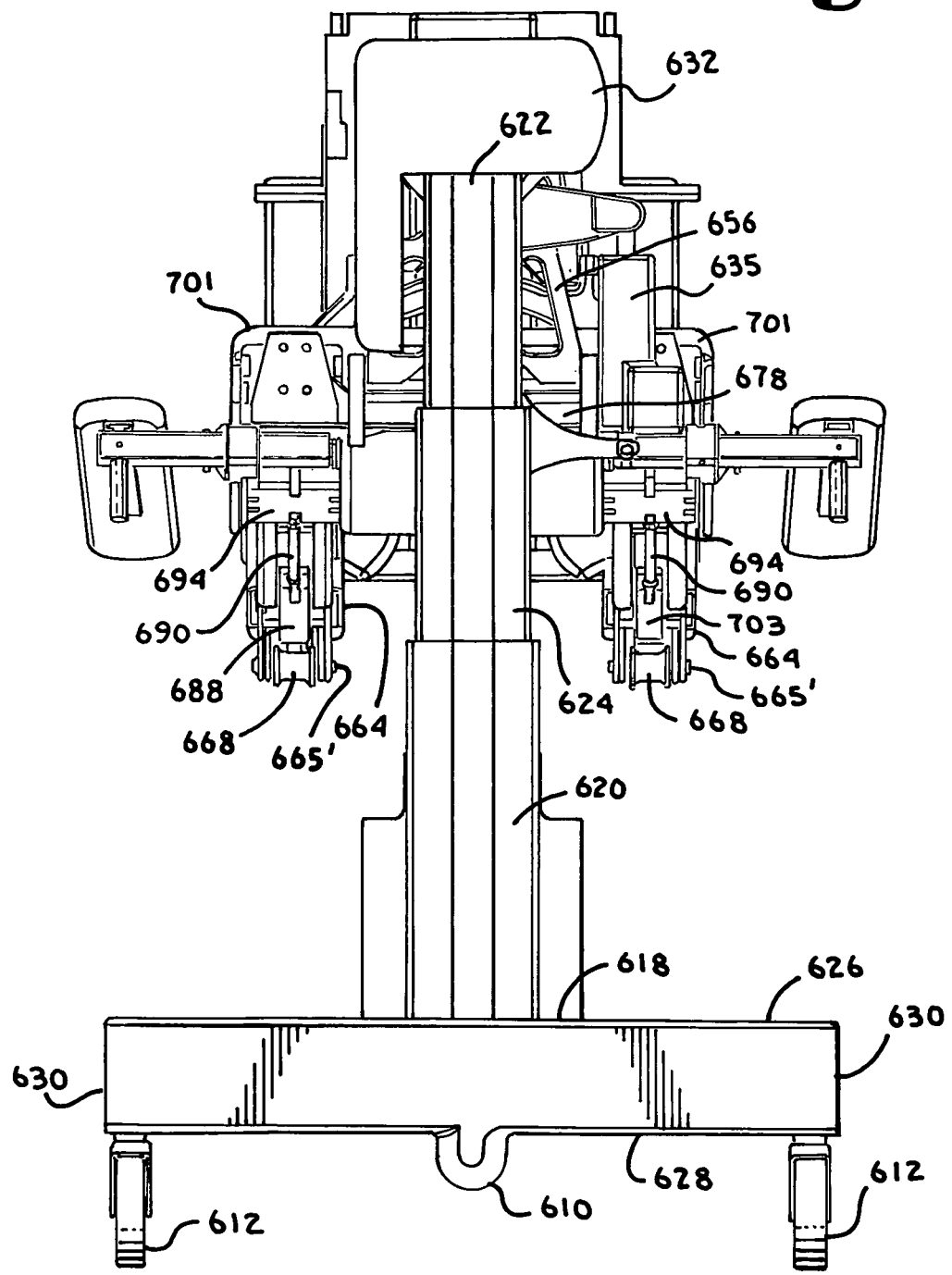
FIG. 62 is an enlarged head-end elevational view of the patient support structure of FIG. 48 and shown in the same position as shown in FIG. 49.
Figure 63:
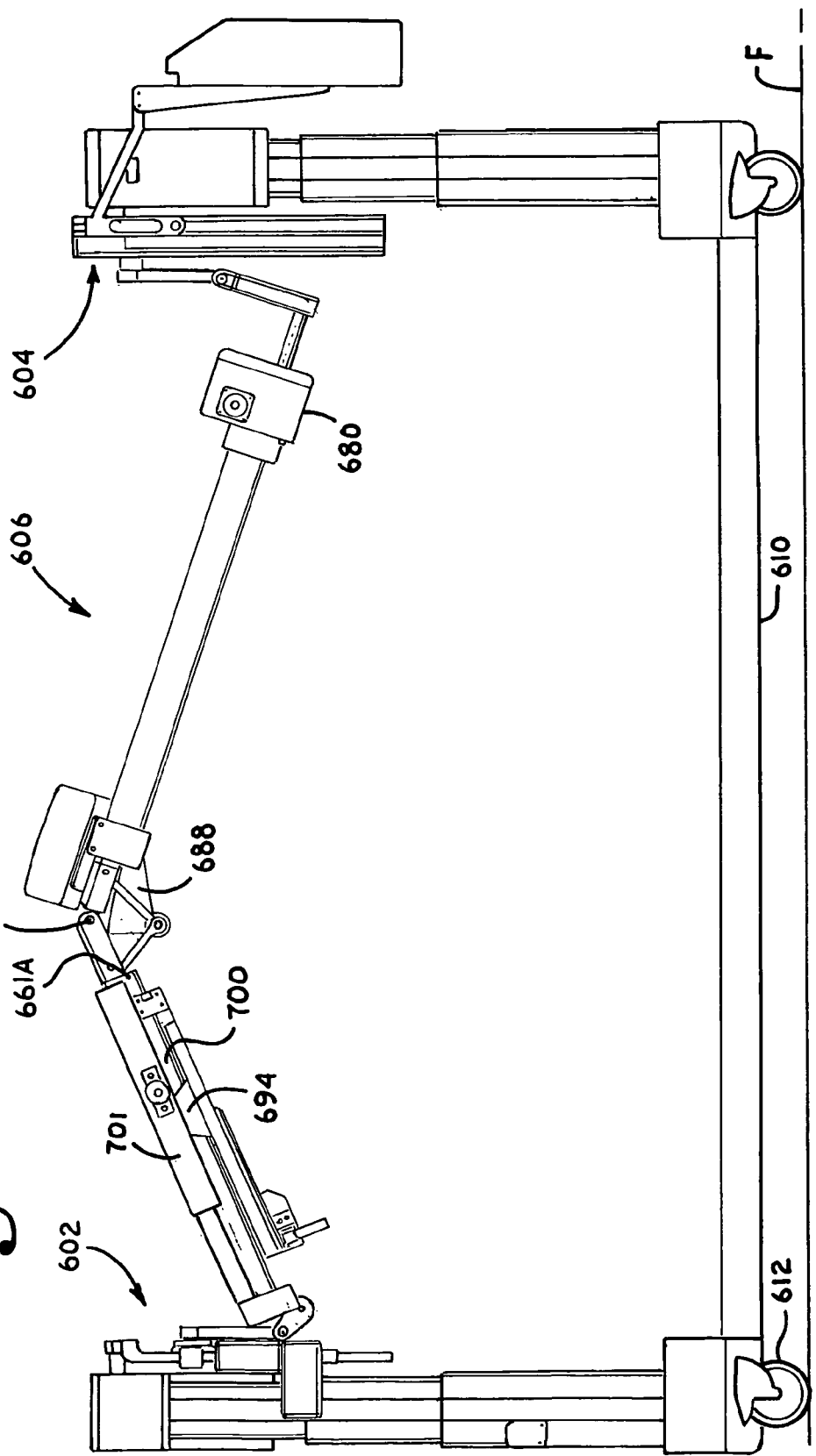
FIG. 63 is a side elevation view of the patient support structure of FIG. 48, shown in an upwardly breaking position and in a fully elevated position.
Figure 64:
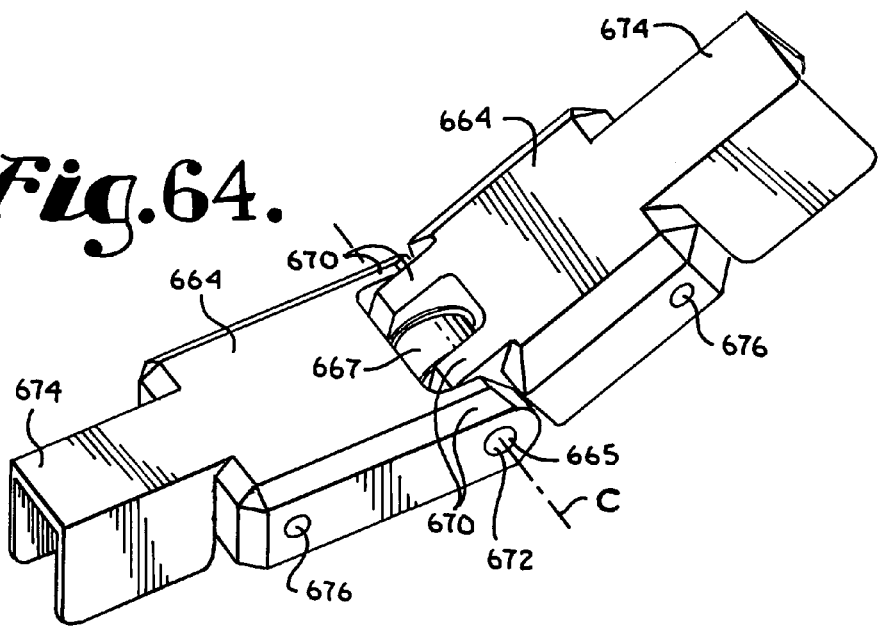
FIG. 64 is an enlarged top perspective view of a portion of the hinge and roller of FIG. 48 and in a downward breaking position.

The lower riser 620 rests on the footing 618, which includes a housing and at least some of the internal motorized structure of the head-end lift subassembly 602. As shown in FIGS. 57 and 62, the footing 618 extends perpendicularly outward relative to a longitudinal axis B, so as to provide a sturdy support that sufficiently resists sideways tipping of the apparatus 600. The footing 618 includes top and bottom sides 626 and 628, and opposed outer ends 630. A caster 612 extends downwardly from the bottom side 628, adjacent to each of the outer ends 630. The cross-bar 610 is centrally attached to the footing bottom side 628, so as to extend substantially parallel with the longitudinal axis B and the floor F. The cross-bar 610 joins the footing 618 with a footing 618' of the foot-end lift subassembly 604, described below, so as to hold the footings 618 and 618' in fixed relation and to provide support to the apparatus 600.

The head-end lift subassembly 602 supports the rotational subassembly 616, which includes an hydraulic piston assembly 632 that rotates or tilts the patient support subassembly 606 and a rotational shaft 634, such as is described elsewhere herein. It is foreseen that other structures such as motors or drives may be used to rotate the subassembly 606. The rotational shaft 634 is substantially parallel with axis of rotation B, and extends longitudinally inward from the motor housing 632. The rotational shaft 634 is rotatably joined with both the patient support subassembly 606 and internal mechanical components of the rotational subassembly 616, including a gear-driven device however, it is foreseen that, screw-driven, cable-driven or piston-driven drives the like. Rotating the rotational shaft 634 rotates or tilts the patient support subassembly 606 clockwise or counter-clockwise in a continuous range from 0° to 90° either way, for example about ±5°, ±10°, ±15°, ±20°, or more relative to axis B. It is foreseen that the drive-device of the rotational subassembly 616 may be located in the top or side of the head-end lift subassembly and in some circumstances, some portions of the drive-device may extend downwardly from the rotational subassembly 616 and into the footing 618. In the illustrated embodiment, a piston 635 is located at the side of the primary elevator 614, that operably rotates the patient support subassembly 60 clockwise or counter-clockwise through a range of plus or minus 20° relative to axis B. Numerous configurations are foreseen. Additionally or alternatively, it is foreseen that a rotational subassembly 616' may be located at the foot-end lift subassembly 604. The rotational shaft 634 may be passive, and rotate in response to rotation of the patient support subassembly 606 by other apparatus components, such as but not limited to the rotational subassembly 616'. Alternatively, both the rotational subassembly 616 and the rotational subassembly 616' may actively drive rotation of the patient support subassembly 606, such as by a gear-driven, screw-driven, cable-driven or piston-driven drive known in the art.

The second or foot-end lift subassembly 604 provides for continuous adjustable raising and lowering of the foot-end of the patient support subassembly 606 over an infinitely adjustable range, for example a distance from about 0.5-inches or less to about 6-inches, 1-foot, 1.5-feet, 2.0-feet, 2.5-feet, 3.0 feet or more, in cooperation with other components of the apparatus 600, as described herein. The foot-end lift subassembly 604 also provides for continuous adjustable, non-segmented rotation or tilting of the patient support subassembly 606 over an infinitely adjustable range, for example an amount up to about ±5°, ±10°, ±15°, ±20°, or more relative to the axis B, also in cooperation with other components of the apparatus 600, as described herein. The foot-end lift subassembly 604 includes primary and secondary elevators 614' and 636, a passive rotational subassembly 616' and a footing 618'. However, it is foreseen that the rotational subassembly 616' may also be active and include the same structure as the head-end. Similar to the head-end lift subassembly 602, the footing 618' supports the primary elevator 614', which supports the rotational subassembly 616'. Unlike the head-end lift subassembly 602, the secondary elevator 636 is operably joined with the rotational subassembly 616' of the foot-end lift subassembly 604. The primary and secondary elevators 614' and 636 are individually yet cooperatively operable and continuously adjustable in a non-segmented infinitely adjustable manner.

The primary elevator 614' is substantially similar to the primary elevator 614 and cooperates with other apparatus components, such as the head-end lift subassembly 602, the secondary elevator 636 and the articulation subassembly 607, such that the angle of articulation D may be modified without a substantial change in height H of the articulation point 601. Accordingly, the primary elevator 614' includes at least two risers, such as a lower riser 620' and an upper riser 622', and an internal motorized structure such as described herein, and provides for modification of a height of the primary elevator 614' over an infinitely adjustable range, and for example, a distance from about 0.5-inches or less to about 6-inches, 1-foot, 1.5-feet, 2.0-feet, 2.5-feet, 3.0 feet or more. The primary elevator 614' may include one or more intermediate risers 624'. In the illustrated embodiment, the primary elevator 614' shown on the right side of FIG. 49 includes one intermediate riser 624'. It is foreseen that in some circumstances, the primary elevator 614' may include two or more intermediate risers 624'. When the primary elevator 614' includes an intermediate riser 624', the internal motorized structure telescopingly raises and lowers the lower, upper and intermediate risers 620', 622' and 624' and relative to one another in a continuously and infinitely adjustable, non-segmented manner. It is foreseen that the internal motorized structure for telescopingly raising and lowering the risers 620', 622' and 624' may include any suitable continuously adjustable, non-segmented drive known in the art, such as but not limited to a cable drive, screw drives and hydraulic systems, such as described herein.

Referring again to FIGS. 49 and 50, the primary elevator 614' is adapted to move between a maximum lift or fully extended position, shown on the right side of FIG. 49, and a minimum lift or fully lowered position, shown on the right side of FIG. 50. In the fully extended position, the risers 620', 622' and 624' are maximumly outwardly telescoped, or opened, relative to one another, such that a top of the foot-end lift subassembly 604 is maximally elevated above the floor F. In contrast, in the fully lowered position, the risers 620', 622' and 624' are maximumly inwardly telescoped, or closed, relative to one another, such that the top of the foot-end lift subassembly 604 is maximally lowered toward the floor F. It is noted that, in the illustrated embodiment, when the primary elevator 614' is in the least-outwardly telescoped position or configuration thereof, only the lower riser 620' is visible from the side of the apparatus 600. For example, the intermediate riser 624' is operably so as to slide downwardly into the lower riser 620', and the upper riser 622' is operable so as to slide downwardly into the intermediate riser 624'. In some circumstances, the housing of the rotational subassembly 616' shrouds at least a portion of the risers 620', 622' and 624'. FIG. 48 illustrates an intermediate position of the primary elevator 614, wherein the risers 620', 622' and 624' are intermediately outwardly telescoped relative to one another, such that the top of the foot-end lift subassembly 604 is in between the minimum and maximum possible heights. As will be described in greater detail, below, inward and outward telescoping of the risers 620', 622' and 624', in conjunction with cooperative movement of other portions of the patient support and articulation apparatus 600 is associated with positioning the patient, so that the patient's spine will be in a suitable lordotic, kyphotic or sideways position for a given surgical procedure.

The primary elevator 614' is joined with the footing 618', which is substantially similar to the footing 618, and which may house a portion of the internal motorized lift structure. The footing 618' includes a top surface 626', a bottom surface 628' and opposed outer ends or surfaces 630'. Casters 612 are attached to the outer ends 630' of the footing 618', and the cross-bar 610 is attached to the bottom 628' of the footing 618', such as described herein with respect to footing 618.

The foot-end lift subassembly 604 includes at least a passive rotational subassembly 616'. It is foreseen that the subassembly 604 may include an active or powered rotational subassembly 616' that is similar to the rotational subassembly 616 of the head-end lift subassembly 602.

Figure 54:
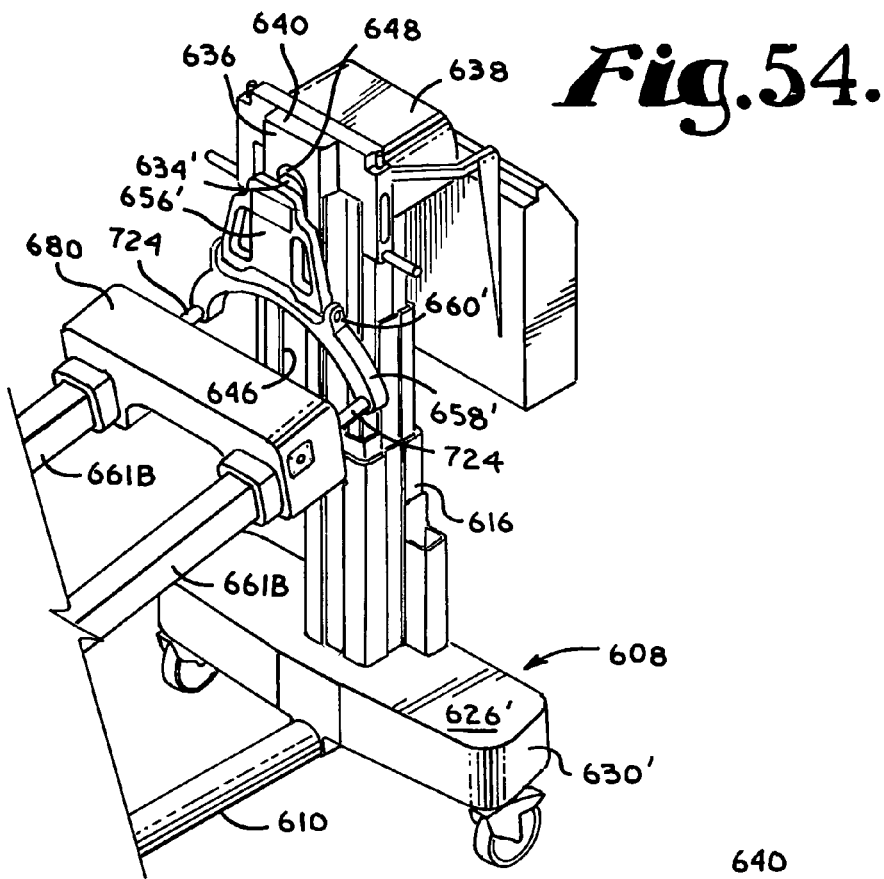
FIG. 54 is an enlarged partial perspective view of the patient support structure of FIG. 48, shown in a fully elevated position.
Figure 55:
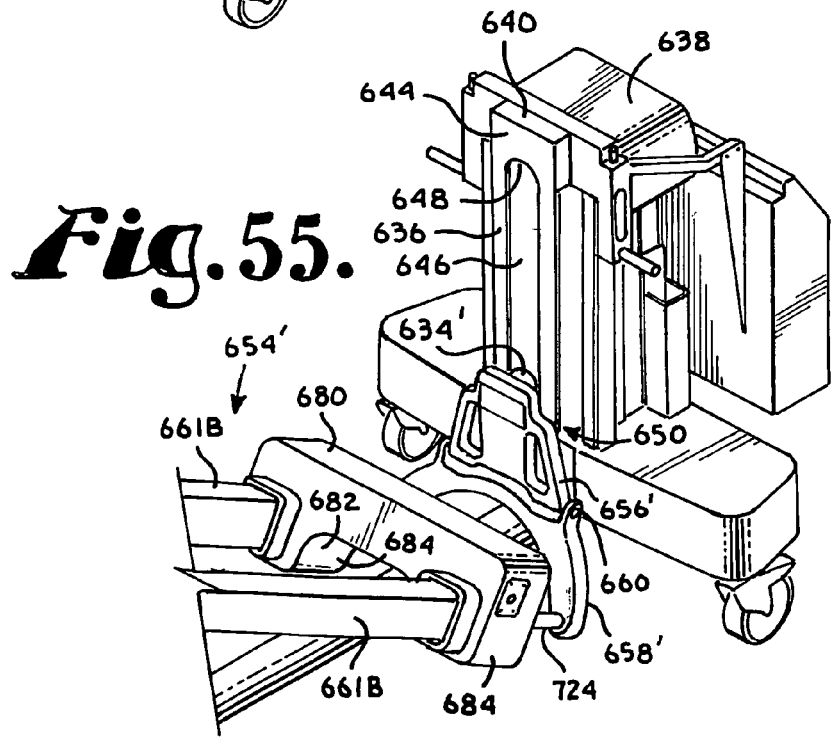
FIG. 55 is an enlarged partial perspective view of the patient support structure of FIG. 54, shown in a fully lowered position.

Referring to FIGS. 54 and 55, the secondary elevator 636 is joined with the top of the primary elevator 614' of the foot-end lift subassembly 604, such as, for example, at the housing of the rotational subassembly 616', such that the secondary elevator 636 in use is operationally raisable or lowerable by the primary elevator 614'. The secondary elevator cooperates with other apparatus components, such as the head-end lift subassembly 602, the primary elevator 614' and the articulation subassembly 607, such that the angle of articulation of the articulation point 601 may be modified without a substantial change in height H of the articulation point 601.

The secondary elevator 636 extends along the inboard side or face of the foot-end lift subassembly 604, from about the top 638, or top surface, of the foot-end lift subassembly 614, downwards toward the floor F. A top 640 of the secondary elevator 636 may be about coplanar with the top 638 of the foot-end lift subassembly 614, or the top 640 may be somewhat above or below the top 638 of the foot-end lift subassembly 614. The secondary elevator 636 preferably includes a height, or length, sufficient that when the foot-end lift subassembly 604 is in the lowest elevational position, such as is shown in FIG. 56, the bottom 642 of the secondary elevator 636 is located near the top 626' of the footing 618'.

Figure 60:
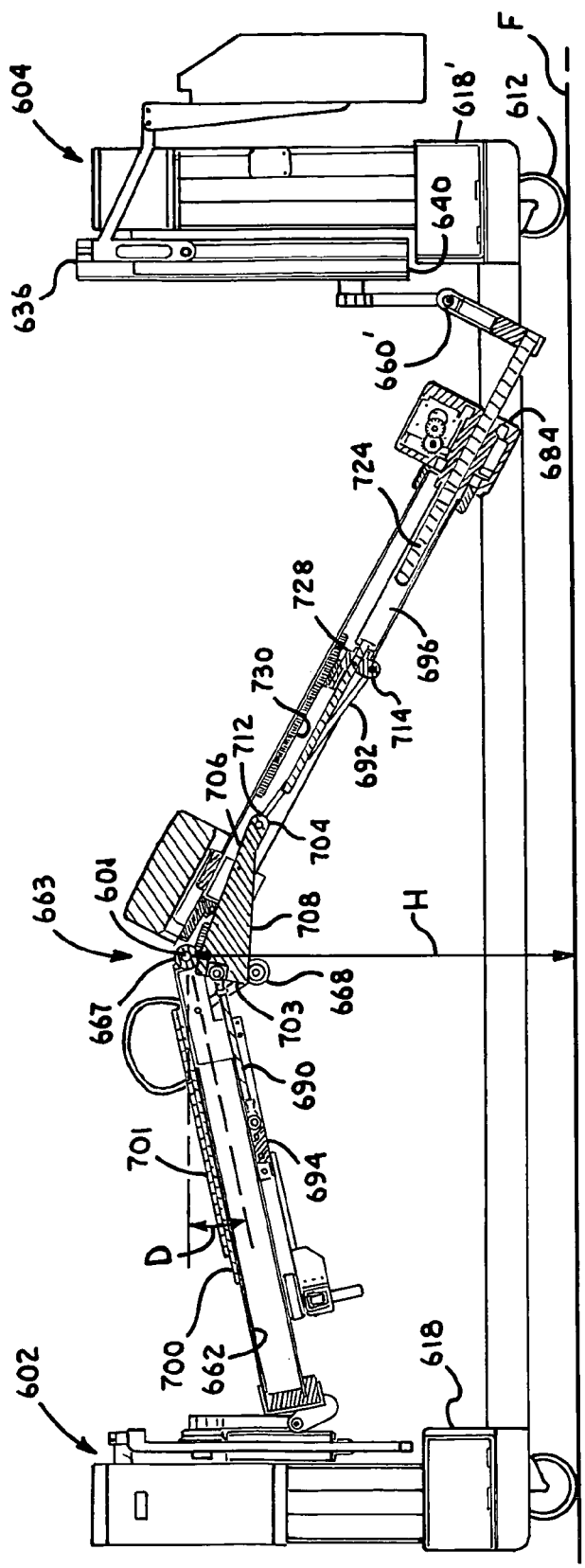
FIG. 60 is an enlarged cross-sectional view of a portion of the patient support structure of FIG. 48, taken along line 58-58 of FIG. 57, and shown in the same position as shown in FIG. 50.

Referring to FIGS. 54-55, the front or inboard side 644, or face, of the secondary elevator 636 includes an extended vertical slot 646 with a height sufficient to adjustably continuously raise or lower the foot-end of the patient support subassembly 606 in an infinitely adjustable range, for example, a distance of between about less than 0.5-inches, about 0.5-inches, 6-inches or 1-foot and about 1.5-feet, 2.0-feet, 2.5-feet or 3.0 feet or more. A second rotational shaft 634' extends toward the patient support subassembly 606 from the vertical slot 646 such that the shaft 634' is substantially parallel to the axis B or the floor F. The secondary elevator 636 includes a motorized drive, such as is known in the art and described herein, that vertically raises and lowers the shaft 634' within the slot 646. As shown in FIGS. 50 and 60, when the primary elevator 614' is in the lowest telescoping position or closed, the secondary elevator 636 is lower the outboard end, generally 652, of the patient support subassembly 606 into close proximity with the floor, for example, within a few inches of the floor F, such as a distance of about 1-inch or less, about 2-inches, about 3-inches, about 4-inches, about 5-inches, or more. FIG. 54 shows the shaft 634' in a most elevated position with respect to the secondary elevator 636, wherein the shaft 364' is at the top 648 of the slot 646. In comparison, FIG. 55 shows shaft 634' is at the bottom 650 of the slot 646. In use, the secondary elevator 636 is independently operated relative to the primary elevator 614' or cooperatively with the primary elevator 614'.

The patient support and articulation apparatus 600 includes a patient support subassembly 606 rotatably joined with the head-end and foot-end lift subassemblies 602 and 604. The patient support subassembly 606 includes a head-end support 654 and a foot-end support 654', each of which has an inboard end and an outboard end. At the outboard ends, the head-end and foot-end supports 654 and 654' are joined to a respective rotational subassembly 616, 616' by an intervening translation subassembly 655 and 655' that includes one or more of an attachment plate 656 and 656', a cross-bar 658 and 658', and one or more pivot joints 660 and 660', such as universal joints or pairs of perpendicularly oriented joints or other suitable pivot structures known in the art. In the illustrated embodiment, such as is shown in FIGS. 54 and 55, the attachment plate 656' and the cross-bar 658' are joined by the joint 660'. When the outboard end of the foot-end support 654' continuously moves between raised and lowered positions, or when the angulation of the pivot point 601 (e.g., angle D) is modified or changed, the attachment plate 656' and the cross-bar 568' pivot with respect to each other at the joint 660'. Similar angulation occurs between the attachment plat 656 and the cross-bar 658 at joint 660.

Each of the head-end and foot-end supports 654 and 654' includes a pair of longitudinally extending frames 661A and 661B, respectively, for support of the patient. The frames 661A, 661B may be made of any sufficiently strong, rigid material, such as aluminum, carbon fiber, hardened metal, and the like. Preferably, the material of construction of the frames 661A and 661B is non opaque to x-rays, so that imaging can occur during surgery. In cross-section, the frames 661A, 661B of the illustrated embodiment are trapezoidal, with the bottom side being wider than the top side, such that the frames 661A, 661B substantially resists torque and tensions applied thereto during movement of the apparatus 600. However, it is foreseen that the frames 661A, 661B may include other cross-sections, such as but not limited to circles, ovals, triangles, rectangles, quadrilaterals and the like.

Each of the frames 661A, 661B includes a longitudinally extending elongate slot or through-bore, generally 662. In the illustrated embodiment, the elongate slot 662 includes a rectangular cross-section and opens downwardly, such as on the bottom side of the cross-section. However, it is foreseen that the elongate slot 662 may have a fourth side, such that the area of the slot 662 is a fully enclosed through-bore, such as is known in the art. Alternatively, the frames 661A, 661B may be tubes with longitudinally extending through-bores 662 therethrough. It is also foreseen that the elongate slot 662 may include other cross-sections, such as but not limited to circles, ovals, triangles, rectangles, quadrilaterals and the like.

Referring to FIG. 57, pairs of frames 661A and 661B are joined at their respective outboard ends, but not at their inboard ends. Referring to FIG. 66, at the outboard ends, the frames 661A are joined by a perpendicular cross-bar 678 that is joined with the cross-bar 656 of the translation subassembly 655. In contrast, the outboard ends of the frames 661B are joined by a gearbox 680, which is also part of the angulation subassembly 607. As is discussed in greater detail below, and is shown in FIGS. 50, 55, 56, 60, and 67, the gearbox 680 includes an arch 676, or bowed portion, sized and shaped such that portions 678 of the gearbox 680 may be lowered near to the floor F and around the base support cross-bar 610. It is noted that lowering the outboard end of the foot-end support 654' sufficiently that the gearbox 680 is located at least partially around the cross-bar 610 enables the head-end support 654 to be maintained in a substantially horizontal orientation, or substantially parallel with the floor F, during angulation of the patient (e.g., angle D), such that the patient's torso may be supported or held in a substantially horizontal or near horizontal orientation, without the head hanging downward and thus reducing side effects of the surgery on the patient.

Referring to FIG. 66, the frames 661A and 661B are joined at the point of articulation 601, or the axis of rotation C, by a hinge 663. Accordingly, the frames 661A, 661B provide an open framework for supporting the patient in a prone, pendulous manner, with his stomach hanging downwardly, such as is shown in FIGS. 57 and 66. Additionally or alternatively, rectangular surgical support tops or imaging tops, similar to tops 100 and 100', may be placed on the framework such that the patient can be supported in a supine position or on one of the patient's sides.

Referring to FIGS. 51-53 and 64-65, each hinge 663 includes a pair of knuckles 664 joined by an upper axle 665, upper and lower rollers 667 and 668, a plurality of V-links 669, and a lower axle 665' pivotably joining the lower roller 668 and the V-links 669. The hinge can be a wide range of structures that allows articulation between the frames 661A and 661B and is located whereat it is best for the patient to bend during surgery. In the illustrated embodiment, each knuckle 664 includes a pair of longitudinally extending, spaced fingers 670. Each of the fingers 670 includes a through-bore 672 that is coaxial with axis C. The upper axle 665 rotatably engages the through-bores 672, such that the upper axle 665 is coaxial with axis C. The respective frames 661A, 661B are joined or engaged by the knuckles 664 at their associated outboard ends 674. Accordingly, the knuckles can pivot on the upper axle 665 with respect to axis C to thereby modify angle D. The upper roller 667 includes a through-bore 667A that pivotably receives the upper axle 665 therethrough, such that the upper roller 665 is located between the fingers 670 of the joined knuckles 664. The upper roller 665 is coaxial with axis C and adapted to pivot freely thereabout independently of the knuckles 664 or of angulation of angle D. In the illustrated embodiment, the upper roller 667 includes a circular cross-section. However, it is foreseen that the upper roller 667 may have an alternatively shaped cross-section, such as but not limited to a rectangle, a polygon, an oval, or the like. It is foreseen that the upper roller 667 may be an alternative structure that provides the same function as the upper roller 667. The upper roller 667 may be fabricated of any suitable material that is sufficiently strong so as to withstand the high forces applied thereto during surgery, while still being able to pivot or roll. For example, the roller 667 may be fabricated of hardened metals, carbon fibre, brass, aluminum, and the like, preferably a hardened steel. In some circumstances, the roller may be coated with a hard slick material to facilitate rolling, such as is known in the art.

In the illustrated embodiment, the lower roller 668 is substantially similar to the upper roller 667 in size, shape and fabrication. However, the lower roller 668 may be include alternative sizes, shapes and materials known in the art.

Figure 52:
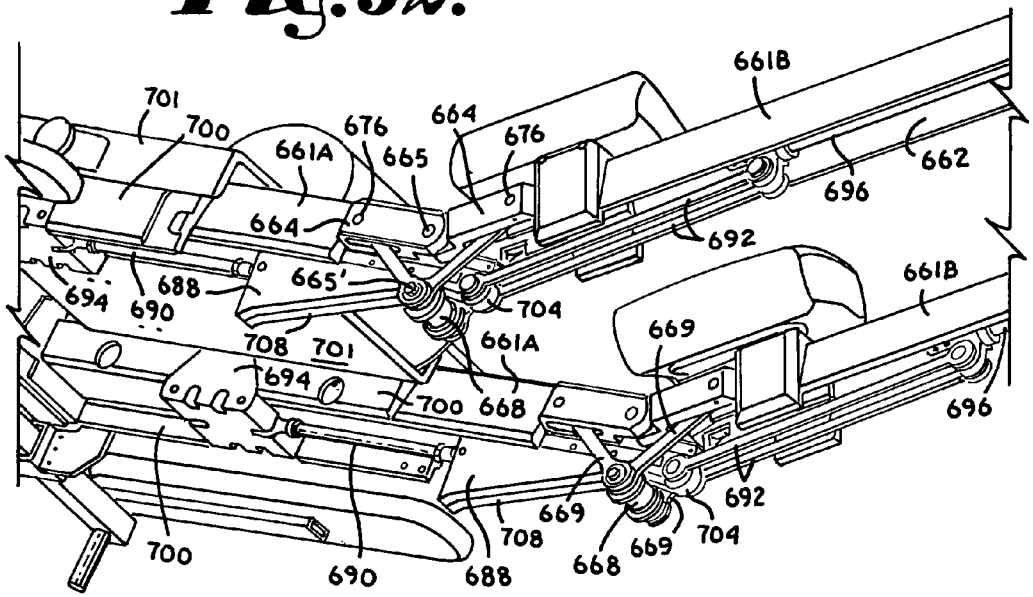
FIG. 52 is an enlarged bottom perspective view of a portion of the patient support structure of FIG. 48, shown in the same position as shown in FIG. 49.
Figure 53:
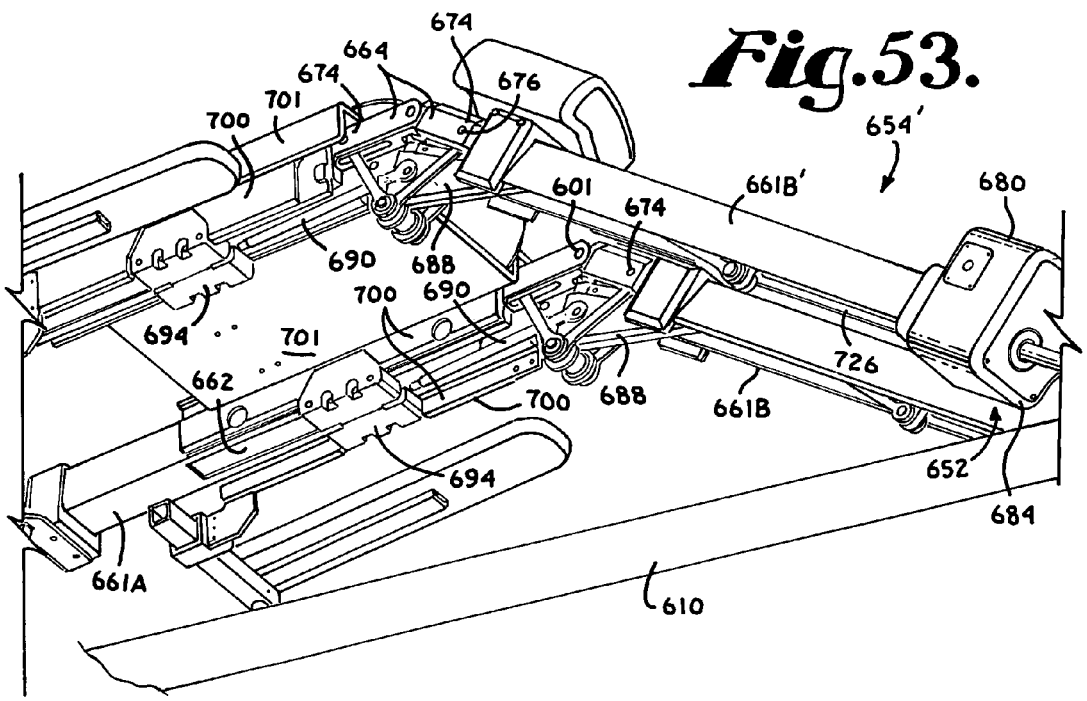
FIG. 53 is an enlarged bottom perspective view of a portion of the patient support structure of FIG. 48, shown in the same position as shown in FIG. 50.

The rod-like V-links 669 pivotably engage the knuckles 664 and the lower axle 665', such that an angle E is defined by a pair of intersecting V-links 669 (see FIGS. 50, 52 and 53). Pins pivotably secure the V-links 669 with the knuckles 664 at rear through-bores 676. The V-links 669 are configured and arranged such that the angle E operably moves through a plurality of continuous angles associated with articulation of the patient support subassembly 606. The V-links may be fabricated of any sufficiently resilient material that can withstand high stress and tension. Suitable materials include but are not limited to carbon fiber, hardened metals, aluminum, certain polymers, and the like, and preferably a hardened steel. In some circumstances, the V-links may be fabricated of strong elastic materials, such as certain polymers and composites. Further, in some embodiments, instead of being rod-shaped, the V-links may be braided or non-braided cords, bars, elastic bands and the like, such as is known in the art.

Figure 61:
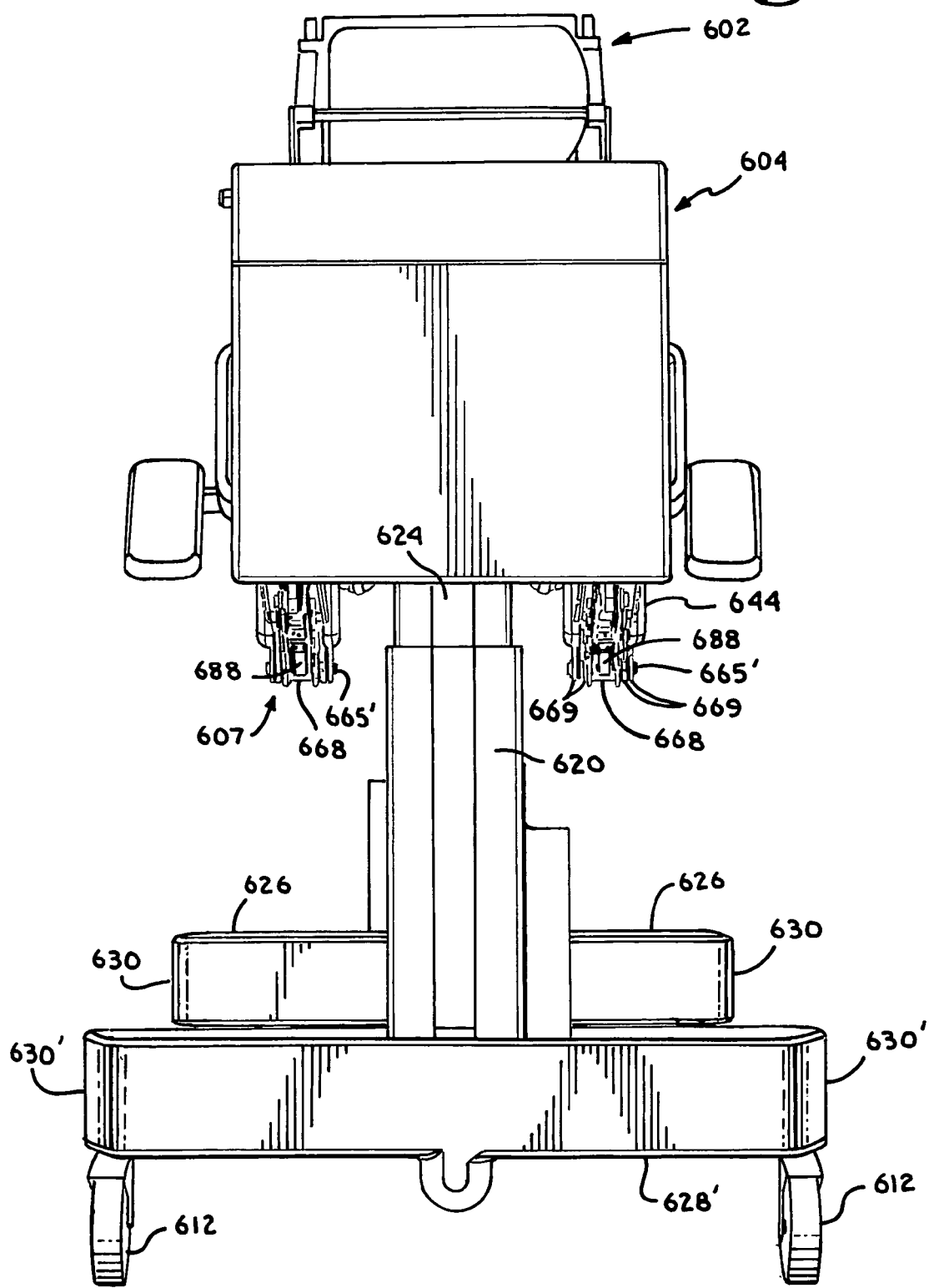
FIG. 61 is an enlarged foot-end elevational view of the patient support structure of FIG. 48 and shown in the same position as shown in FIG. 49.

Pairs of V-links engage the lower axle 665' on either side of the lower roller 668. For example, as shown in FIG. 61, two V-links 669 are joined at the left-hand and right-hand ends, or inner and outer ends, of each of the associated lower axle 665', for a total of four V-links engaging each lower axle 665'. The lower roller 668 is slidingly received on the lower axle 665' so as to be located between the engagements of the pairs of V-links 669, such as is shown in FIG. 53. It is foreseen that only two V-links 669 may be used, such as at only left-hand end or the right-hand end of the associated lower axle 665'.

The lower roller 668 is substantially similar or even identical to the upper roller 667. Accordingly, the lower roller 668 includes a through-bore 668A that pivotably receives the lower axle 665' therethrough. The lower roller 668 is sized and shaped to pivot freely about the lower axle 665'. In the illustrated embodiment, the lower roller 668 includes a circular cross-section. However, it is foreseen that the lower roller 668 may instead be a slide having a cross-section of another shape, such as but not limited to a rectangle, a polygon, an oval, or the like. It is also foreseen that the lower roller 668 may be an alternative structure that provides the same function as the lower roller 668.

The patient support and articulation apparatus 600 includes an orientation subassembly that includes an individually operable and continuously adjustable articulation subassembly 607 interconnected with the rotation subassemblies 616 and 616'. The orientation subassembly cooperatively rotates and articulates at least a portion of the patient support subassembly 606 so as to allow the patient support subassembly 606 to move through a plurality of infinitely adjustable and non-segmented angular orientations in cooperation with one or more of the primary and secondary elevators 616, 614' and 636. The articulation subassembly 607 is adapted to articulate the patient support subassembly 606 at the point of articulation 601 up to 90° up or down, for example in an amount of about ±5°, ±10°, ±15°, ±20°, ±25°, ±30°, ±35°, ±40°, ±45°, ±50° or more with respect to an axis of rotation C and to the subassembly 606 in a horizontal configuration. In some embodiments, the maximum upward breaking position is about +35° and the maximum downward breaking position, or an angle of articulation D, is about −20°, relative to axis C, thereby providing a total range of motion of the point of articulation 601 of about 55°. However, it is foreseen that, in some embodiments, the articulation subassembly 607 may move through an infinitely adjustable non-segmented plurality of angular orientations, so as to break upwardly an amount up to about 90° or more, and as to break downwardly an amount up to about 90°, or more.

Referring to FIGS. 51-53, 58-60 and 66, the articulation subassembly 607 cooperates with the head-end and foot-end lift subassemblies 602 and 604, so as to continuously and non-segmentedly articulate the patient support subassembly 606 at the point of articulation 601 (e.g., modify angle D) while simultaneously substantially maintaining the height H of the point of articulation 601 relative to the floor F. Additionally, during this articulation at the point of articulation 601, the articulation subassembly 607 cooperates with the head-end and foot-end lift subassemblies 602 and 604 so as to maintain the head-end support 654 of the patient support subassembly 606 in a position that is about parallel with the floor F, such that a patient supported thereon will not be in a substantially head-down position. The front tether 690 may be a rod, a band, a cord, a cable, and the like. The rear tether 692 may be fabricated of any suitable elastic or non-elastic material known in the art.

The articulation subassembly 607 includes the gearbox 680 operably linked with a pair of tensioned angulation subassemblies, generally 686, that slidingly engage the hinge upper and lower rollers 667 and 668 so as to cause the hinges 663 to break upwardly and downwardly. Each tensioned angulation subassembly 686 includes a tethered translation wedge 688, the front tether 690, and the tensioned rear tether 692, a trolley slider 694, and a translation member 696 that engages the gearbox 680. The wedge 688 and the rear tether 692 are constantly under tension so as to urge the wedge 688 at the right in FIG. 59 or toward the end.

As shown in FIG. 66, the trolley sliders 694 slidably engage the associated frame 661A from the bottom thereof, such that the trolley sliders 694 at least partially surround the associated frames 661A, including portions of the bottom and two sides of the frames 661A. The trolley sliders 694 are adapted to slide in the cephalad and caudad directions along the frames 661A. In some circumstances, the surfaces of the trolley slider 694 engaging the frame 6612A are lubricated. Each trolley slider 694 is engaged by a front tether 690 that pushes or pulls the trolley slider 694 in cephalad and caudad directions in response to actuation of the tensioned angulation subassembly 696.

A torso trolley 698 rests on the frames 661A and includes slide channel members 700 adapted to slidingly engage the tops and sides of the frames 661A and to releasably engage the trolley sliders 694. Movement of the trolley sliders 694, such as in the cephalad and caudad directions, translates the torso trolley 698 along the frames 661A, such as is described in greater detail below.

The translation wedge 688 includes first and second ends 702 and 704, top and bottom portions 706 and 708, and a pair of opposed faces 710. In the illustrated embodiment, the translation wedge 688 is generally thin, flat and triangular in shape. However, the translation wedge 688 may have any other shape so long as it fulfills its function as described herein. For example, it is foreseen that the translation wedge 668 may be a cam, a roller, a polygon, a sphere, and the like. The translation wedge 688 may be fabricated of any sufficiently strong and resilient material able to withstand high stress and tension resulting from the apparatus 600 supporting a patient weighing up to at least 500-pounds. Suitable materials include but are not limited to aluminum, hardened metals and carbon fiber. It is foreseen that the top and bottom portions 706 and 708 may be treated to increase or decrease lubrication, as is known in the art.

Referring to FIGS. 58-60, 66 and 68-69, a first end 702 of the translation wedge 688 engages the front tether 690, a second end 704 of the translation wedge 688 engages the rear tether 692. The translation wedge top and bottom portions 706 and 708 slidably engages the upper and lower rollers 667 and 668, respectively. The translation wedge 688 is pulled between the upper and lower rollers 667 and 668 by the rear tether 692, which in turn is pushed and pulled by the translation member 696 in response to actuation of the gearbox 680, as is described herein. The wedge 688, because of the weight of the structure acting thereon is always urged away from the rear tether 692, so as to place tension thereon.

Figure 58:
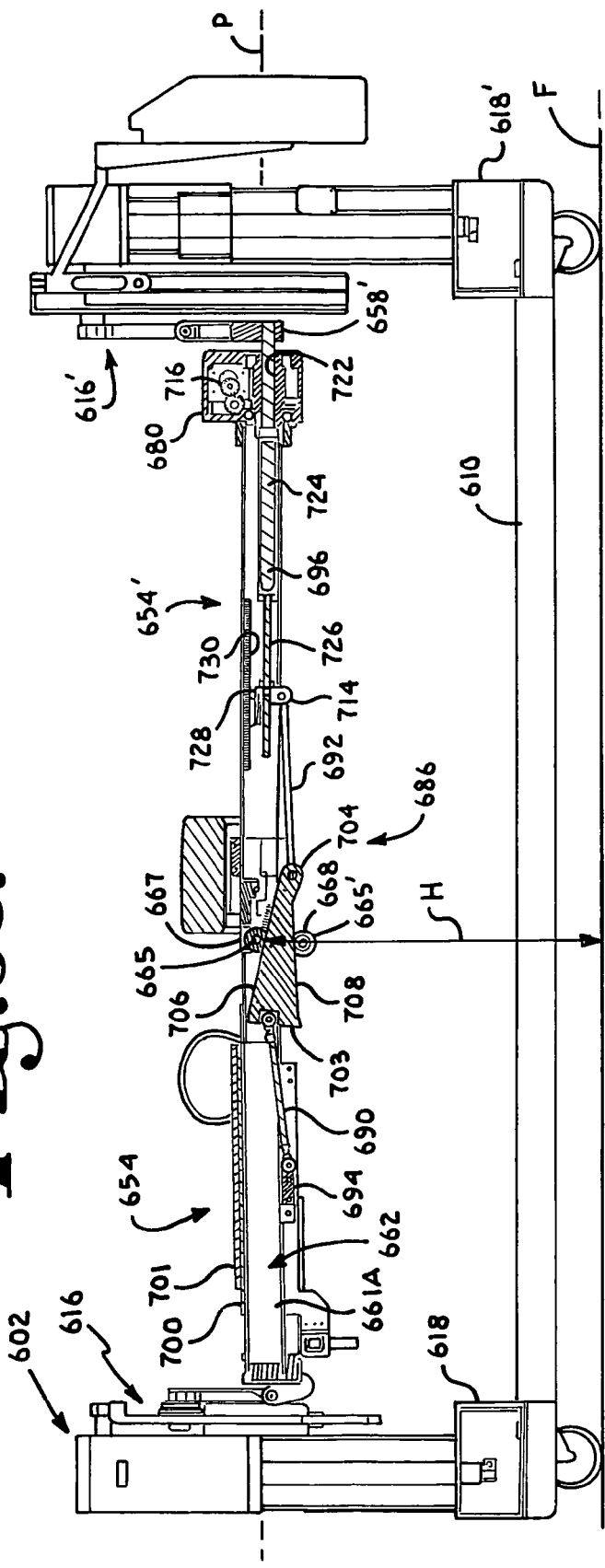
FIG. 58 is an enlarged cross-sectional view of a portion of the patient support structure of FIG. 57, taken along line 58-58 of FIG. 57, and shown in the same position as shown in FIG. 48.

The rear tether 692 includes first and second ends 712 and 714, and may be a rod, a band, a cord, a cable, and the like. The rear tether 692 may be fabricated of any suitable flexible, but generally non-stretchable or non-elastic material known in the art. The rear tether 692 is tensioned between the second end 704 of the translation wedge 688 and the translation member 696. As shown in FIG. 58, the first end 712 of the rear tether 692 engages the second end 704 of the translation wedge 688, and the second end 714 of the rear tether 692 engages the translation member 696 by an intervening translation nut member 728. The rear tether 692 is pulled or released in the cephalad and caudad directions, respectively, through the translation member 696.

The translation member 696 engages the translation nut member 728 and the gearbox 680. As shown in FIGS. 66 and 67, the gearbox 680 includes a motorized gear assembly, generally 716, and a motor 718. In the illustrated embodiment, the gear assembly 716 includes a worm gear. However, it is foreseen that any type of gear assembly 716 may be used, so long as is can move the translation member 696 in the cephalad and caudad directions. The translation member 696 also includes an outer translation structure 720, such as a tube, that passes through a through-bore 722 in the gear assembly 716. An inner translation structure 724, such as a translation rod or bar, slides in and out of the outer translation structure 720. A translation screw 726 is secured to an end of the inner translation structure 724 within the outer translation structure 720. The translation screw 726 engages the translation nut member 728 that engages the second end 714 of the rear tether 692. The translation nut member 728 moves along a translation track 730 located within the elongate slot 662 of the frame 661B, in the cephalad and caudad directions, in response to actuation of the translation screw 726.

To articulate the patient support subassembly 606 in an upwardly or downwardly breaking configuration, or to align the subassembly 606 in the first plane P, the gearbox 680 is actuated. Actuation of the gearbox 680 moves the translation wedge 688 between the upper and lower rollers 667 and 668, in either a cephalad and caudad direction by drawing the tether 692 toward the gearbox 680 or allowing the tether 692 slack so that the tension at the wedge 688 pulls the rear tether away from the gearbox 680. Upward and downward breaking is associated with a distance between the rollers, the distance being generally perpendicular to the floor F. When the rollers 667 and 668 are closer together, the hinge 663 breaks downwardly. When the rollers 667 and 668 are farther apart, the hinge 663 breaks downwardly. Gravity and the weight of the patient facilitate downward breaking. When the translation wedge 688 moves in a cephalad direction, the rollers 667 and 668 roll along the top and bottom portions 706 and 708 towards the translation wedge first end 702, such that the rollers 667 and 668 are pushed apart by the translation wedge 688, thereby causing the patient support subassembly 606 to break downwardly. When the translation wedge 688 moves in a caudad direction, the rollers 667 and 668 roll along the top and bottom portions 706 and 708 towards the translation wedge second end 704, the rollers 667 and 668 move back together, thereby causing the patient support subassembly 606 to break upwardly. Accordingly, a distance between the upper and lower rollers 667 and 668 increases or decreases as the translation wedge 688 moves in the cephalad and caudad directions, respectively.

It is noted that the degree of angulation D is associated with the shape of the translation wedge 688 and the spacial relationship between the translation wedge 688 and the rollers 667 and 668, such as but not limited to the length of the top and bottom portions 706 and 708 and the size of an angle defined by the top and bottom portions 706 and 708 and the second end 704. For example, the longer the top and bottom portions 706 and 708 and/or a greater the angle facilitates moving the rollers 667 and 668 farther apart, and in turn the greater the amount of angulation of the patient support subassembly 606 possible. In a certain embodiment, movement of one inch of the wedge 688 relative to the rollers 667 and 668 translates to ten degrees of angulation; however, it is foreseen that this could be varied greatly, for example one inch could translate to 2, 5, 20 or any selected degrees.

FIG. 58 shows the patient support subassembly 606, or the head-end and foot-end supports 654 and 654', aligned in the first plane P. When the patient support subassembly 606 is aligned with the first plane P, the upper and lower rollers 667 and 668 are located medially between the first and second ends 702 and 704 of the translation wedge 688. Concurrently, the trolley slider 694 is located medially along the length of the head-end support 654. The inner translation structure 724 is moved into the outer translation structure 720, the translation nut member 728 is medially along the translation track 730, and the gearbox 680 is located near the cross-bar 658'.

Figure 59:
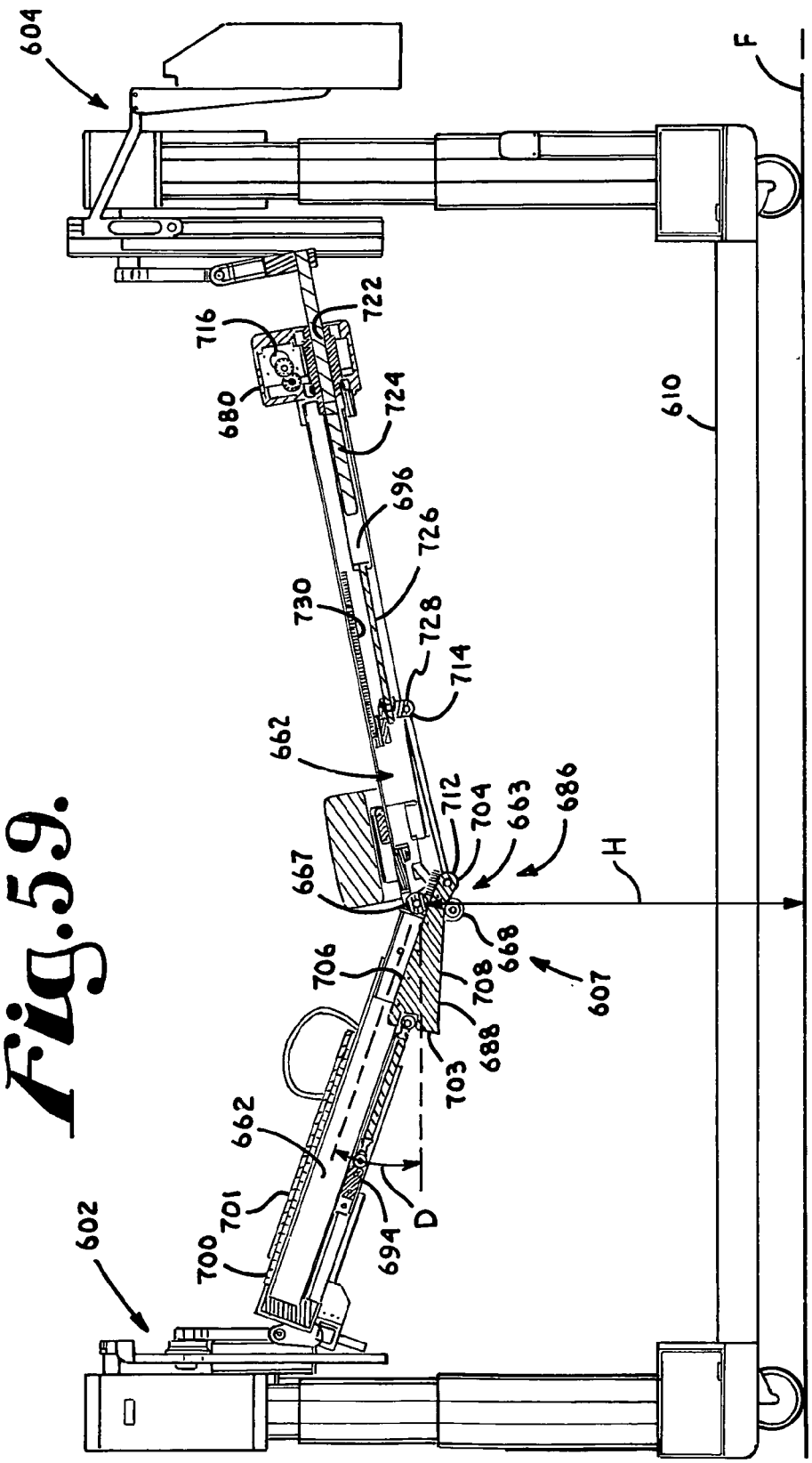
FIG. 59 is an enlarged cross-sectional view of a portion of the patient support structure of FIG. 48, taken along line 58-58 of FIG. 57, and shown in the same position as shown in FIG. 49.

FIG. 59 shows the patient support subassembly 606 in a downwardly breaking configuration, wherein the hinge 663 is located below the first plane P. The apparatus 600 is adapted to move in a smooth, continuously and infinitely adjustable, non-segmented manner between the configuration of FIG. 58 and the configuration shown in FIG. 59 and back again. In the configuration shown in FIG. 59, the upper and lower rollers 667 and 668 are located near the second end 704 of the translation wedge 688. When moving from the FIG. 58 configuration to the FIG. 59 configuration, the trolley slider 694 moves "up hill" in a cephalad direction, or towards the head-end lift subassembly 602. Movement of the trolley slider 694 moves the torso trolley 698 towards the head-end lift subassembly 602 a distance associated with the amount of downward breaking or angulation of angle D. The translation wedge 688 is sized and shaped such that when the hinge 663 breaks downwards, the torso trolley 670 slides towards the head-end lift subassembly 602, or "up hill." It is noted that in the configuration of FIG. 59, the translation nut member 728 has moved along the translation track 730, towards the hinges 663. Accordingly, the translation wedge 688 has been drawn between the rollers 667 and 668, which roll along the top and bottom portions 706, 708 until the rollers 667 and 668 are located near the translation wedge second end 704. The translation nut member 728 has also moved along the translation screw 726 towards the head-end lift subassembly 602, which is actuated by rotation of the translation screw 726. Further, actuation of the gearbox 680 rotates the translation screw 726 and moves the inner translation structure 724 away from the foot-end lift subassembly 604, effectively lengthening the foot-end lift subassembly 604.

FIG. 60 shows the patient support subassembly 606 in an upwardly breaking configuration, wherein the hinge 663 is located above the first plane P. The apparatus 600 is adapted to move in a smooth, continuously adjustable, non-segmented manner between the configuration of FIG. 58 and the configuration shown in FIG. 60 and back again. In the configuration shown in FIG. 60, the upper and lower rollers 667 and 668 are located near the first end 702 of the translation wedge 688. It is noted that the trolley slider 694 is again moved "up hill", in a caudad direction, or towards the foot-end lift subassembly 604. Movement of the trolley slider 694 moves the torso trolley 698 away from the head-end lift subassembly 602 a distance associated with the amount of downward breaking or angulation of angle D. The translation wedge 688 is sized and shaped such that when the hinge 663 breaks upward, the torso trolley 670 slides towards the foot-end lift subassembly 604, also up hill. It is noted that in the configuration of FIG. 60, the translation nut member 728 has moved along the translation track 730, towards the foot-end lift subassembly 604. Accordingly, the translation wedge 688 has been pulled between the rollers 667 and 668, until the rollers 667 and 668 are located near the first end 702 of the translation wedge 688. The translation nut member 728 has also moved along the translation screw 726 towards the foot-end lift subassembly 604, which is actuated by rotation of the translation screw 726. Further, actuation of the gearbox 680 rotates the translation screw 726 and moves the inner translation structure 724 towards the foot-end lift subassembly 604, effectively lengthening the foot-end lift subassembly 604. It is again noted that when the apparatus 600 is in the configuration shown in FIG. 60, wherein the hinge 663 is in an upwardly breaking configuration and the foot-end lift subassembly 604 is in its lowest possible configuration and the primary and secondary elevators are both maximally lowered, the intersection of the inner translation member 728 and the cross-bar 658' are substantially near the floor F, such that the ends of the cross-bar 658' pass around the cross-bar 610 of the base support 608 and portions 684 of the gearbox 680 pass around the cross-bar 610 so as to be located near the floor F, instead of being located above the cross-bar 610. This enables maintaining the head-end support 654 in a substantially horizontal position, relative to the floor F, such as by raising the head-end lift subassembly 602, while providing the amount or degree of angulation at the point of angulation 601 required to a given surgical procedure.

The distance the torso trolley 670 moves is associated with the change in angulation of angle D, which in turn is associated with the location of the upper and lower rollers 667 and 668 relative to the translation wedge 688. The distance between the trolley slider 694 and the translation wedge 688 is fixed by the length of the front tether. Accordingly, the greater the change in angle D, the farther the torso trolley 670 is moved. In an exemplary embodiment, a change in the angle D is associated with about movement of the torso trolley 670 that is approximately equal to the shortening of the distance between the opposite ends of the patient support or the change in the hypotenuse associated with the patient support subassembly. Depending upon the shape and size of the translation wedge 688 and other factors, this can vary somewhat so as to provides the optimal positioning of the patient's torso. It is foreseen that, if the amount of change in angulation is represented by the letter W and the amount of distance moved by the torso trolley is represented by the letter V, that the ratio of W:V may vary.

The apparatus 600 includes a failsafe structure, generally 732, adapted to operably engage the articulation subassembly 607 in the event of catastrophic failure of the apparatus 600. Catastrophic failure includes but is not limited to physical or mechanical breaking, or wearing out, of a hinge 663, a V-link 669, the translation wedge 688, a front or rear tether 690, 692, loosening of a screw or bolt, wearing out of a gear or motor, and electrical failure. It is foreseen that numerous failsafe devices known in the art can be incorporated into the apparatus 600, into various components such as the head-end and foot-end lift subassemblies 602 and 604, and the patient support subassembly 606.

Figure 65:
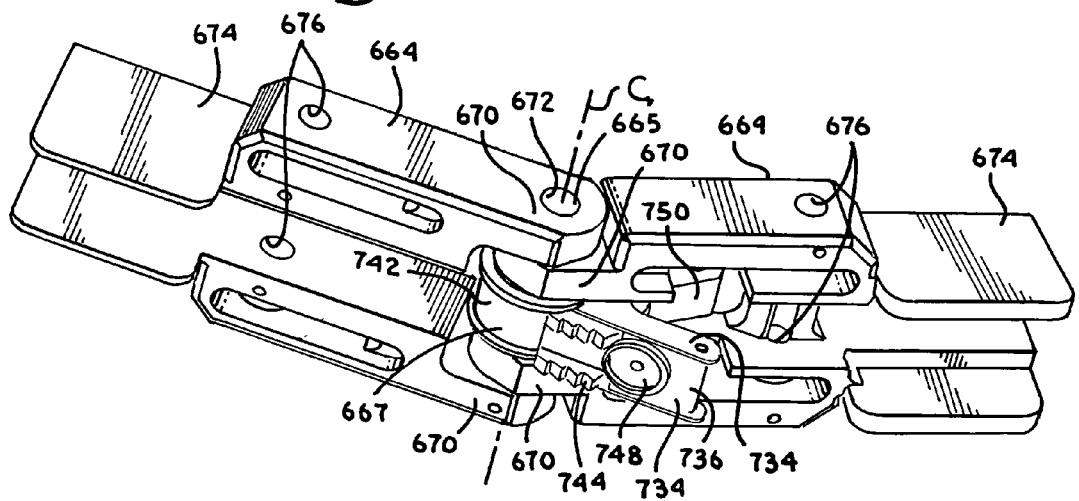
FIG. 65 is an enlarged bottom perspective view of the hinge and roller of FIG. 64.

In the illustrated embodiment of the invention, the failsafe structure 732 is associated with the hinges 663 and the translation wedge 688. Referring to FIGS. 65, 68 and 69, the failsafe structure 732 includes at least one, preferably two guides 734, a ratchet locking structure 736, pawl or ratchet break 735, and a toothed ratcheted strip 738 attached to at least one face 710 of the translation wedge 688 adjacent to the top portion 706 thereof. The ratchet locking structure 736 is located between two guides 734 and includes a gripping surface 740 sized and shaped to grippingly engage the surface 742 of the upper roller 667. The ratchet locking structure 736 also includes a plurality of ratchet teeth 744 sized and shaped to engage the ratchet teeth 746 of the ratcheted strip 738. The failsafe structure 732 may include a device for preventing engagement of the teeth 744 and 746, such as but not limited to a solenoid 748. For example, a solenoid 748 such as shown in FIG. 65 may bias the ratchet locking structure 736 upwardly, so as to block engagement of the teeth 744 and 746. A leaf spring 750 biases the ratchet locking structure 736 downwardly, so as to facilitate engagement of the teeth 744 and 746 and it is foreseen that this function could be provided by a solenoid or other device.

During normal operation of the apparatus 600, when the translation wedge 688 is moved towards the foot-end lift subassembly 604, the ratchet locking structure 736 slides along the ratcheted strip 738, such that the teeth 744 and 746 do not become engaged. Alternatively, the ratchet locking structure 736 may be biased upwardly, such as by the solenoid 748, so that the teeth 744 and 746 do not become engaged. When the translation wedge 688 is moved towards the head-end lift subassembly 602, the ratchet locking structure 736 is biased upwardly, such as by the solenoid 748, so that the teeth 744 and 746 do not become engaged.

In the event of a catastrophic failure of the apparatus 600, for example power failure, the solenoid 748 no longer maintains separation and the teeth 744 of the downwardly biased ratchet locking structure 736 engage the ratcheted strip teeth 746. Since the translation wedge 688 is biased towards the head-end lift subassembly 602 by downward forces from the weight of the patient on the assembly 600, the translation wedge 688 pulls or pushes the ratcheted locking structure 736 between the upper roller 667 and the translation wedge top portion 706. The gripping surface 740 non-slidingly engages the surface 742 of the upper roller 667 and the ratchet teeth 744 of the ratchet locking structure 736 lockingly engages the ratcheted strip 738, thereby locking or binding-up translation wedge 688 and the upper roller 667, and substantially blocking further movement or articulation of the articulation subassembly 607.

The apparatus 600 includes a powered actuator and electronics such as are known in the art and described herein.

As described above, the head-end support 654 slidably supports the torso trolley 670. A number of attachments may be removably attached to the head-end and foot-end supports and/or the torso trolley 670 such as but not limited to arm supports, a chest pad, hip pads, flat operating boards, radiopaque boards, straps for securing the patient to the frames 661A, 661B, such as are known in the art and described herein.

It is to be understood that while certain forms of the present invention have been illustrated and described herein, it is not to be limited to the specific forms or arrangement of parts described and shown.

What is claimed and desired to be secured by Letters Patent is as follows:

1. A patient support apparatus for supporting a patient above a floor during a medical procedure, the apparatus comprising:
   a) an elongate patient support having first and second ends and a head portion and a foot portion that are joined by a pair of spaced opposed hinge structures, articulatable with respect to each other and lockable in a planar configuration and a plurality of angular configurations relative to each other;
   b) a first end support connected to the patient support first end, and being vertically adjustable so as to provide for selective positioning of the first end relative to the floor supporting the apparatus;
   c) a torso trolley movably positionable upon the patient support head portion, wherein the torso trolley is adapted to support the torso of a patient on the apparatus;
   d) a trolley positioner operably determining an articulation between the head and foot portions and cooperatively positioning the trolley on the head portion in a predetermined location relative to the head portion in response to the determined articulation; and
   e) a secondary vertical elevator located between the first end and the first support to provide vertical adjustment of the first end relative to the floor in cooperation with the first support.

2. The apparatus according to claim 1, including:
   a) a second end support connected to the second end of the patient support and being vertically adjustable to provide for selective positioning of the second end above the floor.

3. The apparatus according to claim 2 wherein:
   a) the first and second ends are articulatable with respect to the first and second end supports.

4. The apparatus according to claim 3 wherein:
   a) the first end is connected to the first support by a first translation mechanism that operably allows articulation of the head and foot portions with respect to each other and to the end supports without horizontal movement of the end supports relative to each other.

5. The apparatus according claim 1, wherein the pair of hinge structures between the head and foot portions is provided by a universal axis gears joining the head and foot portions.

6. An apparatus for supporting a patient above a floor during a medical procedure, the apparatus comprising:
   a) a selectively height adjustable support subassembly with respect to the floor including first and second spaced opposed end supports; each end support including an independently and cooperatively operating primary elevator, the second end support including an independently and cooperatively operating secondary elevator;
   b) an elongate patient support subassembly extending between the first and second end supports and held by the first and second end supports in spaced relation with respect to the floor, the elongate patient support subassembly having head and foot end portions pivotably connected by a joint structure so as to be alignable in a first plane;
   c) an orientation subassembly including interconnected rotation and angulation subassemblies cooperatively rotating and articulating at least a portion of the elongate patient support subassembly so as to allow the elongate patient support subassembly to move through a plurality of angular orientations thereof in cooperation with one or more of the primary and secondary elevators, while the joint structure is spaced a substantially constant height from the floor when being moved through the plurality of angular orientations and without the first and second end supports moving towards or away from each other along the floor; and
   d) a torso trolley associated with the head end portion and cooperating with the orientation subassembly that is movable to a preselected position relative to each of the angular orientations of the elongate patient support subassembly.

7. The apparatus of claim 6, wherein the joint structure comprises a hinge structure.

8. The apparatus of claim 6, wherein the orientation subassembly comprises a cam structure.

9. The apparatus of claim 8, wherein the cam structure is attached to an inboard end of each of the head and foot end portions.

10. The apparatus of claim 6, wherein the orientation subassembly comprises a rack and pinion structure.

11. The apparatus of claim 6, wherein at least one of the first or second end supports further comprises at least a portion of the rotation subassembly.

12. The apparatus of claim 6, wherein the elongate patient support subassembly is a frame and further comprising a second patient support structure, the second patient support structure being an imaging table.

13. The apparatus of claim 6, wherein the plurality of angular orientations includes a maximum upward breaking position of about +35°.

14. The apparatus of claim 6, wherein the plurality of angular orientations includes a maximum downward breaking position of about −20°.

15. The apparatus of claim 6, wherein the plurality of angular orientations includes a total range of motion of about 55°.

16. The apparatus of claim 15, wherein the total range of motion includes a maximum upward range of motion of about +35°.

17. The apparatus of claim 15, wherein the total range of motion includes a maximum downward range of motion of about −20°.

18. The apparatus of claim 6, wherein a portion of an outboard end of the foot end portion is lowered below a portion of a base structure, when the primary and secondary elevators of the second end support are maximally lowered.

19. The apparatus of claim 18, wherein the patient support assembly is pivoted about +35°.

20. The apparatus of claim 18, wherein the patient support assembly is pivoted about −20°.

21. A continuously non-segmentedly adjustable apparatus for supporting a patient above a floor during a medical procedure, the apparatus comprising:
   a) a lift subassembly including
      i) a first upright pier with an individually operable and continuously adjustable first primary elevator;
      ii) a second upright pier in opposed and spaced relation with the first upright pier, and having an individually operable and continuously adjustable second primary elevator and an individually operable and continuously adjustable secondary elevator; and
      iii) a base joining the first and second upright piers;
   b) an elongate patient support subassembly including head and foot support structures joined by a pivot and alignable in a first plane, and a torso trolley slidingly engaging the head support structure in cooperation with movement of the pivot, wherein the pivot is adapted for upward and downward breaking; and
   c) an orientation subassembly including rotation and angulation subassemblies cooperating with the first and second piers and the elongate patient support subassembly, so as to rotate, articulate and lift at least a portion of the patient support subassembly so as to allow the patient support structure to move through a non-segmented plurality of angular orientations thereof without the end supports moving relative to each other while the height between the pivot and the floor is substantially constant during angulation only; and
   d) a powered actuator to move the pivot.

22. The apparatus according to claim 21, wherein the angulation subassembly includes the pivot.

23. The apparatus according to claim 21, wherein the pivot includes a total range of motion of from about +55° to about −20° relative to the first plane.

24. The apparatus according to claim 21, wherein the pivot further comprises a hinge structure.

25. The apparatus of claim 21, wherein the pivot comprises a cam structure.

26. The apparatus of claim 25, wherein the cam structure is attached to an inboard end of each of the head and foot support structures.

27. The apparatus of claim 21, wherein the pivot comprises a rack and pinion structure.

28. The apparatus of claim 21, wherein a portion of an outboard end of the foot support structure is lowered below a portion of the base, when the primary and secondary elevators of the second upright pier are maximally lowered.

29. The apparatus of claim 28, wherein the pivot can be manipulated about +35° relative to the first plane.

30. The apparatus of claim 28, wherein the pivot can be manipulated about −20° relative to the first plane.

31. An adjustable apparatus for supporting a patient above a floor during a medical procedure, the apparatus comprising:
   a) an elongate patient support subassembly including
      i) a first end portion with inboard and outboard ends and a torso trolley slidable between the inboard and outboard ends of the first end portion;
      ii) a second end portion with inboard and outboard ends;
      iii) an upwardly and downwardly breaking hinge pivotably joining the inboard ends of the first and second end portions;
      iv) the first and second end portions being alignable in a first plane, and
      v) the torso trolley cooperating with the hinge so as to non-segmentedly slide between the associated inboard and outboard ends;
   b) a support subassembly holding the patient support subassembly in spaced relation with respect to the floor, and including
      i) a continuously adjustable selectively telescoping upright first pier joined with the outboard end of the first end portion and having cooperating non-segmentedly adjustable primary first elevator;
      ii) a continuously adjustable selectively telescoping upright second pier joined with the outboard end of the second end portion and having cooperating non-segmentedly adjustable primary and secondary second elevators; and
      iii) a non-telescoping base structure holding the first and second piers in opposed spaced relation to one another;
   c) a continuously adjustable orientation subassembly including interconnected rotation and angulation subassemblies cooperatively rotating and articulating at least a portion of the patient support subassembly so as to allow the patient support structure to move through a number of non-segmented angular orientation thereof in cooperation with one or more of the primary and secondary first and second elevators while the height of the hinge above the floor is substantially constant during angulation only; and
   d) a powered actuator to move the hinge upward and downward.

32. The apparatus according to claim 31, wherein the hinge includes first and second positions, the first position including a bend of about +35° relative to the first plane and the second position including a bend of about −20° relative to the first plane.

33. The apparatus according to claim 32, the torso trolley being operable to slide towards the inboard end of the first end portion in cooperation with the hinge moving in a direction away from the first plane and towards the first position.

34. The apparatus according to claim 33, the torso trolley being operable to slide towards the outboard end of the first end portion in cooperation with the hinge moving in a direction away from the first position and towards the first plane.

35. The apparatus according to claim 32, the torso trolley being operable to slide towards the inboard end of the first end portion in cooperation with the hinge moving in a direction away from the first plane and towards the second position.

36. The apparatus according to claim 35, the torso trolley being operable to slide towards the outboard end of the first end portion in cooperation with the hinge moving in a direction away from the second position and towards the first plane.

37. A continuously adjustable patient support and articulation apparatus for supporting a patient above a floor during a medical procedure, the apparatus comprising:
   a) first and second spaced lift subassemblies, the first lift subassembly including an individually operable and continuously adjustable primary lift subassembly, the second lift subassembly including an individually operable, continuously adjustable and operably joined primary and secondary lift subassemblies;
   b) a patient support subassembly rotatably joined with the first and second spaced lift subassemblies, the patient support subassembly including head-end and foot-end supports, each of the head-end and foot-end supports having an inboard end and an outboard end, the head-end and foot-end supports being pivotably joined at their inboard ends and alignable in a first plane, and the head-end support including a torso trolley slidably engaged thereby;

c) an individually operable and continuously adjustable articulation subassembly operably joined with the head-end support, the foot-end support, and the torso trolley, and including articulating structure for articulating the head-end and foot-end supports with respect to the first plane while simultaneously translating the torso trolley along the head-end support in a direction associated with an angle of articulation, while the articulating structure is spaced a substantially constant height from the floor supporting the apparatus during angulation only; and d) a powered actuator to move the articulating structure.

38. The apparatus according to claim 37, wherein the articulation structure includes a hinge with first and second positions, the first position including a first angle of articulation of about +35° relative to the first plane and the second position including a second angle of articulation of about −20° relative to the first plane.

39. The apparatus according to claim 38, the torso trolley being operable to slide towards the inboard end of the head-end support in cooperation with the articulation structure moving in a direction away from the first plane and towards the first position.

40. The apparatus according to claim 39, the torso the head-end support in cooperation with the articulation structure moving in a direction away from the first position and towards the first plane.

41. The apparatus according to claim 39, the torso trolley being operable to slide towards the inboard end of the head-end support in cooperation with the articulation structure moving in a direction away from the first plane and towards the second position.

42. The apparatus according to claim 37, the torso trolley being operable to slide towards the outboard end of the head-end support in cooperation with the articulation structure moving in a direction away from the second position and towards the first plane.

43. The apparatus according to claim 38, wherein the articulating structure includes a pivot.

44. The apparatus according to claim 43, wherein the pivot includes a total range of motion of from about +55° to about −20° relative to the first plane.

45. The apparatus according to claim 43, wherein the pivot further comprises a hinge structure.

46. The apparatus of claim 45, wherein the pivot comprises a cam structure.

47. The apparatus of claim 46, wherein the cam structure is attached to the inboard end of each of the head-end and foot-end supports.

48. The apparatus of claim 43, wherein the pivot comprises a rack and pinion structure.

49. The apparatus of claim 43, wherein the first and second lift subassemblies are operably joined by a base and a portion of the outboard end of the foot-end support is lowerable below a portion of the base, when the primary and secondary lift subassemblies of the second lift subassembly are maximally lowered.

50. The apparatus of claim 48, wherein the pivot includes and angle of about +35° relative to the first plane.

51. The apparatus of claim 49, wherein the pivot includes and angle of about −20° relative to the first plane.

52. The apparatus of claim 38, wherein the articulation structure includes
a) a hinge joining the inboard ends of the head-end and foot-end supports, the hinge including a first axis of rotation;
b) a first roller coaxial with the first axis of rotation;
c) a second roller spaced from the first roller and having a second axis of rotation substantially parallel to the first axis of rotation;
d) an elongated wedge slidably engaging the first and second rollers and movable in a direction perpendicular to the first and second axes of rotation, so as to vertically bias the first and second rollers away from one another; and
e) a motorized gear assembly located at an outboard end of the foot-end support and operably joined with a first end of the elongated wedge so as to longitudinally move the elongated wedge and thereby cause a change in an angle of articulation of the hinge.

53. The apparatus of claim 52, wherein the angle of articulation is between about +35° and about −20° relative to the first plane.

54. The apparatus of claim 52, the articulation structure further including a linking rod operably joining a second end of the elongated wedge with the torso trolley, such that the torso trolley slides on the head-end support in a direction and a distance associated with longitudinal movement of the elongated wedge.

55. The apparatus of claim 52, wherein the elongated wedge includes first and second opposed ends, the first end having a first height and the second end having a second height substantially greater than the first height, wherein when the first and second rollers engage the elongated wedge adjacent to the first end, the hinge articulates in a downwardly breaking position, and when the first and second rollers engage the elongated wedge adjacent to the second end, the hinge articulates in an upwardly breaking position.

56. The apparatus of claim 52, further including a failsafe structure adapted to operably engage the articulation structure in the event of mechanical failure of the articulation structure.

57. The apparatus of claim 56, the failsafe structure including a ratcheted break.

58. The apparatus of claim 57, the ratcheted break including
a) a strip of ratchet teeth adjacent to a top side of the elongated wedge; and
b) a pawl having ratchet teeth sized and shaped to engage the strip of ratchet teeth and a scooped nose sized and shaped to engage the first roller.

59. The apparatus of claim 58, the ratcheted break further including a downwardly biasing structure for biasing the pawl towards the strip of ratchet teeth, and an upwardly biasing structure of biasing the pawl away from the strip of ratchet teeth.

60. An adjustable apparatus for supporting a patient above a floor during a medical procedure, the apparatus comprising:
a) an elongate patient support subassembly including
i) a first end portion with inboard and outboard ends and a torso trolley slidable between the inboard and outboard ends of the first end portion;
ii) a second end portion with inboard and outboard ends;
iii) an upwardly and downwardly breaking hinge structure pivotably joining the inboard ends of the first and second end portions, the hinge structure being spaced a height above the floor supporting the apparatus;
iv) the first and second end portions being alignable in a first plane, and
v) the torso trolley cooperating with the hinge structure so as to non-segmentedly slide between the associated inboard and outboard ends;

b) a support subassembly holding the patient support subassembly in spaced relation with respect to the floor, and including
   i) a continuously adjustable upright first pier joined with the outboard end of the first end portion and having cooperating non-segmentedly adjustable primary first elevator;
   ii) a continuously adjustable upright second pier joined with the outboard end of the second end portion and having cooperating non-segmentedly adjustable primary and secondary second elevators; and
   iii) a non-telescoping base structure holding the first and second piers in opposed spaced relation to one another;
c) a continuously adjustable orientation subassembly including interconnected rotation and angulation subassemblies cooperatively rotating and articulating at least a portion of the patient support subassembly so as to allow the patient support structure to move through a number of non-segmented angular orientation thereof in cooperation with one or more of the primary and secondary first and second elevators while the height of the hinge structure above the floor is substantially constant during angulation only; and
d) a powered actuator to move the continuously adjustable orientation subassembly and the support subassembly.

61. The apparatus according to claim 4, wherein:
a) the second end is connected to the second support by a second translation mechanism that operably allows articulation of the head and foot portions with respect to each other and to the end supports without horizontal movement of the end supports relative to each other.

62. An apparatus for supporting a patient above a floor during a medical procedure, the apparatus comprising:
a) a selectively height adjustable support subassembly with respect to the floor including first and second spaced opposed end supports; each end support including an independently and cooperatively operating primary elevator, the second end support including an independently and cooperatively operating secondary elevator;
b) an elongate patient support subassembly extending between the first and second end supports and held by the first and second end supports in spaced relation with respect to the floor, the elongate patient support subassembly having head and foot end portions pivotably connected by a joint structure so as to be alignable in a first plane;
c) the joint structure orientation subassembly including an angulation subassembly configured to articulate at least a portion of the elongate patient support subassembly so as to allow the elongate patient support subassembly to move through a plurality of angular orientations thereof in cooperation with one or more of the primary and secondary elevators, while the joint structure is spaced a substantially constant height from the floor when being moved through the plurality of angular orientations and without the first and second end supports moving towards or away from each other along the floor; and
d) a torso trolley associated with the head end portion and cooperating with the orientation subassembly that is movable to a preselected position relative to each of the angular orientations of the patient support subassembly.

63. The apparatus of claim 62, wherein the joint structure comprises a hinge structure.

64. The apparatus of claim 62, wherein the joint structure orientation subassembly comprises a cam structure.

65. The apparatus of claim 64, wherein the cam structure is attached to an inboard end of each of the head and foot end portions.

66. The apparatus of claim 62, wherein the orientation subassembly comprises a rack and pinion structure.

67. The apparatus of claim 62, wherein at least one of the first or second end supports further comprises at least a portion of the rotation subassembly.

68. The apparatus of claim 62, wherein the elongate patient support subassembly is a frame and further comprising a second patient support structure, the second patient support structure being an imaging table.

69. A patient support apparatus for supporting a patient above a floor during a medical procedure, the apparatus comprising:
a patient support structure supported on at least one end and positioned above the floor by an end support structure, the patient support structure comprising a head end section coupled with a foot end section by a pair of spaced apart hinges; and
a torso trolley movably positionable on the head end section of the patient support structure and configured to support a patient torso thereon, the torso trolley operably coupled with the pair of spaced apart hinges via a linking rod,
wherein articulation of the head end section relative to the foot end section about the spaced apart hinges is configured to cause the linking rod and the torso trolley to move in a same direction.

70. The patient support apparatus of claim 69, wherein, as the linking rod is translated away from the spaced apart hinges, the torso trolley translates away from the spaced apart hinges.

71. The patient support apparatus of claim 69, wherein, as the linking rod is translated towards the spaced apart hinges, the torso trolley translates towards the spaced apart hinges.

72. The patient support apparatus of claim 69, further comprising an elongated wedge slidably engaging first and second rollers positioned at or near the spaced apart hinges, the linking rod coupled to the elongate wedge.

73. The patient support apparatus of claim 69, wherein the patient support structure is supported on opposite ends by a first and a second end support structure.

74. A patient support apparatus for supporting a patient above a floor during a medical procedure, the apparatus comprising:
a patient support structure comprising a head end section coupled with a foot end section by a hinge, the patient support structure supported on a first end and positioned above the floor by a first end support structure; and
a torso trolley positionable on the head end section and moveable relative to the hinge, the torso trolley configured to support a patient torso thereon and linked with the hinges by a linking rod such that the linking rod and the torso trolley are configured to move away from the hinge when the patient support structure articulates about the hinge in a first direction.

75. The patient support apparatus of claim 74, wherein the first direction corresponds with positioning a prone patient in extension.

76. The patient support apparatus of claim 74, wherein the linking rod and the torso trolley are configured to move towards from the hinge when the patient support structure articulates about the hinge in a second direction.

77. The patient support apparatus of claim 76, wherein the first second corresponds with positioning a prone patient in flexion.

78. The patient support apparatus of claim 74, further comprising an elongated wedge slidably engaging first and second rollers positioned at or near the hinge, the linking rod coupled to the elongate wedge.

79. The patient support apparatus of claim 78, wherein the patient support structure is supported on a second end by a second end support structure that is opposed to the first end support structure.

80. A patient support apparatus for supporting a patient above a floor during a medical procedure, the apparatus comprising:
a patient support structure comprising a head end section coupled with a foot end section by a pair of spaced apart hinges, the patient support structure positionable above the floor and supported on outer first and second ends by respective first and second end support structures, the first end support structure comprising a first lift assembly configured to raise and lower the first end of the patient support structure, the second end support structure comprising a second lift assembly configured to raise and lower the second end of the patient support structure, wherein the head end section and the foot end section are configured to articulate relative to each other about the pair of spaced apart hinges while simultaneously substantially maintaining a substantially constant height of the pair of spaced apart hinges relative to the floor.

81. The patient support apparatus of claim 80, further comprising an articulation assembly cooperatively linked with the first and second lift assemblies so as to articulate the head end section and foot end section relative to each other about the pair of spaced apart hinges while simultaneously substantially maintaining the height of the pair of spaced apart hinges relative to the floor.

82. The patient support apparatus of claim 81, wherein the articulation assembly comprises a powered actuator configured to actively articulate the patient support structure about the pair of spaced apart hinges.

83. The patient support apparatus of claim 80, wherein articulation of the head end section and the foot end section relative to each other includes upward breaking of the patient support structure.

84. The patient support apparatus of claim 80, wherein articulation of the head end section and the foot end section relative to each other includes downward breaking of the patient support structure.

85. A patient support apparatus for supporting a patient above a floor during a medical procedure, the apparatus comprising:
a patient support structure supported on at least one end and positioned above the floor by an end support structure, the patient support structure comprising a head end section coupled with a foot end section by a pair of spaced apart hinges; and
a torso trolley movably positionable on the head end section of the patient support structure and configured to support a patient torso thereon, the torso trolley operably coupled to a linking rod,
wherein when the head end section and the foot end section are articulated about the spaced apart hinges, the linking rod and the torso trolley move in a same direction.

* * * * *